US012569453B2

(12) United States Patent
Kraus et al.

(10) Patent No.: US 12,569,453 B2
(45) Date of Patent: Mar. 10, 2026

(54) USE OF TAPINAROF FOR THE TREATMENT OF ATOPIC DERMATITIS

(71) Applicant: Dermavant Sciences GmbH, Basel (CH)

(72) Inventors: John E. Kraus, Pittsboro, NC (US); James Lee, Durham, NC (US)

(73) Assignee: DERMAVANT SCIENCES GMBH, Basel (CH)

( * ) Notice: Subject to any disclaimer, the term of this patent is extended or adjusted under 35 U.S.C. 154(b) by 35 days.

(21) Appl. No.: 18/163,631

(22) Filed: Feb. 2, 2023

(65) Prior Publication Data

US 2023/0190673 A1 Jun. 22, 2023

Related U.S. Application Data

(63) Continuation of application No. 17/871,663, filed on Jul. 22, 2022, now Pat. No. 11,590,088, which is a continuation of application No. 16/682,485, filed on Nov. 13, 2019, now Pat. No. 11,497,718, which is a continuation-in-part of application No. 16/682,476, filed on Nov. 13, 2019, now abandoned.

(60) Provisional application No. 62/833,269, filed on Apr. 12, 2019, provisional application No. 62/833,276, filed on Apr. 12, 2019, provisional application No. 62/760,692, filed on Nov. 13, 2018, provisional application No. 62/760,704, filed on Nov. 13, 2018.

(51) Int. Cl.

| | |
|---|---|
| ***A61K 31/05*** | (2006.01) |
| ***A61K 9/00*** | (2006.01) |
| ***A61K 9/107*** | (2006.01) |
| ***A61P 17/04*** | (2006.01) |
| ***A61P 17/06*** | (2006.01) |

(52) U.S. Cl.

CPC ............ *A61K 31/05* (2013.01); *A61K 9/0014* (2013.01); *A61K 9/107* (2013.01); *A61P 17/04* (2018.01); *A61P 17/06* (2018.01)

(58) Field of Classification Search

CPC ...................................................... A61K 31/05

See application file for complete search history.

(56) References Cited

U.S. PATENT DOCUMENTS

| | | | | |
|---|---|---|---|---|
| 4,723,028 | A | 2/1988 | Shudo | |
| 5,478,856 | A | 12/1995 | Suzuki et al. | |
| 5,547,983 | A | 8/1996 | Charpentier | |
| 5,961,970 | A | 10/1999 | Lowell et al. | |
| 6,689,922 | B1 | 2/2004 | Bernardon | |
| 6,790,869 | B2 | 9/2004 | Ghai et al. | |
| 7,321,050 | B2 | 1/2008 | Chen et al. | |
| 7,868,047 | B2 | 1/2011 | Chen et al. | |
| 8,487,009 | B2 | 7/2013 | Chen et al. | |
| 9,308,239 | B2 | 4/2016 | Thiboutot et al. | |
| 10,195,160 | B2 | 2/2019 | Sonti et al. | |
| 10,376,475 | B2 | 8/2019 | Cote-Sierra et al. | |
| 11,590,088 | B2 | 2/2023 | Kraus et al. | |
| 2002/0032171 | A1 | 3/2002 | Chen et al. | |
| 2003/0059470 | A1 | 3/2003 | Muller | |
| 2003/0073712 | A1 | 4/2003 | Wang et al. | |
| 2003/0171429 | A1 | 9/2003 | Chen et al. | |
| 2006/0246098 | A1 | 11/2006 | Rao et al. | |
| 2007/0264344 | A1 | 11/2007 | Segura-Orsoni et al. | |
| 2008/0255245 | A1 | 10/2008 | Chen et al. | |
| 2010/0094041 | A1 | 4/2010 | Chen et al. | |
| 2010/0221194 | A1 | 9/2010 | Loupenok | |
| 2012/0149748 | A1 | 6/2012 | Shanler et al. | |
| 2013/0028850 | A1 | 1/2013 | Tamarkin et al. | |
| 2013/0273172 | A1 | 10/2013 | Roy et al. | |
| 2013/0303495 | A1 | 11/2013 | Dhingra et al. | |
| 2014/0072583 | A1 | 3/2014 | Ardeleanu et al. | |
| 2014/0213564 | A1 | 7/2014 | Hardas et al. | |
| 2016/0287531 | A1 | 10/2016 | Vander Jagt et al. | |
| 2016/0338973 | A1* | 11/2016 | Sonti | A61P 17/10 |
| 2017/0360719 | A1 | 12/2017 | Cote-Sierra et al. | |
| 2018/0064656 | A1 | 3/2018 | Sonti et al. | |
| 2019/0144367 | A1 | 5/2019 | Andrews et al. | |
| 2019/0151255 | A1 | 5/2019 | Sonti et al. | |
| 2022/0395472 | A1 | 12/2022 | Rubenstein et al. | |
| 2023/0126208 | A1 | 4/2023 | Sonti et al. | |

(Continued)

FOREIGN PATENT DOCUMENTS

| | | | |
|---|---|---|---|
| CA | 2266763 | A1 | 10/1999 |
| GB | 1465661 | A | 2/1977 |

(Continued)

OTHER PUBLICATIONS

Peppers et al., J'nal Am Acad Derm'2018, pp. 83-98.*
Bissonnette et al "British Journal of Dermatology" 2012.*
Peppers et al., J'nal Am Acad Derm'2018, pp. 714-721.*
Aractingi S., "What's New in Dermatological Therapy?" Ann. Dermatol., 2012, 139(S5), pp. S223-S228.
Aulton, M.E., "Pharmaceutics—The Science of Dosage Form Design," Churchill Livingston, Edinburgh, 2nd edition, 2002, chapter 33, "Transdermal drug delivery", pp. 499-533.

(Continued)

*Primary Examiner* — Paul V Ward
(74) *Attorney, Agent, or Firm* — DLA Piper LLP (US)

(57) ABSTRACT

Topical compositions and methods for using topical compositions comprising tapinarof to treat mild to moderate atopic dermatitis or plaque psoriasis are described herein. Also described are clinical endpoints for treatment of subjects diagnosed with mild to moderate atopic dermatitis, wherein about 5% to about 35% of body surface area was affected, and Investigator Global Assessment (IGA) score was greater than or equal to 3. Also described are clinical endpoints for treatment of subjects diagnosed with chronic mild to moderate plaque psoriasis for greater than or equal to 6 months, wherein about 3% to about 20% of body surface area was affected, and Physician Global Assessment (PGA) score was greater than or equal to 2.

20 Claims, 23 Drawing Sheets

(56) References Cited

U.S. PATENT DOCUMENTS

| | | | |
|---|---|---|---|
| 2024/0285550 | A1 | 8/2024 | Sonti et al. |
| 2024/0315985 | A1 | 9/2024 | Rubenstein et al. |

FOREIGN PATENT DOCUMENTS

| | | | |
|---|---|---|---|
| JP | S58159410 | A | 9/1983 |
| JP | H1072330 | A | 3/1998 |
| WO | 1999059561 | A2 | 11/1999 |
| WO | 2001042231 | A2 | 6/2001 |
| WO | 2013000869 | A1 | 1/2013 |
| WO | 2020136650 | A1 | 7/2020 |
| WO | 2020194313 | A1 | 10/2020 |

OTHER PUBLICATIONS

Bissonnette et al. "Efficacy and Safety of Topical WBI-1001 in Patients with Mild to Moderate Psoriasis: Results from a Randomized Double-Blind Placebo-Controlled, Phase II Trial" 2012, J. European Academy of Dermatology and Venereology 26:1516-1521.

Bissonnette et al. "Efficacy and Safety of Topical WBI-1001 in Patients with Mild to Severe Atopic Dermatitis: Results from a 12-Week, Multicentre, Randomized, Placebo-Controlled Double-Blind Trial" 2012, British Association of Dermatologists 166:853-860.

Bissonnette et al. "Efficacy and Safety of Topical WBI-1001 in the Treatment of Atopic Dermatitis: Results From a Phase 2A, Randomized, Placebo-Controlled Clinical Trial" Apr. 2010, Reprinted in Archives of Dermatology 146 (4):446-449.

Charman et al. "The Patient-Oriented Eczema Measure Development and Initial Validation of a New Tool for Measuring Atopic Eczema Severity from the Patients' Perspective" Jul. 30, 2004, Archives of Dermatology 1-21.

Chiricozzi A., et al., "Effective Topical Agents and Emerging Perspectives in the Treatment of Psoriasis," Expert Rev. Dermatol., 2012, 7(3), pp. 283-293.

EPO Communication Notice of Opposition for European Patent No. EP3297605, Feb. 8, 2023.

EPO responsive communication to Notice of Opposition from the opponent; European Patent No. EP3297605—dated Aug. 9, 2023.

Feldman et al. "Psoriasis Assessment Tools In Clinical Trials" 2005, Ann Rheum Dis 64(Suppl II):5 Pages, Retrieved from the Internet: URL: http://ard.bmj.com on Apr. 8, 2016.

Gao et al. "Preparation of Chitosan Microspheres Loading of 3,5-dihydroxy-4-i-propylstilbene and In Vitro Release" Jan. 6, 2011, J . Polymer Research 18:1501-1508.

Gessner C. "Eczema—Sunflower oil helps to save steroid" Jun. 7, 2011, Medical Tribune 2 Pages, Retrieved from the URL: https://www.medical-tribune.de/medizin-und-forschung/artikel/neurodermitis-sonnenblumenoel-hilft-steroid-einsparen/.

Gilet et al. "Development and Psychometric Validation of the Reflective Evaluation of psoriasis Efficacy of Treatment and Severity (REFLETS) Questionnaire: a Common Measure of Plaque-Type Psoriasis Severity and Treatment Efficacy for Patients and Clinicians" 2015, J. European Academy of Dermatology and Venereology 29:498-506.

Hecht "What are the Fitzpatrick Skin Types?" Mar. 7, 2019, Healthline, retrieved from the internet: https://www.healthline.com/health/beauty-skin-care/fitzpatrick-skin-types 6 Pages.

Kelhala et al. "IL-17/Th17 Pathway is Activated in Acne Lesions" Aug. 25, 2014, PLoS One 9(8):14 Pages, Article e105238.

Lebwohl et al. "The Psoriasis Symptom Diary: Development and Content Validity Of A Novel Patient-Reported Outcome Instrument" 2014, International J. Dermatology 53:714-722.

Mathias et al. "Assessing Signs and Symptoms of Psoriasis From the Patient Perspective" Jun. 8-13, 2015, Poster Presented at the Conference: World Congress of Dermatology, Vancouver, Canada 1 Page.

Mitscher et al. "Aorphastilbol, An Antimicrobial Agent From Amorpha Nana" 1985, CA 103:119981, Phytochemistry 24(7):2 Pages.

Ney et al. "Anti-inflammatory Effects of Synthetic Effects of Synthetic Retinoids may be Related to their Immunomodulatory Action" 1987, Dermatologica. 175(1):93-99.

Nugent et al. "ITE, A Novel Endogenous Nontoxic Aryl Hydrocarbon Receptor Ligand, Efficiently Suppresses EAU and T-Cell-Mediated Immunity" 2013, Investigative Ophthalmology Visual Science, 54:7463-7469, DOI:10.1167/ ovs. 12-11479.

Rubenstein et al. "Secondary Efficacy Outcomes from a Phase 2b, Randomized Dose-Finding Study of Tapinarof Cream for the Treatment of Plaque Psoriasis" Oct. 2019, Journal of the American Academy of Dermatology, AB121.

Smith et al. "Tapinarof Is a Natural AhR Agonist that Resolves Skin Inflammation in Mice and Humans" Jun. 6, 2017, J. Investigative Dermatology 37:2110-2119.

Umar et al. "Outcomes Associated with Matching Patients' Treatment Preferences to Physicians' Recommendations: Study Methodology" BMC Health Services Research, Jan. 3, 2012, 12(1):1-10.

Webster et al. "Double-Blind Study of Topical WBI-1001 Cream on Patients with Psoriasis (WBI-1001-101)" 2009, clinicalTrials gov Identifier: NCT00830817 4 Pages.

Weinberg et al. "Advances in Psoriasis: A Multisystemic Guide", Cover and p. 223—[online], retrieved on Aug. 14, 2019 URL:https://www.amazon.com/Advances-Psoriasis-Multisystemic-Jeffrey-Weinberg/dp/B00RYSGGK4 3 Pages.

Zhang et al. "The Preparation of 3,5-Dihydroxy-4-Isopropylstilbene Nanoemulsion and In Vitro Release" 2011, International Journal of Nanomedicine 6:649-657.

Zhang et al. "Suppression of Experimental Autoimmune Uveoretinitis by Inducing Differentiation of Regulatory T Dells via Activation of Aryl Hydrocarbon Receptor" Apr. 2010, Investigative Ophthalmology Visual Science, 51 (4):2109-2117.

EPO Communication Reply to Appeal for European Patent No. 3297605 dated Jun. 17, 2025, 32 pages.

Gao et al. "Synthesis of Novel Drug Benvitimod" May 12, 2011, Advanced Materials Research, 236-238:2378-2382.

"Judgment Granting Request for Adverse Judgment after Institution of Trial" issued Mar. 7, 2025 in Inter Partes Review Proceedings No. IPR2024-00834 for U.S. Pat. No. 11,590,088, 4 pages total.

Petition for Inter Partes Review of U.S. Pat. No. 11,590,088 (IPR2024-00834) dated Apr. 23, 2024 (89 pages).

Declaration of Wieke H. Liem, M.D., F.A.A.D. dated Apr. 23, 2024 (172 pages).

Chinese Clinical Trial Register Registration No. ChiCTR-TRC-10000995, "Pharmacokinetics and Tolerability of Topically Applied Benvitimod Cream in Patients with Psoriasis", Registration Date Sep. 3, 2010 (6 pages).

Chinese Clinical Trial Register Registration No. ChiCTR-TRC-11001391, "Multicentre, Randomised, Double-Blind, Placebo Controlled Trial on Topically Applied Benvitimod Cream in Patients With Psoriasis", Registration Date Jun. 20, 2011 (6 pages).

Chinese Clinical Trial Register Registration No. ChiCTR-TRC-13003259, "Multi-centre, Randomised, Double-Blind, Placebo- and Comparator-Controlled Trial on Topically Applied Benvitimod Cream in Patients With Psoriasis", Registration Date Apr. 7, 2013 (8 pages).

Butler et al. "Natural product and natural product derived drugs in clinical trials", Natural Product Reports, 2014 (50 pages).

Declaration of Paul T. Sudhakar, MS, MBA dated Apr. 21, 2024 (65 pages).

Declaration of Sylvia D. Hall-Ellis, Ph.D. dated Apr. 23, 2024 (199 pages).

Extended European Search Report for EP 22756938.1 dated Dec. 6, 2024.

Gold et al. "A Phase 2b, Randomized Clinical Trial of Tapinarof Cream for the Treatment of Plaque psoriasis: Secondary Efficacy and patient-reported outcomes" May 21, 2020, Journal of the American Academy of Dermatology, 84(3):624-631.

Robbins et al. "Phase 2, randomized dose-finding study of tapinarof (GSK2894512 cream) for the treatment of plaque psoriasis" Oct. 26, 2018, Journal of the American Academy of Dermatology, 80(3):714-721.

(56) References Cited

OTHER PUBLICATIONS

"A Long-Term, Open-Label, Extension Study to Evaluate the Safety and Efficacy of Tapinarof Cream, 1% for the Treatment of Plaque Psoriasis in Adults" Dec. 16, 2019, Clinical Study Protocol, 74 pages.
"Dermavant Reports Positive Phase 3 Results for Tapinarof Cream in Adult Patients with Plaque Psoriasis" Aug. 26, 2020, 2 pages, Retrieved from the Internet: URL:https://dermavant.com/dermavant-reports-positive-phase-3-results-for-tapinarof-cream-in-adult-patients-with-plaque-psoriasis/.
Decision Granting Institution of Inter Partes Review for U.S. Pat. No. 11,590,088 (IPR2024-00834) dated Nov. 8, 2024, 75 Pages.
Decision revoking the European Patent (Art. 101(3)(b) EPC) for European Patent No. 3297605, Nov. 7, 2024, 33 pages.
Opponents' Reply to Submission of the Appellant Patent Proprietor for Opposition of European Patent No. EP3297605 dated Dec. 11, 2025.

* cited by examiner

USE OF TAPINAROF FOR THE TREATMENT OF ATOPIC DERMATITIS

CROSS REFERENCE TO RELATED APPLICATIONS

This application is a continuation of U.S. patent application Ser. No. 17/871,663 filed Jul. 22, 2022, which is a continuation of U.S. patent application Ser. No. 16/682,485 filed Nov. 13, 2019, now U.S. Pat. No. 11,497,718 issued Nov. 15, 2022, which claims the benefit of U.S. Provisional Application No. 62/760,704 filed Nov. 13, 2018 and U.S. Provisional Application No. 62/833,276 filed Apr. 12, 2019, and U.S. patent application Ser. No. 16/682,485 is a continuation-in-part of U.S. patent application Ser. No. 16/682,476 filed Nov. 13, 2019, abandoned, which claims the benefit of U.S. Provisional Application No. 62/760,692 filed Nov. 13, 2018 and U.S. Provisional Application No. 62/833,269 filed Apr. 12, 2019, each of which are hereby incorporated by reference in their entirety.

SUMMARY

Embodiments of the invention are directed to methods for treating atopic dermatitis in a subject comprising topically administering once a day to the subject in need thereof a topical composition containing about 0.5% to about 1.0% tapinarof, wherein one or more symptom of psoriasis is improved. In some embodiments, the atopic dermatitis is mild to moderate.

Embodiments of the invention are directed to methods for treating chronic plaque psoriasis in a subject comprising topically administering once a day to the subject in need thereof a topical composition containing about 0.5% to about 1.0% tapinarof, wherein one or more symptom of psoriasis is improved. In some embodiments, the chronic plaque psoriasis is mild to moderate.

BRIEF DESCRIPTION OF THE DRAWINGS

For a fuller understanding of the nature and advantages of the present invention, reference should be made to the following detailed description taken in connection with the accompanying drawings, in which.

DETAILED DESCRIPTION

Figure 1:
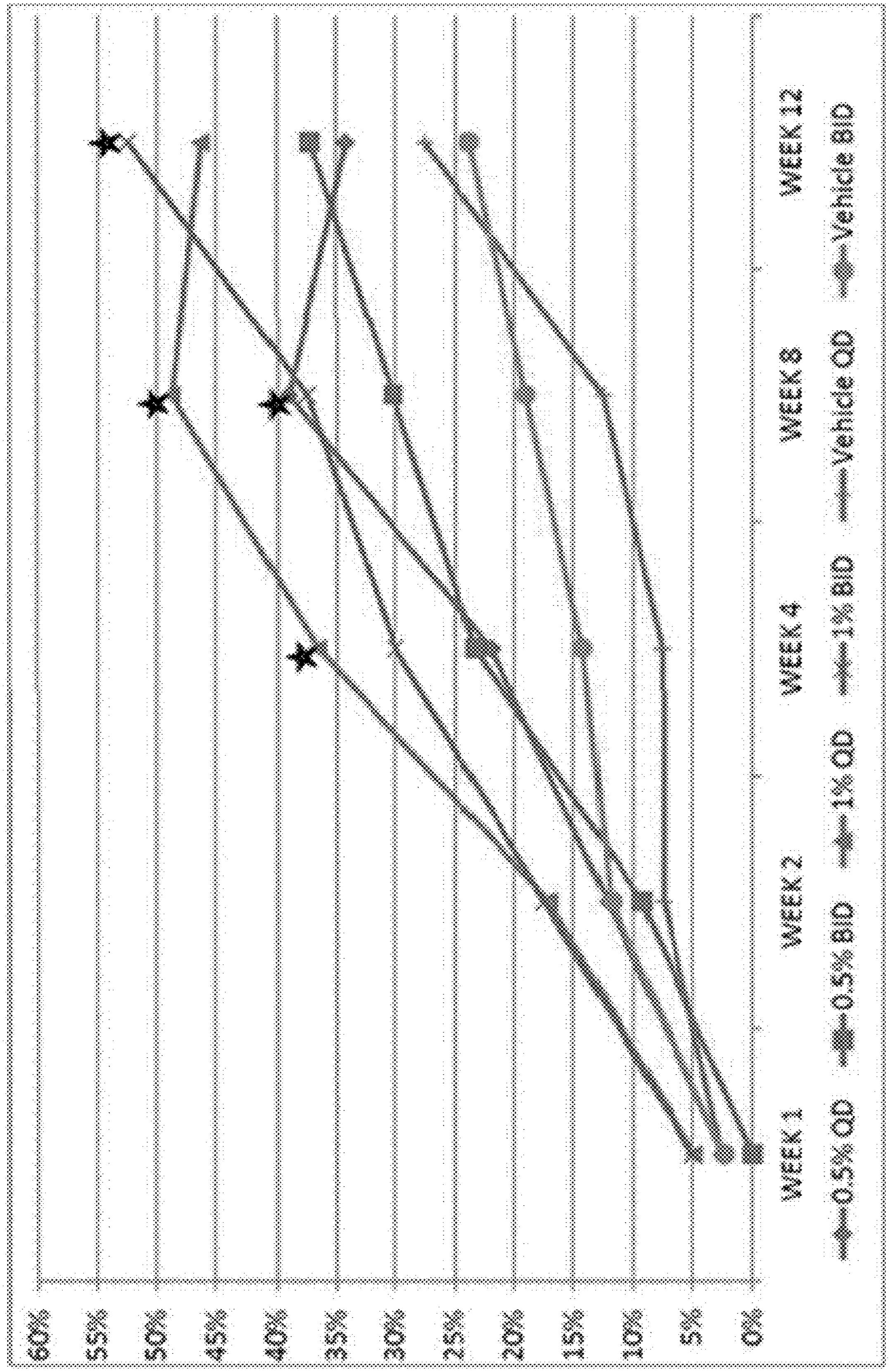
FIG. 1 demonstrates the proportion of patients who achieved an IGA score of clear or almost clear (0 or 1) and a minimum 2-grade improvement from baseline to each study visit using non-responder imputation.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 mg to 8 μmg is stated, it is intended that 2 mg, 3 mg, 4 mg, 5 mg, 6 mg, and 7 mg are also explicitly disclosed, as well as the range of values greater than or equal to 1 mg and the range of values less than or equal to 8 mg.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "subject" includes a single subject as well as two or more subjects; reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a topical composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance the texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government, or listed in the U.S. Pharmacopeia or other generally recognized pharmacopeia for use in mammals (e.g., animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient" and "subject" are interchangeable and may be taken to mean any human which may be treated with compounds of the present invention. In some embodiments, the patient or subject is an adult, adolescent, child or infant. In some embodiments, the patient or subject is an adolescent (i.e., 12-17 years old). In some embodiments, the patient or subject is younger than 2 years old. In some embodiments, the patient or subject is 18 years old or older. In some embodiments, the patient or subject is between the age of 18 and 75.

The term "treating" is used herein, for instance, in reference to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Atopic dermatitis (AD) (also called atopic eczema) is an intensely pruritic, chronic, relapsing, inflammatory skin disease. The characteristic signs and symptoms of AD include sensations of pruritus and burning, xerosis, erythematous papules and plaques, exudation, crusting, and lichenification. Quality of life is affected through sleep deprivation due to the intense and constant itching, as well as the stigma associated with having a visible skin disease. Up to 30% of children may be affected by AD at some point, and 1% to 3% of adults have AD. Currently there is no curative therapy. Stabilizing the disease and reducing the number and severity of flares are the primary goals of treatment. Topical treatments directed at skin inflammation are a key factor in disease management, as is symptomatic relief of itching. Although multiple topical treatment options are available, there still remains a need for a topical treatment that combines a high level of efficacy with an acceptable safety profile that permits application to a large body surface area (BSA) without restrictions on duration of treatment.

The cause of AD is multifactoral, with genetic and environmental factors, deficient skin barrier function, and impaired immune response. The inflammatory component is thought to be mediated primarily by the Th2 type T-cell activation pathway, although in chronic AD skin lesions, a shift towards a Th1-driven pathway has been described. Tapinarof inhibits the secretion of multiple pro-inflammatory cytokines and chemokines (e.g., Th2 cytokines and leukotriene B4), inhibits molecules involved in the adhesion and recruitment of cells involved in the pathogenesis of AD, and activates the aryl hydrocarbon receptor (AhR) and nuclear factor-erythroid 2-related factor-2 (Nrf2) anti-inflammatory pathways.

Psoriasis is a common, chronic relapsing inflammatory skin disease with recurrent episodes of prominently erythematous and scaly patches (plaques). Approximately 2 to 3% of the global population is affected by psoriasis; those affected are predominantly adults, who are most often diagnosed between the ages of 18 to 35 years. Psoriasis disrupts daily activities such as work and/or school attendance, interpersonal relationships, recreational activities, and intimacy, thereby significantly impacting sufferers' quality of life. Furthermore, psoriasis sufferers can also have co-morbidities such as arthritis, depression, inflammatory bowel disease, and cardiovascular (CV) diseases.

Up to 80% of patients have mild to moderate plaque-type psoriasis, which is generally managed with topical treatments. Topically-applied corticosteroids and Vitamin D analogs, alone or in combination, are the most commonly used products in the treatment of psoriasis. Vitamin D analogs are moderately efficacious as monotherapy, while application of topical corticosteroids—particularly the very potent ones—is restricted in terms of body areas that can be treated and the duration of use due to the well-known application site and systemic adverse drug reactions.

Although numerous topical treatment options are available, there still remains a need for a topical treatment that combines a high level of efficacy with an acceptable safety profile that permits application to a large body surface area (BSA) without restrictions on duration of treatment.

Tapinarof is a fully synthetic hydroxylated stilbene and new molecular entity that is a novel anti-inflammatory agent for the topical treatment of AD and plaque psoriasis.

Psoriatic skin lesions contain elevated numbers of activated T-cells, which have a key role in the pathogenesis of inflammatory diseases through the proliferation and secretion of pro-inflammatory cytokines. The drug likely mediates its effects via the aryl hydrocarbon receptor (AhR) agonist and nuclear factor erythroid 2-related factor 2 (Nrf2) because the pattern of pro-inflammatory mediators inhibited by tapinarof is different from that of corticosteroids, calcineurin inhibitors, vitamin D analogs, and other immunosuppressive agents commonly used to treat AD and psoriasis. Rather, the profile of biological responses elicited by tapinarof most closely matches that of the dual activation properties of coal tar, a common nonprescription treatment for psoriasis. Together, existing data identify tapinarof as a non-steroid, therapeutic AhR-modulating agent (TAMA), which is a unique mechanism of action compared with existing therapies.

Clinical studies of Tapinarof cream with up to 12 weeks of treatment were conducted using a different formulation. These studies suggested evidence of efficacy in treatment of AD and psoriasis, and also provide a preliminary understanding of potential adverse events (AEs) and the overall safety profile of the active compound.

It was surprisingly and unexpectedly found that the 1% tapinarof cream formulation applied topically once daily was just as effective as the 1% twice daily. This is surprising because both the 0.5% and 1% concentrations demonstrated an acceptable safety profile when applied once or twice daily but the 1% concentration was shown to be more effective than the 0.5% concentration, accordingly, one would have expected that a twice daily application would have been even more effective than a once daily application. A faster onset of action was observed with 1% dosing groups compared with the 0.5% dosing groups; fast onset of action is an important consideration for topical medications. A once daily application regimen may reduce systemic exposure as the atopic dermatitis is treated, thereby providing a better efficacy and safety profile for a drug intended for long-term use to treat a chronic condition. In addition, once daily application may improve treatment adherence compared to more frequent dosing administrations.

Compositions

Embodiments of the invention are directed to topical compositions comprising 3,5-Dihydroxy-4-isopropyl-trans-stilbene or a pharmaceutically acceptable salt thereof. Throughout this disclosure 3,5-Dihydroxy-4-isopropyl-trans-stilbene is referred to as tapinarof, and is also known as (E)-2-isopropyl-5-styrylbenzene-1,3 diol, with the empirical formula $C_{17}H_{18}O_2$, a molecular weight of 254.32, and the following structure:

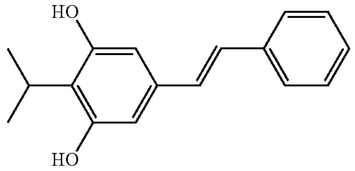 [SMILES: CC(C)c1c(O)cc(/C=C/c2ccccc2)cc1O]

In embodiments, the topical composition is an emulsion. In embodiments, the topical composition is an oil-in-water emulsion. In an embodiment, the topical composition of tapinarof or a pharmaceutically acceptable salt thereof, comprises an oil phase, and a water phase, creating an emulsion, and wherein the emulsion composition is homogenous. In an embodiment, tapinarof, or pharmaceutically acceptable salt thereof is solubilized in the oil phase of the emulsion composition. In embodiments, the oil phase is comprised of medium chain triglycerides, propylene glycol, non-ionic emulsifying wax, diethylene glycol monoethyl ether, polyoxyl stearyl ether-2, polysorbate 80, polyoxyl stearyl ether-20, benzoic acid, and butylated hydroxytoluene. In embodiments, the water phase is comprised of sodium citrate, edetate disodium, citric acid monohydrate, and water.

In certain embodiments described herein, the topical composition comprises about 0.50% to about 1.0% tapinarof, or a pharmaceutically acceptable salt thereof. In certain embodiments described herein, the topical composition comprises about 0.50% tapinarof, or a pharmaceutically acceptable salt thereof. In certain embodiments described herein, the topical composition comprises about 1.0% tapinarof, or a pharmaceutically acceptable salt thereof.

In certain embodiments described herein, the topical composition comprises about 50.00% to about 75.00% water, about 0.05% to about 0.50% sodium citrate, about 0.01% to about 2.00% citric acid, about 0.01% to about 1.00% disodium EDTA, about 5.00% to about 25.00% propylene glycol, about 0.10% to about 5.00% diethylene glycol monoethyl ether, about 0.01% to about 1.00% butylated hydroxytoluene, about 0.01% to about 1.00% benzoic acid, about 5.00% to about 10.00% emulsifying wax, about 5.00% to about 25.00% medium chain triglycerides (MCT), about 0.50% to about 5.00% polysorbate 80, about 0.50% to about 5.00% steareth 2, and about 0.50% to about 5.00% steareth 20.

In certain embodiments, the topical composition comprises 0.50% tapinarof, or a pharmaceutically acceptable salt thereof, 65.18% water, 0.19% sodium citrate, 0.08% citric acid, 0.10% disodium EDTA, 10.00% propylene glycol, 2.00% diethylene glycol monoethyl ether, 0.10% butylated hydroxytoluene, 0.25% benzoic acid, 7.20% emulsifying wax, 10.00% medium chain triglycerides (MCT), 1.50% polysorbate 80, 1.80% steareth 2, and 1.10% steareth 20.

In certain embodiments, the topical composition comprises 1.00% tapinarof, or a pharmaceutically acceptable salt thereof, 64.68% water, 0.19% sodium citrate, 0.08% citric acid, 0.10% disodium EDTA, 10.00% propylene glycol, 2.00% diethylene glycol monoethyl ether, 0.10% butylated hydroxytoluene, 0.25% benzoic acid, 7.20% emulsifying wax, 10.00% medium chain triglycerides (MCT), 1.50% polysorbate 80, 1.80% steareth 2, and 1.10% steareth 20. In another embodiment, the emulsifying wax is a proprietary blend known as "Polawax NF" (Registered Trademark) (Croda Inc, Edison, N.J., USA).

In embodiments, the topical composition may include pharmaceutically or cosmetically acceptable excipients, additives or other active agents as described herein.

In embodiments, the topical compositions may further include one or more pharmaceutical and/or cosmetically acceptable excipients selected from the group consisting of diluents, fillers, disintegrants, binders, lubricants, surfactants, hydrophobic vehicles, water soluble vehicles, emulsifiers, buffers, humectants, moisturizers, solubilizers, preservatives, colorants, plastizers, carriers, excipients, or combinations thereof. The person of ordinary skill in the art can refer to various pharmacologic references such as, for example, Modern Pharmaceutics, Banker & Rhodes, Marcel Dekker, Inc. (1979) and Goodman & Gilman's The Pharmaceutical Basis of Therapeutics, 6th Edition, MacMillan Publishing Co, New York (1980) for guidance in determining the amount of such components in the topical compositions and formulations of embodiments.

In embodiments, the topical compositions may include emollient or lubricating vehicles that help hydrate the skin can also be used. Examples of suitable bases or vehicles for preparing hydrating compositions for use with a subject skin are petrolatum, petrolatum plus volatile silicones, lanolin, cold cream (USP), and hydrophilic ointment (USP).

In embodiments, the topical compositions may include a second active agent. In embodiments, the second active agent is selected from dupilumab; crisaborole; calcineurin inhibitors, such as tacrolimus and pimecrolimus; antibiotics; hydrocortisone; corticosteroids, such as prednisone; antihistamines, such as cetirizine, fexofenadine, diphenhydramine; and combinations thereof. In embodiments, the second active agent is selected from apremilast (Otezla™); adalimumab; secukinumab; guselkumab; ixekizumab; etanercept; infliximab; ustekinumab; golimumab; apremilast; topical corticosteroids (TCS), such as prednisone; vitamin D; vitamin D derivatives, such as calcipotriene or calcitriol; combination of calcipotriene and betamethasone dipropionate (Enstilar™) anthralin; methotrexate; cyclosporine; vitamin A; vitamin A derivatives, such as retinoids, tazarotene, or acitretin; calcineurin inhibitors, such as tacrolimus and pimecrolimus; thioguanine; hydroxyurea; salicylic acid; coal tar; and combinations thereof.

In embodiments, the topical compositions may be formulated in any formulation suitable for topical administration, including, but not limited to, a solution, fluid, emulsion, suspension, solid, semi-solid, jelly, paste, gel, hydrogel, ointment, lotion, emulsion, cream, foam, mousse, liquid, spray, suspension, dispersion, powder, aerosol, or transdermal patch. Formulations described in U.S. Patent Publication Nos. 2016/0338973, 2018/0064656, and 2019/0144367 are incorporated herein by reference in their entirety.

In embodiments, the topical compositions described herein may be formulated as a liquid. Liquid dosage forms for topical administration may include diluents such as, for example, alcohols, glycols, oils, water, and the like. Such topical compositions may also include wetting agents or emulsifiers. In some embodiments, the topical compositions of embodiments may be formulated as oil-in-water or water-in-oil emulsion. A cream can be a water-in-oil (w/o) emulsion in which an aqueous phase is dispersed in an oil phase, or an oil-in-water (o/w) emulsion in which an oil is dispersed within an aqueous base. An ointment generally refers to a more viscous oil-in-water cream. Traditional ointment bases (i.e., carrier) include hydrocarbons (petrolatum, beeswax, etc.) vegetable oils, fatty alcohols (cholesterol, lanolin, wool alcohol, stearyl alcohol, etc.) or silicones. Insoluble solids such as starch, zinc oxide, calcium carbonate, or talc can also be used in ointments and creams. Gel forms of the topical compositions described above can be formed by the entrapment of large amounts of aqueous or aqueous-alcoholic liquids in a network of polymers or of colloidal solid particles. Such polymers or colloids (gelling or thickening agents) are typically present at concentrations of less than 10% w/w and include carboxymethyl cellulose, hydroxypropylmethyl cellulose, hydroxyethyl cellulose, methyl cellulose, sodium alginate, alginic acid, pectin, tragacanth, carrageen, agar, clays, aluminum silicate, carbomers, and the like.

In embodiments, the topical compositions described herein may be formulated as aerosols, in which the topical composition is dissolved in a propellant such as dichlorodifluoromethane, trichlorofluoromethane, dichlorotetrafluoroethane, carbon dioxide, or other suitable gas, and a cosolvent such ethanol, acetone, hexadecyl alcohol, and the like and combinations thereof.

In embodiments, the topical compositions can be in the form of hydrogels. Hydrogels are typically prepared by cross-linking various monomers and/or polymers to provide a three-dimensional polymer network. Non-limiting examples of polymers include, polyoxyethylene-polypropylene block copolymers, ionic poly saccharides, such as chitosan or sodium alginate, cellulose, and biodegradable polymers, such as poly-lactides (PLA) and poly-glycolides (PGA), butylene succinate (PBS), polyhydroxyalkanoate (PHA), polycaprolactone acid lactone (PCL), polyhydroxybutyrate (PHB), glycolic amyl (PHV), PHB and PHV copolymer (PHBV), and poly lactic acid (PLA)-polyethylene glycol (PEG) copolymers (PLEG).

In embodiments, the topical compositions disclosed herein can be in the form of transdermal patches. The transdermal patches can be in any conventional form such as, for example, a strip, a gauze, a film, and the like. Patch material may be nonwoven or woven (e.g., gauze dressing). Layers may also be laminated during processing. It may be nonocclusive or occlusive, but the latter is preferred for backing layers. The patch is preferably hermetically sealed for storage (e.g., foil packaging). The patch can be held onto the skin and components of the patch can be held together using various adhesives. For example, the transdermal patch can be in the form of a band-aid type device, or it may be packaged in a small metal or plastic "cup", which is strapped onto the appropriate site using an adhesive, tape, or an outer fabric or leather strap, similar to that worn as part of a watch. The entire patch may be disposable or may be refillable.

In embodiments, the topical compositions disclosed herein can be coated on bandages, mixed with bioadhesives, or included in dressings.

A wide variety of methods may be used for preparing the formulations described herein. Broadly speaking, the formulations may be prepared by combining together the components of the formulation, as described herein, at a temperature and for a time sufficient to provide a pharmaceutically acceptable composition. For example, in some embodiments, the topical compositions components may be dissolved, suspended, dispersed or otherwise mixed in a selected carrier or vehicle, at an effective concentration such that the condition to be treated is relieved or ameliorated.

Methods of Using Topical Compositions to Treat Atopic Dermatitis

Embodiments of the invention are directed to methods of treating atopic dermatitis in a subject comprising topically administering to the subject in need thereof a topical composition containing tapinarof as described herein, wherein one or more symptom of atopic dermatitis is improved. In some embodiments, the atopic dermatitis is mild to moderate.

Embodiments of the invention are directed to methods of treating atopic dermatitis in a subject comprising topically administering once a day to the subject in need thereof a topical composition containing about 0.5% tapinarof as described herein, wherein one or more symptom of atopic dermatitis is improved. In some embodiments, the atopic dermatitis is mild to moderate.

Embodiments of the invention are directed to methods of treating atopic dermatitis in a subject comprising topically administering once a day to the subject in need thereof a topical composition containing about 1.0% tapinarof as described herein, wherein one or more symptom of atopic dermatitis is improved. In some embodiments, the atopic dermatitis is mild to moderate.

Embodiments of the invention are directed to methods of treating atopic dermatitis in a subject comprising topically administering twice a day to the subject in need thereof a topical composition containing about 0.5% tapinarof as described herein, wherein one or more symptom of atopic dermatitis is improved. In some embodiments, the atopic dermatitis is mild to moderate.

Embodiments of the invention are directed to methods of treating atopic dermatitis in a subject comprising topically administering twice a day to the subject in need thereof a topical composition containing about 1.0% tapinarof as described herein, wherein one or more symptom of atopic dermatitis is improved. In some embodiments, the atopic dermatitis is mild to moderate.

In embodiments described herein, the topically administering of the topical composition includes application to the skin of the body, arms, legs, back, chest, buttocks, neck, scalp, fingernails, or toenails where the atopic dermatitis lesions are present (or "affected area"). The topically administering of the topical composition includes applying enough of the composition to completely cover each lesion with a thin layer. In embodiments described herein, administration of the topical composition requires that the subject lightly rub the cream into the skin until it is no longer visible.

In embodiments described herein, the subject is an adult or an adolescent. In embodiments described herein, the adolescents is age 12 to 17. In embodiments described herein, the subject is younger than 18 years of age. In embodiments described herein, the subject is younger than 2 years of age. In embodiments described herein, the subject is 18 years of age or older. In embodiments described herein, the subject is between the ages of 18 to 75 years old.

In embodiments described herein, the subject has been diagnosed with atopic dermatitis having a percent body surface area (BSA) affected of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35%. In preferred embodiments, the subject has been diagnosed with atopic dermatitis having a percent body surface area (BSA) affected of about 3% to about 20%. In embodiments described herein, body surface area (BSA) excludes the scalp, palms of the hands and soles of the feet.

In embodiments described herein, the subject has been diagnosed with atopic dermatitis having an Investigator Global Assessment (IGA) of about 3, or about 4. In embodiments described herein, the subject has been diagnosed with mild to moderate atopic dermatitis having an Investigator Global Assessment (IGA) of greater than or equal to 3.

In embodiments described herein, the topical composition is administered once daily for up to 24 weeks. In embodiments described herein, the topical composition is administered once daily for 24 weeks. In embodiments described herein, the topical composition is administered once daily for up to 12 weeks. In embodiments described herein, the topical composition is administered once daily for 12 weeks. In embodiments described herein, the topical composition is administered once daily for up to 8 weeks. In embodiments described herein, the topical composition is administered once daily for 8 weeks. In embodiments described herein, the topical composition is administered once daily for up to 6 weeks. In embodiments described herein, the topical composition is administered once daily for 6 weeks. In embodiments described herein, the topical composition is administered once daily for up to 4 weeks. In embodiments described herein, the topical composition is administered once daily for 4 weeks. In embodiments described herein, the topical composition is administered once daily until the atopic dermatitis is resolved.

In embodiments described herein, the topical composition is administered twice daily for up to 24 weeks. In embodiments described herein, the topical composition is administered twice daily for 24 weeks. In embodiments described herein, the topical composition is administered twice daily for up to 12 weeks. In embodiments described herein, the topical composition is administered twice daily for 12 weeks. In embodiments described herein, the topical composition is administered twice daily for up to 8 weeks. In embodiments described herein, the topical composition is administered twice daily for 8 weeks. In embodiments described herein, the topical composition is administered twice daily for up to 6 weeks. In embodiments described herein, the topical composition is administered twice daily for 6 weeks. In embodiments described herein, the topical composition is administered twice daily for up to 4 weeks. In embodiments described herein, the topical composition is administered twice daily for 4 weeks. In embodiments described herein, the topical composition is administered twice daily until the atopic dermatitis is resolved.

In embodiments described herein, the one or more symptom of atopic dermatitis is measured according to an assessment selected from Investigator Global Assessment (IGA) score, daily Itch/Pruritus numeric rating scale, Eczema Area and Severity Index (EASI), total severity score, percent body surface area (BSA) affected, sleep quality, dry/rough skin, red/discolored skin, flaky skin, visual analogue scale (VAS) for sleep, visual analogue scale (VAS) for itch, and patient reported outcomes.

In embodiments described herein, the Investigator's Global Assessment (IGA) is used for assessing the current state/severity of a subject's AD, also referred to as vIGA-AD™ (Validated Investigator Global Assessment for Atopic Dermatitis), a scale developed by Eli Lilly and Company and atopic dermatitis experts, including International Eczema Council advisors and Industry experts, for use in clinical trials. It uses a static 5-point morphological assessment of overall disease severity, as determined by the investigator, using the clinical characteristics of erythema, infiltration, papulation, oozing, and crusting as guidelines. In certain embodiments, the IGA is made daily, weekly, or monthly and without reference to previous scores. The scoring system ranges from 0 (=Clear) to 4 (=Severe). A score of 0 (Clear) has the following morphological description: no inflammatory signs of atopic dermatitis (no erythema, no induration/papulation, no lichenification, no oozing/crusting), and postinflammatory hyperpigmentation and/or hypopigmentation may be present. A score of 1 (Almost Clear) has the following morphological description: barely perceptible erythema, barely perceptible induration/papulation, and/or minimal lichenification, and no oozing or crusting. A score of 2 (Mild) has the following morphological description: slight but definite erythema (pink), slight but definite induration/papulation, and/or slight but definite lichenification, and no oozing or crusting. A score of 3 (Moderate) has the following morphological description: clearly perceptible erythema (dull red), clearly perceptible induration/papulation, and/or clearly perceptible lichenification, and oozing and crusting may be present. A score of 4 (Severe) has the following morphological description: marked erythema (deep or bright red), marked induration/papulation, and/or marked lichenification, disease is widespread in extent, and oozing or crusting may be present. In embodiments described herein, the subject's Investigator Global Assessment (IGA) score improved by about 1 grade, about 2 grades, about 3 grades, about 4 grades, or about 5 grades. In embodiments described herein, the subject's Investigator Global Assessment (IGA) score improved by about 2 grades. In embodiments described herein, the subject's Investigator Global Assessment (IGA) score improved to a score of about 0 or about 1. In embodiments described herein, the subject's Investigator Global Assessment (IGA) score improved to a score of about 1 or almost clear. In certain embodiments, the subject achieved a score of about 0 or about 1 by week 1, week 2, week 3, week 4, week 5, week 6, week 7, week 8, week 9, week 10, week 11, or week 12. In certain embodiments, the subject achieved a 2-grade improvement by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of PGA score after treatment has ended. In embodiments described herein, the subject has sustained improvement of PGA score about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of PGA score about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, administration of the topical composition to a subject having severe atopic dermatitis is effectively treated wherein the subject achieved a "Clear" or "Almost Clear" rating according to the PGA with at least a 2 point improvement. In embodiments described herein, administration of the topical composition to a subject having moderate atopic dermatitis is effectively treated wherein the subject achieved a "Clear" or "Almost Clear" rating according to the PGA with at least a 2 point improvement. In embodiments described herein, administration of the topical composition to a subject having mild atopic dermatitis is effectively treated wherein the subject achieved a "Clear" rating according to the PGA.

Pruritus is the most frequent symptom of AD and potentially has the greatest effect on quality of life. In embodiments described herein, the daily Itch/Pruritus numeric rating scale is subject-reported and obtained from the itch item on the Daily Sign and Symptom Severity Diary. In embodiments described herein, the subject's Itch/Pruritus numeric rating scale is improved by about 1 point, about 2 points, about 3 points, about 4 points, or about 5 points. In embodiments described herein, the subject's Itch/Pruritus numeric rating scale is improved by 3 points.

The assessment of the % BSA affected is an estimate of the percentage of total involved skin with atopic dermatitis. The extent of BSA affected by AD is a general indicator of disease severity. In embodiments described herein, one percent body surface area (1% BSA) is the equivalent of the total palmar surface of the palm plus 5 digits. The % BSA affected is calculated using the following regional body areas: Head and neck; Trunk, includes internal axillae and groin; Upper extremities, includes arms, external axillae, and hands; and Lower extremities, includes legs, buttocks, and feet. In embodiments described herein, body surface area (BSA) excludes the scalp, palms of the hands and soles of the feet. The % BSA assessment is utilized in the EASI. The % BSA affected by atopic dermatitis is evaluated from 0 to 100%. In embodiments described herein, the subject's percent body surface area (BSA) affected is decreased. In certain embodiments, the subject achieved a decrease in the % BSA affected by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of % BSA affected after treatment has ended. In embodiments described herein, the subject has sustained improvement of percent body surface area (BSA) affected about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of % BSA affected about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the Eczema Area and Severity Index (EASI) is measured using a scoring system for assessing the severity of AD that takes into account the overall severity of erythema, infiltration/papulation, excoriation, and lichenification, as well as the extent of BSA affected with AD. The 4 clinical signs are each graded on a 4-point scale (0 to 3) for each of the 4 specified body regions (head and neck, upper extremities, lower extremities, and trunk). The EASI is a static assessment made without reference to previous scores. In embodiments described herein, the subject's Eczema Area and Severity Index (EASI) is improved by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In embodiments described herein, the subject's Eczema Area and Severity Index (EASI) is improved by greater than or equal to 25%, greater than or equal to 50%, or greater than or equal to 75%. In embodiments described herein, the subject's Eczema Area and Severity Index (EASI) is improved by greater than or equal to 50%. In embodiments described herein, the subject's Eczema Area and Severity Index (EASI) is improved by greater than or equal to 75%. In certain embodiments, the subject achieved a greater than 50% improvement in EASI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In certain embodiments, the subject achieved a greater than 75% improvement in EASI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In certain embodiments, the subject achieved a greater than 90% improvement in EASI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of EASI after treatment has ended. In embodiments described herein, the subject has sustained improvement of EASI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of EASI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the total severity score (TSS) is determined by measuring a single target lesion measuring at least 3 cm at baseline and was representative of subject disease, but not located on hands, feet or genitalia. The single target lesion selected to assess efficacy in treating a discrete area rather than an overall average of all areas. For the single target lesion, the severity of erythema, induration/ papulation, lichenification, oozing/crusting, and scaling was assessed on a 4-point scale and TSS was calculated. The maximum score was 15, with higher scores indicating more severe disease. In embodiments described herein, the subject's total severity score improved by about 1 point, about 2 points, 3 points, about 4 points, about 5 points, about 6 points, about 7 points, about 8 points, about 9 points, about 10 points, about 11 points, about 12 points, about 13 points, about 14 points, or about 15 points. In certain embodiments, the subject achieved an improvement in total severity score by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of total severity score after treatment has ended. In embodiments described herein, the subject has sustained improvement of total severity score about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of total severity score about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, patient reported outcomes were measured using the Daily Sign and Symptom Severity Diary and the Expanded Patient-Oriented Eczema Measure (POEM).

In some embodiments, different quality of life scales are utilized to assess patient improvement through Patient Reported Outcome (PRO) measures. EQ-5D-5L is a five level scale to define general health levels, for example having no problems, having slight problems, having moderate problems, having severe problems and being unable to do/having extreme problems. Children's Dermatology Life Quality Index (CDLQI) includes physical symptoms, such as itching and sleep loss, as well as psychosocial questions regarding friendships, bullying, school performance, sports participation, and enjoyment of vacation. Dermatology Life Quality Index (DLQI) inquires about skin symptoms, feelings of embarrassment, and how skin disease has affected day-to-day activities, working and social life. Infant's Dermatology Quality of Life (IDQOL) includes questions regarding an infant or young child's difficulties with mood, sleep, bathing, dressing, play, mealtimes, other family activities, and treatment Dermatitis Family Impact (DFI) is designed to be completed by a caretaker of the child, usually a parent, and consists of 10 questions related to housework, food preparation and feeding, sleep, family leisure activity, shopping, expenditure, fatigue, emotional distress and relationships. The PROMIS Itch-Mood and Sleep Short Form 8a assesses mood and sleep related quality of life impairment from itch (pruritus) in adults (18+), it is universal rather than disease specific and assesses the impact of itch over the past 7 days and includes 18 items. In embodiments described herein, the subject score in one of more PRO, such as EQ-5D-5L, CDLQI, DLQI, IDQOL, DFI, and/or PROMIS Itch-Mood and Sleep improves.

In embodiments described herein, the self-administered Daily Sign and Symptom Severity Diary assesses the severity of 11 disease-related signs and symptoms: 1.) skin that is itchy, 2.) discolored, 3.) bleeding, 4.) oozing, 5.) cracked, 6.) scaly, 7.) flaky, 8.) dry/rough, 9.) painful, 10.) burning, and 11.) stinging. Response options are on an 11-point numeric rating scale (NRS) and range from 0 (Absent) to 10 (Worst Imaginable). In embodiments described herein, the recall period was the previous 24 hours. In embodiments described herein, the subject's assessment of itchy skin, red/discolored skin, bleeding, weeping or oozing skin, cracked skin, scaly skin, flaky skin, dry or rough skin, painful skin, burning skin, or burning skin, each improved by about 1 point, about 2 points, 3 points, about 4 points, about 5 points, about 6 points, about 7 points, about 8 points, about 9 points, about 10 points, or about 11 points. In certain embodiments, the subject reported an improvement on one or more symptoms assessed by the Daily Sign and Symptom Severity Diary by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of one or more symptoms assessed by the Daily Sign and Symptom Severity Diary after treatment has ended. In embodiments described herein, the subject has sustained improvement of one or more symptoms assessed by the Daily Sign and Symptom Severity Diary about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of one or more symptoms assessed by the Daily Sign and Symptom Severity Diary about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the subject assessed disease severity using the self-administered Expanded Patient-Oriented Eczema Measure (POEM). In embodiments described herein, the Expanded POEM assessed seven symptoms: 1.) skin that is itchy, 2.) bleeding, 3.) weeping/oozing, 4.) cracked, 5.) flaking, 6.) dry/rough, and 7.) disturbed sleep; measured using a 5-point scale of frequency of occurrence during the previous week. The 3 questions to assess sleep quality were directed to the frequency of waking at night difficulty falling asleep due to the atopic dermatitis. Individual responses were scored from 0 to 4. Improvement in sleep and improvement in itch were also measured using a visual analogue scale (VAS). In embodiments described herein, the subject's assessment of itchy skin, bleeding, weeping/oozing, cracked skin, flaking skin, dry/rough skin, and disturbed sleep each improved by about 1 point, about 2 points, 3 points, or about 4 points. In embodiments described herein, the subject's assessment of sleep quality is improved. In embodiments described herein, the subject's assessment of disturbed sleep improved. In certain embodiments, the subject reported an improvement on one or more symptoms assessed by POEM by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of one or more symptoms assessed by the POEM after treatment has ended. In embodiments described herein, the subject has sustained improvement of one or more symptoms assessed by the POEM about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of one or more symptoms assessed by the POEM about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the one or more symptoms improved by about 2 weeks, about 3 weeks, about 4 weeks, about 5 weeks, about 6 weeks, about 7 weeks, or about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after of administering the topical composition. In embodiments described herein, the one or more symptoms improved by about 2 weeks of administering the topical composition. In embodiments described herein, the one or more symptoms improved by about 4 weeks of administering the topical composition. In embodiments described herein, the one or more symptoms improved by about 8 weeks of administering the topical composition. In embodiments described herein, the one or more symptoms improved by about 12 weeks of administering the topical composition.

In some embodiments, it was surprisingly found that the topical composition may produce long lasting effects on the skin and may modify the long-term course of atopic dermatitis. Specifically, in certain embodiments, the improvement of the symptoms seen during administration of the topical composition may be maintained long after the final administration of the topical composition. In embodiments described herein, the one or more symptoms remain improved about 1 week, about 2 weeks, about 3 weeks, about 4 weeks, about 5 weeks, about 6 weeks, about 12 weeks, about 13 weeks, about 14 weeks, about 15 weeks, about 16 weeks, about 17 weeks, about 18 weeks, about 19 weeks, about 20 weeks, or up to 52 weeks after administration of the composition has ceased. In embodiments described herein, the one or more symptoms remain improved about 2 weeks after administration of the topical composition has ceased. In embodiments described herein, the one or more symptoms remain improved about 3 weeks after administration of the topical composition has ceased. In embodiments described herein, the one or more symptoms remain improved about 4 weeks after administration of the topical composition has ceased. In embodiments described herein, the one or more symptoms remain improved about 8 weeks after administration of the topical composition has ceased. In embodiments described herein, the one or more symptoms remain improved about 12 weeks after administration of the topical composition has ceased. In embodiments described herein, the one or more symptoms remain improved about 16 weeks after administration of the topical composition has ceased. In embodiments described herein, the one or more symptoms remain improved about 20 weeks after administration of the topical composition has ceased.

It was surprisingly found that the topical composition may produce long lasting effects on the skin and may modify the long-term course of atopic dermatitis. Specifically, in certain embodiments, the symptoms do not worsen after the final administration of the topical composition. In embodiments described herein, the one or more symptoms do not worsen about 1 week, about 2 weeks, about 3 weeks, about 4 weeks, about 5 weeks, about 6 weeks, about 12 weeks, about 13 weeks, about 14 weeks, about 15 weeks, about 16 weeks, about 17 weeks, about 18 weeks, about 19 weeks, about 20 weeks, or up to 52 weeks after administration of the topical composition has ceased. In embodiments described herein, the one or more symptoms do not worsen about 2 weeks after administration of the topical composition has ceased. In embodiments described herein, the one or more symptoms do not worsen about 3 weeks after administration of the topical composition has ceased. In embodiments described herein, the one or more symptoms do not worsen about 4 weeks after administration of the topical composition has ceased. In embodiments described herein, the one or more symptoms do not worsen about 8 weeks after administration of the topical composition has ceased. In embodiments described herein, the one or more symptoms do not worsen about 12 weeks after administration of the topical composition has ceased. In embodiments described herein, the one or more symptoms do not worsen about 16 weeks after administration of the topical composition has ceased. In embodiments described herein, the one or more symptoms do not worsen about 20 weeks after administration of the topical composition has ceased.

In embodiments described herein, the topical composition exhibits low systemic absorption following topical application. In embodiments described herein, the topical composition exhibits no accumulation with repeat dosing. Systemic absorption of tapinarof is measured in plasma. In embodiments described herein, plasma concentration of tapinarof is below the limit of detection (LOD) when measured at 1, 2, 4, 6, 8 and 24 hours following once daily application of the topical composition described herein. In embodiments described herein, plasma concentration of tapinarof is below the limit of detection (LOD) when measured at 1, 2, 4, 6, 8 and 24 hours following twice daily application of the topical composition described herein. In some embodiments, the mean $AUC_{[0-24]}$ is about 23.4 to about 2.2 h*ng/mL. In some embodiments, the mean $AUC_{[0-24]}$ is about 10.5 to about 1.5 h*ng/mL.

In embodiments described herein, the topical composition is non-stinging.

In embodiments described herein, the topical composition is more effective than pimecrolimus (Elidel™), tacrolimus (Protopic™), crisaborole (Eucrisa™), or desonide (Verdeso™ or Desonate™).

In embodiments described herein, the topical composition is administered in an initial dosing regimen followed by a maintenance dosing regimen. In embodiments described herein, the initial dosing regimen is about 1 week to about 24 weeks in duration. In embodiments described herein, the maintenance dosing regimen is about 1 week to about 24 weeks in duration. In embodiments described herein, the topical composition administered in the initial dosing regimen contains 1% tapinarof. In embodiments described herein, the topical composition administered in the maintenance dosing regimen contains 0.5% tapinarof.

In embodiments, the method may include the co-administration of additives, other second active agents or enzymes as described herein. In embodiments, co-administration may be at the same time, substantially the same time, before or after administration of the topical compositions described herein.

In embodiments, the additives may be selected from the group consisting of vitamins, cosmetic peptides, oil control agents, sensation modifying agents, skin lightening agents, hydrating compositions, a sunblock agent, a compound that absorbs or reflects UV photons, other skin care agents, a second active agent and combinations thereof, as described herein.

In some embodiments, administration of the composition is by topical application, transdermal, percutaneous, or microneedle injection.

In embodiments, the composition is administered by microneedle injection. Microneedle is a hollow needle having an exposed height of between about 0 and 1 mm and a total length of between about 0.3 mm to about 2.5 mm. Preferably, the microneedle is a hollow needle having a length of less than about 2.5 mm. Most preferably, the microneedle is a hollow needle having a length of less than about 1.7 mm. The composition comprising therapeutic cells and extracellular matrix component are delivered into the skin to a depth of at least about 0.3 mm and no more than about 2.5 mm by the microneedle.

In some embodiments, the topical composition can be applied to the skin one, two, three, four, five or more times each day, and applying can be carried out for a period of at least 1 month, 2 months, 3 months, 4 months, 6 months, 8 months or 12 months.

In such embodiments, the topical composition can be applied to the skin one, two, three, four, five or more times each day, and applying can be carried out for a period of at least 1 month, 2 months, 3 months, 4 months, 6 months, 8 months or 12 months.

In some embodiments, the topical composition may be administered once, as needed, once daily, twice daily, three times a day, once a week, twice a week, every other week, every other day, or the like for one or more dosing cycles. A dosing cycle may include administration for about 1 week, about 2 weeks, about 3 weeks, about 4 weeks, about 5 weeks, about 6 weeks, about 7 weeks, about 8 weeks, about 9 weeks, or about 10 weeks. After this cycle, a subsequent cycle may begin approximately 1, 2, 3, 4, 5, 6, 7, 8, 9, 10, 11, or 12 weeks later. The treatment regime may include 1, 2, 3, 4, 5, or 6 cycles, each cycle being spaced apart by approximately 1, 2, 3, 4, 5, 6, 7, 8, 9, 10, 11, or 12 weeks.

Methods of Using Topical Compositions to Treat Psoriasis

Embodiments of the invention are directed to methods of treating chronic plaque psoriasis in a subject comprising topically administering to the subject in need thereof a topical composition containing tapinarof as described herein, wherein one or more symptom of psoriasis is improved. In some embodiments, the chronic plaque psoriasis is mild to moderate.

Embodiments of the invention are directed to methods of treating chronic plaque psoriasis in a subject comprising topically administering once a day to the subject in need thereof a topical composition containing about 0.5% tapinarof as described herein, wherein one or more symptom of psoriasis is improved. In some embodiments, the chronic plaque psoriasis is mild to moderate.

Embodiments of the invention are directed to methods of treating chronic plaque psoriasis in a subject comprising topically administering once a day to the subject in need thereof a topical composition containing about 1.0% tapinarof as described herein, wherein one or more symptom of psoriasis is improved. In some embodiments, the chronic plaque psoriasis is mild to moderate.

Embodiments of the invention are directed to methods of treating chronic plaque psoriasis in a subject comprising topically administering twice a day to the subject in need thereof a topical composition containing about 0.5% tapinarof as described herein, wherein one or more symptom of psoriasis is improved. In some embodiments, the chronic plaque psoriasis is mild to moderate.

Embodiments of the invention are directed to methods of treating chronic plaque psoriasis in a subject comprising topically administering twice a day to the subject in need thereof a topical composition containing about 1.0% tapinarof as described herein, wherein one or more symptom of psoriasis is improved. In some embodiments, the chronic plaque psoriasis is mild to moderate.

Embodiments of the invention are directed to methods of treating chronic plaque psoriasis in a subject comprising topically administering to the subject in need thereof a topical composition containing tapinarof as described herein, wherein skin type does not affect the efficacy of the treatment. In some embodiments, the chronic plaque psoriasis is mild to moderate. In some embodiments, the skin type is measured using the Fitzpatrick scale, wherein the subject's skin type is selected from the group consisting of Fitzpatrick skin type I, Fitzpatrick skin type II, Fitzpatrick skin type III, Fitzpatrick skin type IV, Fitzpatrick skin type V, and Fitzpatrick skin type VI. Fitzpatrick scale is a numerical classification schema for human skin color. The following list shows the six categories of the Fitzpatrick scale: Type I—always burns, never tans (palest, freckles); Type II—usually burns, tans minimally; Type III—sometimes mild burn, tans uniformly; Type IV—burns minimally, always tans well (moderate brown); Type V—very rarely burns, tans very easily (dark brown); or Type VI—never burns (deeply pigmented dark brown to darkest brown). In some embodiments, a method of treating chronic plaque psoriasis in a subject having Fitzpatrick skin type I comprising topically administering to the subject in need thereof a topical composition containing tapinarof as described herein. In some embodiments, a method of treating chronic plaque psoriasis in a subject having Fitzpatrick skin type II comprising topically administering to the subject in need thereof a topical composition containing tapinarof as described herein. In some embodiments, a method of treating chronic plaque psoriasis in a subject having Fitzpatrick skin type III comprising topically administering to the subject in need thereof a topical composition containing tapinarof as described herein. In some embodiments, a method of treating chronic plaque psoriasis in a subject having Fitzpatrick skin type IV comprising topically administering to the subject in need thereof a topical composition containing tapinarof as described herein. In some embodiments, a method of treating chronic plaque psoriasis in a subject having Fitzpatrick skin type V comprising topically administering to the subject in need thereof a topical composition containing tapinarof as described herein. In some embodiments, a method of treating chronic plaque psoriasis in a subject having Fitzpatrick skin type VI comprising topically administering to the subject in need thereof a topical composition containing tapinarof as described herein.

In embodiments described herein, the topically administering of the topical composition includes application to the skin of the body, arms, legs, back, chest, buttocks, neck, scalp, fingernails, or toenails where the plaque psoriasis lesions are present (or "affected area"). The topically administering of the topical composition includes applying enough of the topical composition to completely cover each lesion with a thin layer. In embodiments described herein, administration of the topical composition requires that the subject lightly rub the cream into the skin until it is no longer visible.

In embodiments described herein, the subject has been diagnosed with chronic plaque psoriasis and has had stable disease for at least 6 months, at least 7 months, at least 8 months, at least 9 months, at least 10 months, at least 11 months, or at least 12 months. In preferred embodiments, the subject has been diagnosed with chronic mild to moderate plaque psoriasis and has had stable disease for at least 6 months.

In embodiments described herein, the subject is younger than 18 years of age. In embodiments described herein, the subject is 18 years of age or older. In embodiments described herein, the subject is between the ages of 18 to 75 years old.

In embodiments described herein, the subject has been diagnosed with chronic plaque psoriasis having a percent body surface area (BSA) affected of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35%. In preferred embodiments, the subject has been diagnosed with chronic plaque psoriasis having a percent body surface area (BSA) affected of about 3% to about 20%. In embodiments described herein, body surface area (BSA) excludes the scalp, palms of the hands and soles of the feet.

In embodiments described herein, the subject has been diagnosed with chronic plaque psoriasis having a Physician Global Assessment (PGA) score of about 2, about 3, or about 4. In embodiments described herein, the subject has been diagnosed with chronic mild to moderate plaque psoriasis having a Physician Global Assessment (PGA) score of greater than or equal to 2. A PGA score of 2 is a diagnosis of mild plaque psoriasis. A PGA score of 3 is a diagnosis of moderate plaque psoriasis. A PGA score of 4 is a diagnosis of severe plaque psoriasis.

In embodiments described herein, the topical composition is administered once daily for up to 24 weeks. In embodiments described herein, the topical composition is administered once daily for 24 weeks. In embodiments described herein, the topical composition is administered once daily for up to 12 weeks. In embodiments described herein, the topical composition is administered once daily for 12 weeks. In embodiments described herein, the topical composition is administered once daily for up to 8 weeks. In embodiments described herein, the topical composition is administered once daily for 8 weeks. In embodiments described herein, the topical composition is administered once daily for up to 6 weeks. In embodiments described herein, the topical composition is administered once daily for 6 weeks. In embodiments described herein, the topical composition is administered once daily for up to 4 weeks. In embodiments described herein, the topical composition is administered once daily for 4 weeks. In embodiments described herein, the topical composition is administered once daily until the chronic plaque psoriasis is resolved.

In embodiments described herein, the topical composition is administered twice daily for up to 24 weeks. In embodiments described herein, the topical composition is administered twice daily for 24 weeks. In embodiments described herein, the topical composition is administered twice daily for up to 12 weeks. In embodiments described herein, the topical composition is administered twice daily for 12 weeks. In embodiments described herein, the topical composition is administered twice daily for up to 8 weeks. In embodiments described herein, the topical composition is administered twice daily for 8 weeks. In embodiments described herein, the topical composition is administered twice daily for up to 6 weeks. In embodiments described herein, the topical composition is administered twice daily for 6 weeks. In embodiments described herein, the topical composition is administered twice daily for up to 4 weeks. In embodiments described herein, the topical composition is administered twice daily for 4 weeks. In embodiments described herein, the topical composition is administered twice daily until the chronic plaque psoriasis is resolved.

In embodiments described herein, the topical composition comprising tapinarof is administered before the administration of apremilast (Otezla™).

In embodiments described herein, the one or more symptom of chronic psoriasis is measured according to an assessment selected from Physician Global Assessment (PGA) score, Psoriasis Area and Severity Index (PASI), target lesion grading, Itch/Pruritus numeric rating scale (NRS), percent body surface area (BSA) affected, Psoriasis Symptom Diary (PSD), Dermatology Quality of Life Index (DLQI), or SF-36 questionnaire.

In embodiments described herein, the Physician Global Assessment (PGA) is used to assess the current state/severity of a subject's psoriasis. It is a static 5-point morphological assessment of overall disease severity, as determined by the investigator, using the clinical characteristics of erythema, plaque thickness, and scaling as guidelines. In certain embodiments, the PGA is assessed daily, weekly, or monthly and without reference to previous scores. The scoring system includes: Score of 0 represents clear skin with no signs of psoriasis, postinflammatory hyperpigmentation may be present; Score of 1 represents almost clear skin with no thickening, normal to pink coloration, no to minimal focal scaling; Score of 2 represents mild psoriasis with just detectable to mild thickening, pink to light red coloration, predominantly fine scaling; Score of 3 represents moderate psoriasis with clearly distinguishable to moderate thickening, dull to bright red, clearly distinguishable erythema, moderate scaling; and Score of 4 represents severe psoriasis with severe thickening with hard edges, bright to deep dark red coloration, severe/coarse scaling covering almost all or all lesions. In embodiments described herein, the subject's Physician Global Assessment (PGA) score improved by about 1 grade, about 2 grades, about 3 grades, about 4 grades, or about 5 grades. In embodiments described herein, the subject's Physician Global Assessment (PGA) score improved by about 2 grades. In embodiments described herein, the subject's Physician Global Assessment (PGA) score improved to a score of about 0 or clear. In embodiments described herein, the subject's Physician Global Assessment (PGA) score improved to a score of about 1 or almost clear. In certain embodiments, the subject achieved a score of about 0 or about 1 by week 1, week 2, week 3, week 4, week 5, week 6, week 7, week 8, week 9, week 10, week 11, or week 12. In certain embodiments, the subject achieved a 2-grade improvement by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of PGA score after treatment has ended. In embodiments described herein, the subject has sustained improvement of PGA score about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of PGA score about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, administration of the topical composition to a subject having severe plaque psoriasis is effectively treated wherein the subject achieved a “Clear” or “Almost Clear” rating according to the PGA with at least a 2 point improvement. In embodiments described herein, administration of the topical composition to a subject having moderate plaque psoriasis is effectively treated wherein the subject achieved a “Clear” or “Almost Clear” rating according to the PGA with at least a 2 point improvement. In embodiments described herein, administration of the topical composition to a subject having mild plaque psoriasis is effectively treated wherein the subject achieved a “Clear” rating according to the PGA.

The assessment of the % BSA affected is an estimate of the percentage of total involved skin with psoriasis. The extent of BSA affected by psoriasis is a general indicator of disease severity. In embodiments described herein, one percent body surface area (1% BSA) is the equivalent of the total palmar surface of the palm plus 5 digits. The % BSA affected is calculated using the following regional body areas: Head and neck; Trunk, includes internal axillae and groin; Upper extremities, includes arms, external axillae, and hands; and Lower extremities, includes legs, buttocks, and feet. In embodiments described herein, body surface area (BSA) excludes the scalp, palms of the hands and soles of the feet. The % BSA assessment is utilized in the PASI. The % BSA affected by psoriasis is evaluated from 0 to 100%. In embodiments described herein, the subject's percent body surface area (BSA) affected is decreased. In certain embodiments, the subject achieved a decrease in the % BSA affected by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of % BSA affected after treatment has ended. In embodiments described herein, the subject has sustained improvement of percent body surface area (BSA) affected about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of % BSA affected about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the Psoriasis Area and Severity Index (PASI) is used to assess the severity of psoriasis that takes into account the overall severity of erythema (redness), thickness (induration), and scale (desquamation), as well as the extent of BSA affected with psoriasis. The 3 clinical signs are each graded on a 5 point scale (0 to 4) and the % BSA affected is scored on a 7-point scale (0 to 6) for each of the 4 specified body regions (head, upper extremities, trunk, and lower extremities). The individual scores are multiplied by a weighted factor for each body region; the sum of these scores gives the overall PASI score. Higher scores indicate more severe disease. PASI is a static assessment made without reference to previous scores. In embodiments described herein, the subject's Psoriasis Area and Severity Index (PASI) is improved by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In embodiments described herein, the subject's Psoriasis Area and Severity Index (PASI) is improved by greater than or equal to 25%, greater than or equal to 50%, greater than or equal to 75%, or greater than or equal to 90%. In embodiments described herein, the subject's Psoriasis Area and Severity Index (PASI) is improved by greater than or equal to 50%. In embodiments described herein, the subject's Psoriasis Area and Severity Index (PASI) is improved by greater than or equal to 75%. In embodiments described herein, the subject's Psoriasis Area and Severity Index (PASI) is improved by greater than or equal to 90%. In certain embodiments, the subject achieved a greater than 50% improvement in PASI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In certain embodiments, the subject achieved a greater than 75% improvement in PASI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In certain embodiments, the subject achieved a greater than 90% improvement in PASI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of PASI after treatment has ended. In embodiments described herein, the subject has sustained improvement of PASI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of PASI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the target lesion grading is determined by measuring a single target lesion at baseline to assess efficacy in treating a discrete area rather than an overall average of all areas. For that single target lesion, the severity of erythema, scaling, and plaque thickness is assessed on a 5-point scale ranging from 0 (=none) to 4 (=severe). The maximum score was 15, with higher scores indicating more severe disease. In embodiments described herein, the subject's target lesion grading improved by about 1 point, about 2 points, 3 points, about 4 points, about 5 points, about 6 points, about 7 points, about 8 points, about 9 points, about 10 points, about 11 points, about 12 points, about 13 points, about 14 points, or about 15 points. In certain embodiments, the subject achieved an improvement in target lesion grading by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of target lesion grading after treatment has ended. In embodiments described herein, the subject has sustained improvement of target lesion grading about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of target lesion grading about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the daily Itch/Pruritus severity is subject-reported and obtained as a numeric rating scale (NRS) from the itch item on the Psoriasis Symptom Diary (PSD). In embodiments described herein, the subject's Itch/Pruritus severity is improved by about 1 point, about 2 points, 3 points, about 4 points, or about 5 points. In embodiments described herein, the subject's Itch/Pruritus severity is improved by 3 points. In certain embodiments, the subject achieved an improvement in daily Itch/Pruritus numeric rating scale (NRS) by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of Itch/Pruritus severity after treatment has ended. In embodiments described herein, the subject has sustained improvement of Itch/Pruritus severity about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of Itch/Pruritus severity about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, patient reported outcomes were measured using the Psoriasis Symptom Diary (PSD) which assesses daily self-reports of psoriasis symptoms and the functional impact related to the underlying pathophysiology of the disease. Questions asked about how severe and how bothersome various symptoms were to the subject. The symptoms assessed include 1) severity of flaky skin, 2) bother of flaky skin, 3) severity of dry skin, 4) bother of dry skin, 5) severity of bleeding, 6) bother of bleeding, 7) severity of itching, 8) bother of itching, 9) stinging, 10) burning, 11) pain from skin cracking, 12) psoriasis-related pain, 13) scaling, 14) noticeability of color, 15) need to hide skin, 16) avoidance of activities, and 17) overall embarrassment. Each item was rated using an 11-point numeric rating scale (NRS) and range from 0 (Absent) to 10 (Worst Imaginable). In embodiments described herein, the recall period was the previous 24 hours. In embodiments described herein, the subject's assessment of flaky skin, bother of flaky skin, severity of dry skin, bother of dry skin, severity of bleeding, bother of bleeding, severity of itching, bother of itching, stinging, burning, pain from skin cracking, psoriasis-related pain, scaling, noticeability of color, need to hide skin, avoidance of activities, and overall embarrassment, each improved by about 1 point, about 2 points, about 3 points, about 4 points, about 5 points, about 6 points, about 7 points, about 8 points, about 9 points, about 10 points, or about 11 points. In certain embodiments, the subject reported an improvement on one or more symptoms assessed by the PSD by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement of one or more symptoms assessed by the PSD after treatment has ended. In embodiments described herein, the subject has sustained improvement of one or more symptoms assessed by the PSD about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of one or more symptoms assessed by the PSD about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, subjects record changes using the Dermatology Quality of Life Index (DLQI) questionnaire. The DLQI is a simple dermatology-specific 10 question validated questionnaire to assess the impact of the disease on a subject's quality of life. The DLQI has become an important outcome measure in dermatology clinical trials and is the most frequently used instrument in studies of randomized controlled trials in dermatology. The DLQI can be analyzed as a total score (where a higher score indicates greater impairment in quality of life) and can also be scored for the following dimensions: Symptoms and Feelings (items 1 and 2), Daily Activities (items 3 and 4), Leisure (items 5 and 6), Work and School (item 7), Personal Relationships (items 8 and 9), and Treatment (item 10). In certain embodiments, the subject reported an improvement on the impact of one or more daily activities assessed by the DLQI by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In embodiments described herein, the subject has sustained improvement on the impact of one or more daily activities assessed by the DLQI after treatment has ended. In embodiments described herein, the subject has sustained improvement of one or more daily activities assessed by the DLQI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. IV. In embodiments described herein, the subject does not experience worsening of one or more daily activities assessed by the DLQI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, subjects self-administer the 36 Item Short Form Survey (SF-36). The SF-36 is a questionnaire about physical functioning; bodily pain; role limitations due to physical health or personal or emotional problems; emotional well-being; social functioning; energy/fatigue; general health perceptions; and perceived change in health. Eight domain scores and 2 summary component (physical and mental) scores can be calculated; higher scores represent better health status. In certain embodiments, the subject reported an improvement in the physical component score assessed by the SF-36 questionnaire by week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, or week 24. In certain embodiments, the subject reported an improvement in the mental component score assessed by the SF-36 questionnaire by week 1, week 2, week 3, week 4, week 5, week 6, week 7, week 8, week 9, week 10, week 11, week 11, week 12, week 13, week 14, week 15, week 16, week 17, week 18, week 19, week 20, week 21, week 22, week 23, or week 24. In embodiments described herein, the subject has sustained improvement in the physical component score and/or the mental component score assessed by the SF-36 questionnaire after treatment has ended. In embodiments described herein, the subject has sustained improvement in in the physical component score and/or the mental component score assessed by the SF-36 questionnaire about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of the physical component score and/or the mental component score assessed by the SF-36 questionnaire about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the one or more symptoms improved by about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after administering the topical composition. In embodiments described herein, the one or more symptoms improved by about 2 weeks of administering the topical composition. In embodiments described herein, the one or more symptoms improved by about 4 weeks of administering the topical composition. In embodiments described herein, the one or more symptoms improved by about 8 weeks of administering the topical composition. In embodiments described herein, the one or more symptoms improved by about 12 weeks of administering the topical composition.

In some embodiments, it was surprisingly found that the topical composition may produce long lasting effects on the skin and may modify the long-term course of chronic plaque psoriasis. Specifically, in certain embodiments, the improvement of the symptoms seen during administration of the topical composition may be maintained long after the final administration of the topical composition. In embodiments described herein, the one or more symptoms remain improved about 1 week, about 2 weeks, about 3 weeks, about 4 weeks, about 5 weeks, about 6 weeks, about 12 weeks, about 13 weeks, about 14 weeks, about 15 weeks, about 16 weeks, about 17 weeks, about 18 weeks, about 19 weeks, about 20 weeks, or up to 52 weeks after administration of the topical composition has ceased. In embodiments described herein, the one or more symptoms remain improved about 2 weeks after administration of the topical composition has ceased. In embodiments described herein, the one or more symptoms remain improved about 3 weeks after administration of the topical composition has ceased. In embodiments described herein, the one or more symptoms remain improved about 4 weeks after administration of the topical composition has ceased. In embodiments described herein, the one or more symptoms remain improved about 8 weeks after administration of the topical composition has ceased. In embodiments described herein, the one or more symptoms remain improved about 12 weeks after administration of the topical composition has ceased. In embodiments described herein, the one or more symptoms remain improved about 16 weeks after administration of the topical composition has ceased. In embodiments described herein, the one or more symptoms remain improved about 20 weeks after administration of the topical composition has ceased.

It was surprisingly found that the topical composition may produce long lasting effects on the skin and may modify the long-term course of chronic plaque psoriasis. Specifically, in certain embodiments, the symptoms do not worsen after the final administration of the topical composition. In embodiments described herein, the one or more symptoms do not worsen about 1 week, about 2 weeks, about 3 weeks, about 4 weeks, about 5 weeks, about 6 weeks, about 12 weeks, about 13 weeks, about 14 weeks, about 15 weeks, about 16 weeks, about 17 weeks, about 18 weeks, about 19 weeks, about 20 weeks, or up to 52 weeks after administration of the topical composition has ceased. In embodiments described herein, the one or more symptoms do not worsen about 2 weeks after administration of the topical composition has ceased. In embodiments described herein, the one or more symptoms do not worsen about 3 weeks after administration of the topical composition has ceased. In embodiments described herein, the one or more symptoms do not worsen about 4 weeks after administration of the topical composition has ceased. In embodiments described herein, the one or more symptoms do not worsen about 8 weeks after administration of the topical composition has ceased. In embodiments described herein, the one or more symptoms do not worsen about 12 weeks after administration of the topical composition has ceased. In embodiments described herein, the one or more symptoms do not worsen about 16 weeks after administration of the topical composition has ceased. In embodiments described herein, the one or more symptoms do not worsen about 20 weeks after administration of the topical composition has ceased.

In embodiments described herein, the topical composition exhibits low systemic absorption following topical application. In embodiments described herein, the topical composition exhibits no accumulation with repeat dosing. Systemic absorption of tapinarof is measured in plasma. In embodiments described herein, plasma concentration of tapinarof is below the limit of detection (LOD) when measured at 1, 2, 4, 6, 8 and 24 hours following once daily application of the topical composition described herein. In embodiments described herein, plasma concentration of tapinarof is below the limit of detection (LOD) when measured at 1, 2, 4, 6, 8 and 24 hours following twice daily application of the topical composition described herein. In some embodiments, the mean $AUC_{[0-24]}$ is about 23.4 to about 2.2 h*ng/mL. In some embodiments, the mean $AUC_{[0-24]}$ is about 10.5 to about 1.5 h*ng/mL.

In embodiments described herein, the topical composition is more effective than topical corticosteroids, apremilast (Otezla™), calcipotriene and betamethasone dipropionate (Enstilar™), or vitamin D.

In embodiments described herein, the topical composition can be used in a long-term treatment regimen, compared with topical corticosteroids which can only be used for 2-4 weeks. In embodiments described herein, the topical composition can be used for greater than 12 weeks.

In embodiments described herein, the topical composition is administered in an initial dosing regimen followed by a maintenance dosing regimen. In embodiments described herein, the initial dosing regimen is about 1 week to about 24 weeks in duration. In embodiments described herein, the maintenance dosing regimen is about 1 week to about 24 weeks in duration. In embodiments described herein, the topical composition administered in the initial dosing regimen contains 1% tapinarof. In embodiments described herein, the topical composition administered in the maintenance dosing regimen contains 0.5% tapinarof.

In embodiments, the method may include the co-administration of additives, other second active agents or enzymes as described herein. In embodiments, co-administration may be at the same time, substantially the same time, before or after administration of the topical compositions described herein.

In embodiments, the additives may be selected from the group consisting of vitamins, cosmetic peptides, oil control agents, sensation modifying agents, skin lightening agents, hydrating compositions, a sunblock agent, a compound that absorbs or reflects UV photons, other skin care agents, a second active agent and combinations thereof, as described herein.

In some embodiments, administration of the composition is by topical application, transdermal, percutaneous, or microneedle injection.

In embodiments, the composition is administered by microneedle injection. Microneedle is a hollow needle having an exposed height of between about 0 and 1 mm and a total length of between about 0.3 mm to about 2.5 mm. Preferably, the microneedle is a hollow needle having a length of less than about 2.5 mm. Most preferably, the microneedle is a hollow needle having a length of less than about 1.7 mm. The composition comprising therapeutic cells and extracellular matrix component are delivered into the skin to a depth of at least about 0.3 mm and no more than about 2.5 mm by the microneedle.

In some embodiments, the topical composition can be applied to the skin one, two, three, four, five or more times each day, and applying can be carried out for a period of at least 1 month, 2 months, 3 months, 4 months, 6 months, 8 months or 12 months.

In such embodiments, the topical composition can be applied to the skin one, two, three, four, five or more times each day, and applying can be carried out for a period of at least 1 month, 2 months, 3 months, 4 months, 6 months, 8 months or 12 months.

In some embodiments, the topical composition may be administered once, as needed, once daily, twice daily, three times a day, once a week, twice a week, every other week, every other day, or the like for one or more dosing cycles. A dosing cycle may include administration for about 1 week, about 2 weeks, about 3 weeks, about 4 weeks, about 5 weeks, about 6 weeks, about 7 weeks, about 8 weeks, about 9 weeks, or about 10 weeks. After this cycle, a subsequent cycle may begin approximately 1, 2, 3, 4, 5, 6, 7, 8, 9, 10, 11, or 12 weeks later. The treatment regime may include 1, 2, 3, 4, 5, or 6 cycles, each cycle being spaced apart by approximately 1, 2, 3, 4, 5, 6, 7, 8, 9, 10, 11, or 12 weeks.

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

EXAMPLES

Example 1—Results of Phase II Clinical Study in AD

This study, which included 247 subjects, was conducted to evaluate the efficacy and safety of a range of concentrations of Tapinarof cream for the topical treatment of AD in adolescents and adults. Results of this study will be used to select the most appropriate concentration and application frequency of Tapinarof cream to evaluate in Phase III clinical studies.

The study objectives and the associated endpoints were as described in Table 1.

TABLE 1

| Study Objectives and Associated Endpoints | |
|---|---|
| Objectives | Endpoints |
| Primary | |
| To estimate the relationship between GSK2894512 cream concentrations (0.5%, 1%) and application frequency with efficacy response, based upon clinical evaluations in subjects with AD | Proportion of subjects who had an Investigator Global Assessment (IGA) score of clear or almost clear (0 or 1) at Week 12 and a minimum 2-grade improvement in IGA score from Baseline to Week 12 |
| Secondary | |
| To estimate the efficacy of GSK2894512 cream | Proportion of subjects who achieved an IGA score of 0 or 1 and a minimum 2-grade improvement from Baseline to each study visit<br>Proportion of subjects with a minimum 2-grade improvement in IGA score from Baseline to each study visit<br>Proportion of subjects with an IGA score of 0 or 1 at each study visit<br>Mean change in IGA score from Baseline to each study visit<br>Proportion of subjects with ≥75% improvement in Eczema Area and Severity Index (EASI75) from Baseline to each study visit<br>Mean percent change in Eczema Area and Severity Index (EASI) score from Baseline to each study visit<br>Proportion of subjects with ≥50% improvement in EASI (EASI50) from Baseline to each study visit<br>Mean change in EASI score from Baseline to each study visit<br>Mean change in percent of body surface area (% BSA) affected from Baseline to each study visit<br>Mean change in Total Severity Score (TSS) from Baseline to each study visit<br>Mean percent change in TSS from Baseline to each study visit<br>Mean change in individual signs of TSS from Baseline to each study visit<br>Mean percent change in individual sign of TSS from Baseline to each study visit<br>Mean change in weekly average of daily itch/pruritus (numeric rating scale [NRS]) score (based on Item #1 of Daily Sign & Symptom Severity Diary) from Baseline to Week 12<br>Mean Percent change in weekly average of daily itch/pruritus (NRS) score (based on Item #1 of Daily Sign & Symptom Severity Diary) from Baseline to Week 12<br>Proportion of subjects who achieved a minimum 3-point improvement in weekly average of itch/pruritus (NRS) from Baseline to each study visit |
| To describe the safety and tolerability of GSK2894512 cream | Incidence, frequency, and nature of AEs and serious adverse events (SAEs)<br>Local tolerability scores over time<br>Change over time in clinical laboratory tests and frequency of clinically-significant abnormal test results<br>Change over time in vital signs and frequency of clinically-significant abnormal results<br>Incidence and nature of abnormal electrocardiograms (ECGs) |
| To describe the safety and tolerability of GSK2894512 cream | Incidence, frequency, and nature of AEs and serious adverse events (SAEs)<br>Local tolerability scores over time<br>Change over time in clinical laboratory tests and frequency of clinically-significant abnormal test results<br>Change over time in vital signs and frequency of clinically-significant abnormal results<br>Incidence and nature of abnormal electrocardiograms (ECGs) |
| Other | |
| To describe the effect of GSK2894512 cream on subject-reported outcomes | Change in expanded Patient-Oriented Eczema Measure (POEM) items from Baseline to each study visit<br>Change in weekly average of Daily Sign and Symptom Severity Diary score from Baseline to each study visit<br>Subject impression of severity of eczema symptoms and overall change in severity of eczema symptoms and overall change in itch/pruritus from Baseline to Week 12 |
| To characterize the population pharmacokinetics (PK) of GSK2894512 after topical | Population estimates of PK parameters as data permit |

TABLE 1-continued

| Study Objectives and Associated Endpoints | |
|---|---|
| Objectives | Endpoints |
| application of GSK2894512 cream | |
| To explore the relationship between topical exposure (i.e., cream concentration and % BSA treated), efficacy, and/or safety, and systemic exposure of GSK2894512, as data permit. | Relationship between cream concentration and/or % BSA treated and changes in systemic exposure as data permit<br>Relationship between systemic exposure and changes in efficacy (e.g., IGA score) and/or safety endpoints, as appropriate |
| To estimate the duration of response of GSK2894512 cream | Proportion of subjects who had an IGA score of 0 or 1 at Week 12 and a minimum 2-grade improvement in IGA score from Baseline to Week 12 and who maintained that response at 2 and 4 weeks post-treatment<br>Proportions of subjects who achieved improvement with respect to individual secondary efficacy endpoints at Week 12 and maintained the improvement at 2 and 4 weeks post-treatment, as appropriate |
| To explore the measurement properties of the Daily Sign and Symptom Severity Diary | Evaluate the reliability, validity, and ability to detect change of the Daily Sign and Symptom Severity Diary, including the itch/pruritus NRS |

Study Design

This was a multicenter (United States, Canada, and Japan), randomized, double-blind (Sponsor-unblind), vehicle-controlled, 6-arm, parallel-group, dose-finding study in adolescent and adult subjects with AD.

The study consisted of 3 periods: up to 4 weeks screening, 12 weeks double-blind treatment, and 4 weeks post-treatment Follow-up. Study visits occurred at Screening; Baseline; Weeks 1, 2, 4, 8, and 12 during the treatment period; and 2 and 4 weeks after the last application of study treatment (i.e., at Weeks 14 and 16). Additional visits could occur, as needed, to follow-up on any skin reactions or ongoing AEs. A subject's total duration of study participation was approximately 16 to 20 weeks.

Two concentrations of Tapinarof cream (0.5% and 1%) and a vehicle control were evaluated following application to all AD lesions (except on the scalp) once or twice daily for 12 weeks. There were no planned dose adjustments during the study. It was expected that approximately 270 adolescent and adult subjects with AD would be screened to achieve 228 randomized subjects (1:1:1:1:1:1; N=3 8 for each of the 6 treatment groups) and approximately 204 evaluable subjects overall. At least 30 subjects were to be randomized in Japan to achieve at least 24 evaluable Japanese subjects. To ensure an adequate number of adolescents (aged 12 to 17 years) versus adults were represented in the overall study population, enrollment was limited to approximately 65% of either age group.

The ITT Population was to include all randomized subjects. Subjects who prematurely discontinued from the study were not replaced.

Efficacy was assessed by using a 5-point static Investigator Global Assessment (IGA) (0-4 scale), the Eczema Area and Severity Index (EASI), percent of body surface area (% BSA) involvement, severity of AD signs using a Total Severity Score (TSS), and by subject-reported itch/pruritus severity using a numeric rating scale (NRS) (from the Daily Sign and Symptom Severity Diary). Additional subject-reported outcomes included the expanded Patient-Oriented Eczema Measure (POEM), a Daily Sign and Symptom Severity Diary, and subject impression of severity of eczema symptoms and overall change in severity of eczema symptoms and overall change in itch/pruritus items. There was also an investigator global impression of change item.

Safety was assessed by the monitoring and recording of all AEs and serious adverse events (SAEs); evaluation of local (application site) tolerability; monitoring of hematology (including peripheral blood immunophenotyping and immunoglobulins), clinical chemistry, and vital signs; and the performance of ECGs and physical examinations.

An independent data monitoring committee (IDMC) was utilized in this study to ensure external objective medical and/or statistical review of safety issues.

An unblinded, interim analysis was carried out (database lock: 11 Jul. 2016) to identify the appropriate drug concentration and topical application frequency of GSK2894512 for use in Phase III clinical studies. The interim analysis was conducted when approximately 100 subjects had completed the Week 8 visit. The access to unblinded information was limited and defined a priori in a study results dissemination plan.

Discussion of Study Design

The randomized, double-blind (Sponsor-unblind), vehicle-controlled study design was selected to minimize the potential for subjective bias related to possible identification of which subjects are receiving active treatment and to minimize selection and allocation bias by balancing potential prognostic factors. The study was conducted at multiple study centers to enhance the possibility of inclusion of a wider range of population groups and to subsequently increase generalizability of the results.

Clinical studies in skin conditions have historically shown a notable vehicle (as well as placebo) response rate, which could be attributable to the effects of skin moisturization or to the increased emphasis on proper skin care while participating in a clinical study. A vehicle control group was included in this study to provide a control for comparison and to ensure study assay sensitivity for characterization of the safety and efficacy profile of Tapinarof cream.

The predicted maximum systemic exposure to Tapinarof in this study was expected to be lower than the no observed adverse effects level (NOAEL) identified in nonclinical toxicology studies. Exposure predicted based on in vitro flux data and topical minipig relative bioavailability showed a lesser systemic exposure for 1% cream Formulation F versus Formulations C or E. This provided a safety margin of 4- to 8-fold for predicted area under the concentration-time curve (AUC) for 24 hours (0-24) and 4- to 6-fold for predicted maximum observed concentration (Cmax) for 1% cream (Formulation F) applied twice daily when compared with the NOAEL obtained from the rat subcutaneous 3 mg/kg/day, 13-week toxicology study (99 ng. h/mL for $AUC_{(0-24)}$ and 31.6 ng/mL for Cmax).

The treatment duration was 12 weeks. Previous studies of Tapinarof cream (using Formulation C) showed some efficacy within the first 14 days of treatment and increasing efficacy over 12 weeks of treatment. The 12-week treatment endpoint in this study was expected to be an adequate duration of treatment to measure response.

Inclusion Criteria

A subject was eligible for inclusion in this study only if all of the following criteria applied: 1. Male or female aged 12 years to 65 years, inclusive, at the time of informed consent; 2. Diagnosis of AD fulfilling the specified diagnostic criteria and having active inflammation; 3. Body surface area involvement >5% and <35%, excluding scalp, at Screening and Baseline; 4. An IGA of AD score >3 at Baseline; 5. At least 1 target lesion that measured at least 3 $cm^2$ at Screening and Baseline, Must have been representative of the subject's disease state, but not located on the hands, feet or genitalia; 6. A female subject was eligible to participate if she was not pregnant (as confirmed by a negative urine human chorionic gonadotrophin [hCG] test), not lactating, and when at least one of the following conditions applied: a. Non-reproductive potential defined as: pre-menopausal females with 1 of the following: documented tubal ligation, documented hysteroscopic tubal occlusion procedure with follow-up confirmation of bilateral tubal occlusion, hysterectomy, documented dilateral oophorectomy, postmenopausal was defined as 12 months of spontaneous amenorrhea (in questionable cases a blood sample with simultaneous follicle stimulating hormone [FSH] and estradiol levels consistent with menopause [refer to laboratory reference ranges for confirmatory levels]). Females on hormone replacement therapy (HRT) and whose menopausal status was in doubt were required to use 1 of the highly effective contraception methods if they wished to continue their HRT during the study. Otherwise, they had to discontinue HRT to allow confirmation of post-menopausal status prior to study enrollment. b. Reproductive potential and agreed to follow 1 of the options listed in the Modified List of Highly Effective Methods for Avoiding Pregnancy in Females of Reproductive Potential (FRP) (see Protocol, Appendix 5) from 30 days prior to the first dose of study medication and until after the last dose of study medication and completion of the Follow-up visit. The investigator was responsible for ensuring that subjects understood how to properly use these methods of contraception.

Exclusion Criteria

A subject was not eligible for inclusion in this study if any of the following criteria applied: 1. Unstable course of AD (spontaneously improving or rapidly deteriorating) as determined by the investigator over the previous 4 weeks prior to Baseline; 2. Concurrent conditions and history of other diseases: a. Immunocompromised (e.g., lymphoma, acquired immunodeficiency syndrome, Wiskott-Aldrich Syndrome) or had a history of malignant disease within 5 years before the Baseline visit). b. Chronic or acute infection requiring treatment with systemic antibiotics, antivirals, antiparasitics, antiprotozoals, or antifungals within 4 weeks before the Baseline visit. c. Active acute bacterial, fungal, or viral (e.g., herpes simplex, herpes zoster, chicken pox) skin infection within 1 week before the Baseline visit. d. Any other concomitant skin disorder (e.g., generalized erythroderma such as Netherton's Syndrome or psoriasis), pigmentation, or extensive scarring that in the opinion of the investigator could interfere with the evaluation of AD lesions or compromise subject safety. e. Presence of AD lesions only on the hands or feet without prior history of involvement of other classical areas of involvement such as the face or the folds. f. Other types of eczema. 3. A history or ongoing serious illness or medical, physical, or psychiatric condition(s) that, in the investigator's opinion, could have interfered with the subject's completion of the study. 4. Known hypersensitivity to excipients. 5. Current or chronic history of liver disease, known hepatic or biliary abnormalities (with the exception of Gilbert's syndrome or asymptomatic gallstones), presence of hepatitis B surface antigen (HBsAg), or positive hepatitis C antibody test result within 3 months of Screening. 6. Liver function tests: alanine aminotransferase (ALT) >2× upper limit of normal (ULN); alkaline phosphatase and bilirubin >1.5×ULN (isolated bilirubin >1.5×ULN was acceptable if bilirubin was fractionated and direct bilirubin <35%). 7. QT interval corrected for heart rate (QTc) >450 msec or QTc >480 msec for subjects with bundle branch block. 8. The QTc is the QT interval corrected for heart rate, with machine overread. The QTc was to be based on a single ECG obtained over a brief recording period. If QTc was outside of the threshold value, triplicate ECGs could be performed with the QTc values averaged. (Refer to Protocol, Section 7.4.5 for information on QTc correction formula.) 9. Ultraviolet (UV) light therapy or prolonged exposure to natural or artificial sources of UV radiation (e.g., sunlight or tanning booth) within 4 weeks prior to the Baseline visit and/or intention to have such exposure during the study, which was thought by the investigator to potentially impact the subject's AD. 10. Used any of the following treatments within the indicated washout period before the Baseline visit: a. 12 weeks or 5 half-lives (whichever was longer)—biologic agents (e.g., 18 weeks for omalizumab). b. 8 weeks—cyclosporin, methotrexate, azathioprine, or other systemic immunosuppressive or immunomodulating agents, (e.g., mycophenolate or tacrolimus). c. 4 weeks—systemic corticosteroids or adrenocorticotropic hormone analogs. d. 2 weeks—topical treatments: corticosteroids, calcineurin inhibitors, or coal tar (on the body). e. 2 weeks—immunizations; sedating antihistamines (nonsedating antihistamines were permitted). f. 1 week—topical antibiotics, antibacterial cleansing body wash/soap or diluted sodium hypochlorite "bleach" baths. 11. Participated in a clinical study and received an investigational product within the following time period prior to the Baseline visit: 4 weeks, 5 half-lives, or twice the duration of the biological effect of the investigational product (whichever was longer). 12. History of alcohol or other substance abuse within the last 2 years. 13. Participated in a previous study using Tapinarof (or WBI-1001).

Investigational Product and Reference Therapy: The term 'study treatment' is used throughout this document to describe the product (i.e., Tapinarof or vehicle) received by subject as per the protocol design, as shown in Table 2.

TABLE 2

Investigational Product and Reference Therapy

| Drug | Dose/Form/Route | Frequency/Duration |
|---|---|---|
| Tapinarof | 1% (10 mg/g), cream, topically | BID, 12 weeks |
| Tapinarof | 1% (10 mg/g), cream, topically | QD, 12 weeks |
| Tapinarof | 0.5% (5 mg/g), cream, topically | BID, 12 weeks |

TABLE 2-continued

| Investigational Product and Reference Therapy | | |
|---|---|---|
| Drug | Dose/Form/Route | Frequency/Duration |
| Tapinarof | 0.5% (5 mg/g), cream, topically | QD, 12 weeks |
| Vehicle | 0%, cream, topically | BID, 12 weeks |
| Vehicle | 0%, cream, topically | QD, 12 weeks |

The list of excipients include are propylene glycol, diethylene glycol monoethyl ether, polysorbate 80, medium chain triglycerides, emulsifying wax non-ionic, polyoxyl stearyl ether 2, polyoxyl stearyl ether 20, benzoic acid, butylated hydroxytoluene, purified water, sodium citrate, citric acid monohydrate, and edetate disodium.

Primary Endpoint

The primary endpoint was the proportion of subjects who had an IGA score of clear or almost clear (0 or 1) at Week 12 and a minimum 2-grade improvement in IGA score from Baseline to Week 12.

Investigator's Global Assessment: The IGA is a clinical tool for assessing the current state/severity of a subject's AD. It is a static 5-point morphological assessment of overall disease severity, as determined by the investigator, using the clinical characteristics of erythema, infiltration, papulation, oozing, and crusting as guidelines. At each specified time point, the IGA was made without reference to previous scores. Scoring system ranges from 0 (=Clear) to 4 (=Severe).

Secondary Endpoints

Secondary endpoints were the following: 1. Proportion of subjects who achieved an IGA score of 0 or 1 and a minimum 2-grade improvement from Baseline to each study visit; 2. Proportion of subjects with a minimum 2-grade improvement in IGA score from Baseline to each study visit; 3. Proportion of subjects with an IGA score of 0 or 1 at each study visit; 4. Mean change in IGA score from Baseline to each study visit; 5. Proportion of subjects with >75% improvement in EASI (EASI75) from Baseline to each study visit; 6. Mean percent change in EASI score from Baseline to each study visit; 7. Proportion of subjects with >50% improvement in EASI (EASI50) from Baseline to each study visit; 8. Mean change in EASI score from Baseline to each study visit; 9. Mean change in % BSA affected from Baseline to each study visit; 10. Mean change in TSS from Baseline to each study visit; 11. Mean percent change in TSS from Baseline to each study visit; 12. Mean change in individual sign of TSS from Baseline to each study visit; 13. Mean percent change in individual signs of TSS from Baseline to each study visit; 14. Mean change in weekly average of daily itch/pruritus (NRS) score (based on Item #1 of Daily Sign & Symptom Severity Diary) from Baseline to Week 12; 15. Mean Percent change in weekly average of daily itch/pruritus (NRS) score (based on Item #1 of Daily Sign & Symptom Severity Diary) from Baseline to Week 12; 16. Proportion of subjects who achieved a minimum 3-point improvement in weekly average of itch/pruritus (NRS) from Baseline to each study visit.

Eczema Area and Severity Index: The EASI scoring system is a standard clinical tool for assessing the severity of AD that takes into account the overall severity of erythema, infiltration/papulation, excoriation, and lichenification, as well as the extent of BSA affected with AD. The 4 clinical signs are each graded on a 4-point scale (0 to 3) for each of the 4 specified body regions (head and neck, upper extremities, lower extremities, and trunk). The EASI is a static assessment made without reference to previous scores.

Body Surface Area: The extent of BSA affected by AD is a general indicator of disease severity and was measured throughout the study. The extent of BSA to which study treatment was applied was also recorded. For the purpose of approximate clinical estimation, the total palmar surface of the palm plus 5 digits was assumed to be approximately equivalent to 1% BSA.

Total Severity Score: A single target lesion that measured at least 3 cm at Screening and Baseline and was representative of subject disease, but not located on hands, feet or genitalia, was selected at Baseline to assess efficacy in treating a discrete area rather than an overall average of all areas. For that lesion, the severity of erythema, induration/papulation, lichenification, oozing/crusting, and scaling was assessed on a 4-point scale and TSS was calculated. The maximum score was 15, with higher scores indicating more severe disease.

Investigator Impression of Change Item: This was a single item that asked the investigator to rate the change from Baseline in the subject's overall AD symptoms. Response options ranged from "1=very improved" to "7=very worse". Results will also be used as a clinical anchor in analyses of the minimally-important differences in the Daily Sign and Symptom Severity Diary, including itch/pruritus.

Pruritus/Itch Severity: Pruritus is the most frequent symptom of AD and potentially has the greatest effect on quality of life. Subject-reported itch severity was obtained from the itch item from the Daily Sign and Symptom Severity Diary.

Other Efficacy Endpoints

Other efficacy endpoints were as follows: Relationship between cream concentration and/or % BSA treated and changes in systemic exposure, as data permitted; Proportions of subjects who achieved an IGA score of 0 or 1 at Week 12 and a minimum 2-grade improvement from Baseline to Week 12 and who maintained the improvement at 2 and 4 weeks post-treatment; Proportions of subjects who achieved improvement with respect to individual secondary efficacy endpoints at Week 12 and maintained the improvement at 2 and 4 weeks post-treatment, as appropriate; To evaluate the reliability, validity, and ability to detect change of the Daily Sign and Symptom Severity Diary, including the itch/pruritus NRS item; Endpoint related to systemic exposure: Relationship between systemic exposure and changes in efficacy (e.g., IGA score) and/or safety endpoints, as appropriate Pharmacokinetics: A total of 5 blood samples for PK analysis of GSK2894512 were collected from each subject over the clinic visits at Weeks 1, 2, 4, 8, and 12. Plasma analysis was performed under the management of Bioanalytical Science and Toxicokinetics, DMPK, GSK.

Health Outcomes

Endpoints related to subject-reported outcomes were: Subject impression of severity of eczema symptoms and overall change in severity of eczema symptoms and overall change in itch/pruritus from Baseline to Week 12; change in expanded POEM items from Baseline to each study visit; change in weekly average of Daily Sign and Symptom Severity Diary score from Baseline to each study visit.

In order to evaluate symptoms and symptom impact, subjects completed a Subject Impression of Severity and Change questionnaire, the expanded POEM, as well as a Daily Sign and Symptom Severity Diary to record AD symptoms. Each investigator also completed an impression of change item (assessing change in severity of AD symptoms) for each subject.

Subject Impression of Severity and Change Items

At Baseline, treatment, early withdrawal, and Follow-up, subjects were asked to rate the overall severity of their AD symptoms on a scale ranging from "1=mild" to "4=very severe."

At Weeks 4, 8, 12, early withdrawal, and Follow-up, the global impression of change items asked subjects to rate their change from Baseline in overall severity of AD symptoms and in overall severity of itch. Response options ranged from "1=very improved" to "7=very worse."

Daily Sign and Symptom Severity Diary: The self-administered Daily Sign and Symptom Severity Diary (which is based on the content of the POEM) assesses the severity of 11 disease-related signs and symptoms (skin that is itchy, discolored, bleeding, oozing, cracked, scaly, flaky, dry/rough, painful, burning, and stinging). Response options are on an 11-point NRS and range from 0 (Absent) to 10 (Worst Imaginable). The recall period was the previous 24 hours. Subjects completed the diary each day at home using an electronic diary. Adolescents (subjects aged 12 to 17) and adults completed the same version of the Daily Sign and Symptom Severity Diary. Question 1 was used to assess itch.

Expanded Patient-Oriented Eczema Measure (POEM): The POEM is a self-assessed measurement tool for monitoring disease activity in children and adults with AD. Seven symptoms (skin that is itchy, bleeding, weeping/oozing, cracked, flaking, dry/rough, and disturbed sleep) are measured using a 5-point scale of frequency of occurrence during the previous week. The POEM was scored as its original 7-item measure. Individual responses were scored from 0 to 4.

POEM was expanded with an additional 3 questions to assess sleep quality; these were not included in the original published instrument. One question asked about the frequency of waking at night and 2 questions asked about difficulty falling asleep. These 3 newly-developed sleep items were analyzed separately.

Primary Efficacy Endpoint

The primary efficacy analyses were conducted on the ITT and PP population, unless otherwise specified.

The study day relative to Day 1 was used as a covariate in the model.

The primary analysis was a repeated measures factorial logistic regression for the primary endpoint (proportion of subjects who have an IGA score of 0 or 1 at Week 12 and a minimum 2-grade improvement in IGA score from Baseline to Week 12) with covariates for dose (0% for vehicle, 0.5% and 1%), frequency of administration (once or twice daily), and study day as well as a dose by frequency interaction term. The response at each visit was modelled as repeated measures via inclusion of a random subject effect. Time was included in the model according to an Integrated Two-Component Prediction (ITP) model [Brown 2001]. Estimated population mean dose/frequency-response curves along with their corresponding 95% confidence bands were provided both graphically and in table format for all dose levels and frequencies by time point of interest. Estimated mean difference in response rate with 95% confidence interval between Tapinarof and vehicle cream for BID and QD were provided by time point of interest.

Supportive statistical analysis of primary endpoint based on Japanese subjects in the ITT population was conducted for 2 frequencies (once or twice daily) separately using simple logistic regression model with covariate for dose (0% for vehicle, 0.5% and 1%). The same analysis was done for the overall ITT and PP Populations to compare the results of Japanese population and overall population.

Summary statistics of the number of subjects providing data at the relevant time point, frequency counts and percentages, and 95% confidence interval were provided for the IGA response rate for each treatment group at each study visit. Mean and 95% confidence intervals were provided for the difference of (each BID dose—vehicle BID) and the difference of (each QD dose—vehicle QD) in IGA response rate at each visit.

Secondary Efficacy Endpoints

The secondary efficacy analyses were based on the ITT population, unless otherwise specified. The following key secondary efficacy analyses were based on the ITT and PP Populations: proportion of subjects who achieved an IGA score of (0 or 1) and a minimum 2-grade improvement from Baseline to each study visit, proportion of subjects with EASI50 from Baseline to each study visit, and mean change in EASI score from Baseline to each study visit.

For continuous secondary endpoints, a repeated measures Emax model with ITP time component was fitted to the data. All dichotomous secondary endpoints were modeled in the same logistic regression model described in the primary statistical analysis. For continuous data, summary statistics of the mean, standard deviation (SD), median, minimum, maximum, 95% confidence interval and number of observations were provided for each treatment group at each study visit. For data of proportions, summary statistics of the number of subjects providing data at the relevant time point, frequency counts and percentages, and 95% confidence interval were provided for each treatment group at each study visit. Mean and 95% confidence intervals were provided for the difference of (each BID dose—vehicle BID) and the difference of (each QD dose—vehicle QD) at each visit.

Demographics and Baseline Characteristics

Out of the 247 subjects randomized in this study, 174 (70%) were aged 18 to 65 years (adults) and 73 subjects (30%) were aged 12 to 17 years (adolescents).

Overall, mean demographic and Baseline characteristics were comparable across treatment groups. Most subjects (91%) had a Baseline IGA category of "3=moderate". The mean Baseline EASI score was 11.25 (SD 5.956), the mean % BSA affected was 16.91% (SD 10.042), the mean itch/pruritus score was 5.5 (SD 2.12), and the mean TSS score was 8.0 (SD 2.27).

By age group, Baseline IGA category for adults and adolescents were similar (92%) to the overall population; however, Baseline mean TSS score was slightly lower for adults (7.9 [SD 2.31]) and slightly higher for adolescents (8.2 [SD 2.19]).

Note that 2 subjects were included in the database appearing to be 11 years old. This was due to only the year of birth being recorded on the eCRF, with the birth date assumed to be the middle of the year (1 June) for the analyses. Subjects born in the first half of 2004 who gave consent before June therefore appear as 11-year-olds in the database despite actually being 12 years old. These subjects were therefore included in the adolescent group (12-17 years of age) in the statistical summaries.

Most Japanese subjects (96%) also had a Baseline IGA category of "3=moderate"; the overall mean EASI score was 12.21 (SD 6.274), mean % BSA affected was 19.25% (SD 9.348), the mean itch/pruritus score was 5.0 (SD 2.01), and the mean TSS score (7.4 [SD 1.97]).

The sample size at Baseline for the impression of severity item (242 subjects) and itch/pruritus item (226 subjects) was slightly smaller than the rest of the Baseline characteristics (247 subjects).

Baseline duration of AD in the Japanese population was similar across treatment groups. Similar patterns were also observed by age group. By sub-group, mean duration was shortest in the Japanese subjects (9.50 [SD 8.57] years) followed by the adolescent subjects (11.52 [SD 5.44] years) and adult subjects (21.56 [SD 14.70] years).

A total of 247 subjects (of the 363 subjects originally screened) were randomized into the study at 32 sites in the United States, eight sites in Canada, and 13 sites in Japan (ITT analysis population). Of those randomized, 191 subjects (77%) completed the study including the Week 16 follow-up visit. Overall, mean demographic and baseline characteristics were comparable across treatment groups (Table 3). Most subjects (91%) had a baseline IGA score of 3 (moderate) and a baseline mean Eczema Area and Severity Index (EASI) score of 11.3 (SD 6.0). Primary endpoint: IGA response rates (defined as IGA score of 0 or 1 and ≥2-grade improvement) at Week 12 were higher with all tapinarof cream groups than vehicle groups (53% [1% BID]; 46% [1% QD]; 37% [0.5% BID]; 34% [0.5% QD]; 24% [vehicle BID], and 28% [vehicle QD]) and were maintained for 4 weeks after the end of study treatment (non-responder imputation [NRI] method).

improvement in IGA score from Baseline to Week 8 with Tapinarof cream concentrations 1% BID, 1% QD, 0.5% BID, 0.5% QD, respectively, and 15% for vehicle BID and 27% for vehicle QD. Response rates of 45%, 63%, 59%, 35% at Week 8 for the proportion of subjects who had achieved 75% reduction in EASI from Baseline to Week 8 with Tapinarof cream concentrations 1% BID, 1% QD, 0.5% BID, 0.5% QD, respectively, and 23% for vehicle BID and 33% for vehicle QD. Clinically meaningful itch reduction in weekly average NRS was observed by Week 4 (median) −56.35%, −57.14%, −53.00%, −53.57%, with Tapinarof concentrations 1% BID, 1% QD, 0.5% BID, 0.5% QD, respectively, and −2.38% for vehicle BID and −38.33% for vehicle QD. Itch reduction was observed as early as Week 1 in the Tapinarof groups. Most frequent AEs (frequency >10% in at least 1 treatment arm) were folliculitis, nasopharyngitis, acne, and atopic dermatitis (worsening of pre-existing AD).

Investigator Global Assessment (IGA): The primary efficacy analyses were based on the ITT and PP Populations, unless otherwise specified. For subjects who discontinued investigational product before Week 12, any data after the last known administration of investigational product were

TABLE 3

Baseline subject demographics and characteristics

| | Tapinarof 1% | | Tapinarof 0.5% | | Vehicle | |
|---|---|---|---|---|---|---|
| | BID (n = 40) | QD (n = 41) | BID (n = 43) | QD (n = 41) | BID (n = 42) | QD (n = 40) |
| Mean age, years (SD) | 28.5 (13.9) | 31.6 (15.7) | 29.0 (15.9) | 29.3 (14.0) | 27.9 (14.7) | 29.4 (15.2) |
| Aged 12-17 years*, n (%) | 11 (28) | 13 (32) | 13 (30) | 12 (29) | 13 (31) | 11 (28) |
| Aged 18-65 years, n (%) | 29 (73) | 28 (68) | 30 (70) | 29 (71) | 29 (69) | 29 (73) |
| Male sex, n (%) | 22 (55) | 17 (41) | 26 (60) | 19 (46) | 19 (45) | 23 (58) |
| IGA score, mean (SD) | 3.1 (0.2) | 3.1 (0.3) | 3.1 (0.3) | 3.1 (0.3) | 3.1 (0.4) | 3.1 (0.3) |
| EASI score, mean (SD) | 9.8 (5.1) | 11.0 (6.1) | 13.1 (6.7) | 11.4 (5.8) | 11.1 (5.8) | 11.1 (5.8) |
| BSA affected, % (SD) | 14.8 (8.7) | 18.7 (11.0) | 19.7 (10.5) | 17.6 (9.9) | 14.5 (9.2) | 16.0 (10.3) |
| Pruritus score, mean (SD)† | 5.2 (2.3) | 5.4 (1.9) | 5.7 (2.5) | 5.7 (2.0) | 5.1 (2.0) | 5.8 (1.9) |

*Two subjects with age <12 years are included in the 12-17 years sub-group.

†Mean scores based on a numerical rating scale (NRS) of 0 ‘absent’ to 10 ‘worst imaginable’.

Data provided for the safety analysis population (n = 247).

BID, twice daily; BSA, body surface area; EASI, Eczema Area and Severity Index; IGA, Investigator Global Assessment; QD, once daily; SD, standard deviation.

Efficacy Results

Efficacy results are reported using the ITT and PP Population. Results are further presented by overall population, adult population (18 to 65 years), adolescent population (12 to 17 years), and Japanese population.

Interim Analysis

A “go” decision was reached based on a clinically meaningful efficacy profile and a well-tolerated safety profile (the analysis was conducted when 100 subjects completed the Week 8 visit): Response rates of 35%, 74%, 35%, 40% at Week 8 for the proportion of subjects who had an IGA score of clear or almost clear (0 or 1) and a minimum 2-grade excluded from the primary efficacy analyses. The study day relative to Day 1 was used as a covariate in the model. Data after Week 12 and data after withdrawal visits were excluded from the efficacy analyses.

The primary objective of this study was to estimate the relationship between Tapinarof cream concentrations (0.5% and 1%) and application frequency (QD or BID) with efficacy response based upon clinical evaluation in subjects with AD. The primary endpoint was the proportion of subjects who had an IGA score of clear or almost clear (0 or 1) at Week 12 and a minimum 2-grade improvement in IGA score from Baseline to Week 12. A subject was defined as having "IGA treatment success" when they met the criteria for this endpoint, i.e., an IGA score of clear or almost clear (0 or 1) and a minimum 2-grade improvement in IGA score.

On average, the probability of achieving an IGA treatment success (IGA score of clear or almost clear and minimum 2-grade improvement from Baseline to Week 12) was highest in the 1% active treatment groups (67.7% and 62.6% in the BID and QD groups, respectively), followed by the 0.5% active treatment groups (28.7% and 18.3% in the BID and QD groups, respectively. This trend was seen at all visits starting at Week 1.

At Week 12, the difference in the probability of IGA responses between active treatment groups and vehicle treatment groups was highest in the 1% treatment groups (61.5% and 60.1% in the BID and QD groups, respectively). The difference in the probability of getting an IGA response between 0.5% active treatment groups and vehicle groups was 22.4% and 15.7% in the BID and QD groups, respectively.

Overall, the primary endpoint analysis showed a higher proportion of subjects with IGA treatment success in the 1% BID and 1% QD groups and the 0.5% BID group than in the vehicle groups at Week 12. Although there was clear separation between the 0.5% QD group and the vehicle groups at Week 4 and Week 8, at Week 12 the proportion of subjects with IGA treatment success leveled off (to 40%) in the 0.5% QD group and increased sharply in the vehicle QD group (to 44%). The 1% concentration treatment groups showed a higher rate of treatment success than the respective (i.e., BID or QD) 0.5% concentration groups.

In the adult population, the primary endpoint analysis showed a higher proportion of subjects in active treatment groups with IGA treatment success than in vehicle groups at Week 12. The 1% and 0.5% concentration treatment groups showed similar rates of success (between 44% and 54%), with rates somewhat higher with BID application than with QD application.

In the adolescent population, the primary endpoint analysis showed a higher proportion of subjects with IGA treatment success in the 1% BID group than in the 1% QD, 0.5% BID, and both vehicle groups, where there were similar proportions with treatment success. The lowest proportion was seen in the 0.5% QD group at Week 12. The proportion of subjects with IGA treatment success was higher in the 1% concentration treatment groups than the 0.5% concentration groups.

Overall, the proportion of subjects with IGA treatment success in the Tapinarof BID groups continued to increase over time up to Week 12. In the QD active groups the proportion increased to Week 8 and then decreased to Week 12.

In the adult population, the proportion of subjects with treatment success in the active treatment groups continued to increase over time through Week 12, except for the 1% BID group at Week 8 (slight decrease) and the 0.5% QD group at Week 12 (level).

In the adolescent population, the proportion of subjects with treatment success in the Tapinarof 1% QD group was higher and continued to increase over time through Week 8. The same pattern was observed for the Tapinarof 0.5% QD group, although the proportion of subjects with treatment success in this group was lower compared to the other groups. The other treatment groups continued to increase up to Week 12. Both vehicle groups (BID and QD) had a higher proportion of subjects with treatment success at Week 12 than both 0.5% (BID and QD) treatment groups.

IGA secondary endpoint analyses (the proportion of subjects who achieved an IGA score of 0 or 1 and a minimum 2-grade improvement from Baseline to each study visit and maintenance of improvement beyond Week 12) revealed the following: There was an increasing proportion of subjects who had an IGA score of 0 or 1 at each study visit up to Week 12, except for both (1% and 0.5%) active QD groups, where the proportion decreased between Week 8 and Week 12. The 1% concentration treatment groups showed a higher rate of subjects with treatment success than the corresponding 0.5% concentration groups at Week 12. There were no clear differences in the proportion of subjects who met the primary endpoint and maintained the improvement at 2 and 4 weeks post-treatment between active treatment groups and vehicle groups.

Ad-hoc Analysis: Investigator Global Assessment (IGA) Non-Responder Imputation (NRI): The efficacy data for the proportion of subjects who had an IGA score of clear or almost clear (0 or 1) at Week 12 and a minimum 2-grade improvement in IGA score from Baseline to Week 12 were re-analyzed using an NRI to adjust for the higher dropout rates in the vehicle group. Overall, with this method, the higher proportion of subjects with treatment success in the active treatment groups than in vehicle groups was more clearly defined, as well as the overall better efficacy for the 1% concentration at each visit. At Week 12, responses were higher with BID application compared with QD, but this pattern was not seen consistently throughout the treatment period.

In the NRI analysis of the adult population, there was a clear difference between the active and vehicle groups, with similar rates of treatment success between the 1% and 0.5% concentrations and the BID and QD groups.

In the NRI analysis of the adolescent population, a similar pattern was seen to the observed cases (OC) analysis, with a strong vehicle BID response throughout treatment and relatively low proportions of subjects with treatment success in the 0.5% groups.

Eczema Area and Severity Index (EASI): One of the main secondary objectives of this study was to estimate the efficacy of Tapinarof cream using EASI. The main secondary endpoint was the proportion of subjects with EASI75 from Baseline to each study visit.

On average, the probability of achieving EASI75 at Week 12 was highest in the 1% active treatment groups (86.0% and 80.7% in the BID and QD groups, respectively), followed by the 0.5% active treatment groups (54.2% and 32.6% in the BID and QD groups, respectively). The probability of achieving EASI75 at Week 12 in the vehicle groups was 11.6% and 3.7% in the BID and QD groups, respectively. This trend was seen at all other visits starting at Week 1.

The difference in the probability of achieving EASI75 between active treatment groups and vehicle treatment groups was highest in the 1% groups (74.5% and 77.0% in the BID and QD groups, respectively). The difference in the probability of achieving EASI75 between 0.5% and vehicle groups was 42.6% and 28.9% in the BID and QD groups, respectively.

Generally, after Week 1 to the end of the treatment period, the main secondary endpoint analysis showed a higher proportion of subjects overall achieving >75% improvement in EASI (EASI75) from Baseline in the active treatment groups than in the vehicle groups. At Weeks 2 and 4 the 1% concentration groups showed a higher rate of responders than the 0.5% concentration groups, but at Weeks 8 and 12 the 0.5% BID group had similar proportions of subjects with improved EASI75 to the 1% groups.

The pattern of the proportion of adult subjects with >75% improvement in EASI from Baseline to each study visit was similar to the overall population, with a higher proportion in active treatment groups showing improvement than in vehicle groups from Week 2. The adolescent data did not show such clear trends, with a stronger response in the vehicle BID group and a weaker response in the 0.5% QD group compared with the overall population.

The proportion of subjects with EASI75 continued to increase in all treatment groups over time, except for the vehicle QD group between Weeks 1 and 2. The frequency of application of Tapinarof, QD or BID, had no effect on the main secondary endpoint.

Secondary endpoint analyses using EASI percent change and absolute change over time, maintenance of EASI75, and EASI50 revealed the following: A greater mean percent change reduction in EASI scores from Baseline to each study visit was observed in active treatment groups than in vehicle groups throughout the treatment period. The 1% concentration treatment groups showed a greater mean percentage change reduction than the 0.5% concentration groups in the earlier treatment phase up to Week 4. At Weeks 8 and 12 the improvements were similar in the active treatment groups. Similarly, the increasing mean percent change reduction in EASI scores from Baseline to each study visit was greater in active treatment groups than in vehicle groups for both the adult (all visits) and adolescent (up to Week 4) subjects. Generally, the 1% concentration treatment groups showed a slightly greater mean percentage change reduction than the 0.5% concentration groups, up to Week 8. The EASI evaluation showed a better efficacy at the earlier visits in the 1% QD group than in the 1% BID group in the adolescent subjects. The mean change reductions in EASI scores from Baseline continued to improve over time with a clear difference between active and vehicle groups overall. Both the frequency of application of Tapinarof, QD or BID, and the concentration, 1% or 0.5%, had no effect on this parameter. In the BID active treatment groups and the 1% QD group, there was an increased proportion of subjects who had a >75% improvement in EASI from Baseline to Week 12, with the best maintenance of response at 2 and 4 weeks post-treatment seen in the 0.5% BID group. The 3 groups also showed a more sustained improvement than the 0.5% (QD) concentration group in which similar proportions were seen to the vehicle groups. Specifically, 63% (15 of 24) of subjects in the 1% BID group, 57% of subjects (12 of 21) in the 1% QD group, and 82% (18 of 22) of subjects in the 0.5% BID group maintained response from Week 12 to Week 16. This secondary endpoint result indicates a certain durability of the effect of Tapinarof cream after the 12-week treatment period, and a sustained EASI treatment response. The EASI50 results were consistent with the EASI75 results, except for a stronger vehicle QD response at Week 12.

Ad-hoc Analysis: Eczema Area and Severity Index (EASI): The efficacy data were analyzed using an NRI method to adjust for the higher dropout rates in the vehicle group. With NRI a similar trend was seen for EASI75 to that in the OC analysis: After 1 week of treatment, there was a higher proportion of subjects with >75% improvement in EASI in the active treatment groups than in the vehicle groups. The 1% concentration treatment groups showed a higher rate of responders than the 0.5% concentration groups through to Week 4, but at Weeks 8 and 12 the 0.5% BID group had similar proportions with improved EASI75, using NRI. The adult population demonstrated a consistent trend to the overall population. For adolescent subjects, there was a similar proportion of subjects with EASI75 in the vehicle BID group as in the 1% BID, 1% QD and 0.5% BID groups. However, in the 0.5% QD group the proportion of subjects with EASI75 was lower, and similar to the proportion in the vehicle QD group. The proportion of subjects with EASI75 response continued to increase over time. The frequency of application of Tapinarof, QD or BID, had no effect on EASI75.

Body Surface Area (BSA): A secondary objective was to assess the mean change in % BSA affected from Baseline to each study visit. Overall, most subjects had a reduction in % BSA affected over the study period. An increase in the mean change reduction in % BSA affected from Baseline to each study visit was higher in active treatment groups than in the vehicle groups and the increase improved over time. The frequency of application of Tapinarof, QD or BID, had no effect on the mean change reduction in % BSA affected from Baseline to each study visit. A similar picture was seen in the adult population.

In the adolescent population, the 1% BID and 0.5% BID active treatment groups had greater mean change reductions at Weeks 8 and 12 than the active QD groups; the vehicle BID group had similar mean increases in the mean change reduction to the active QD treatment groups.

Total Severity Score (TSS): A secondary objective of the study was to severity of erythema, induration/papulation, lichenification, oozing/crusting, and scaling), and in the individual signs of TSS, in the individual signs of TSS, from Baseline to each study visit.

Overall, most subjects had a reduction in TSS over the study period. The mean change in TSS from Baseline to each study visit showed an improvement (i.e., reduction) in all treatment groups, but the reduction tended to be larger from Week 2 up to the end of treatment in active treatment groups than in the vehicle groups. In the summaries by age of the mean change in TSS from Baseline to each study visit, this trend was not so marked: in the adult population the vehicle QD group had a similar mean reduction to some of the active treatment groups, and in the adolescent population this pattern was seen with the vehicle BID group.

Itch/Pruritus Severity: A secondary objective of the study was to assess the mean change in weekly itch/pruritus NRS item from Baseline to Week 12.

Overall, most subjects had a decrease in itch/pruritus symptoms over the study period. There was a clear difference in the mean change reduction in itch/pruritus from Baseline to each study visit up to Week 8 between active and vehicle groups; at Week 12, the difference was only apparent for the BID vehicle group; generally this improvement was maintained during the follow-up period. There was no evidence of a dose-related response among the active groups (frequency or concentration). There was also a clear difference between active and vehicle groups from Week 4 through Week 12 in the proportion of subjects who achieved a minimum 3-point improvement in itch/pruritus. These results were supported in the ad-hoc NRI summary. Generally, these differences were also seen in the data by age group, but the response patterns were not always as consistent.

Investigator Impression of Change: As part of the efficacy assessment, investigators' impression of change in AD symptom severity from Baseline to Week 12 were reported. Responses were rated by investigators as "very improved" or "moderately improved" in 80% to 83% of subjects in the 1% concentration groups and 79% to 88% in the 0.5% concentration groups. In the "very improved" category, a clear difference was observed between active treatment groups and vehicle groups.

Summaries by age showed that between 71% and 86% of adult subjects were rated by investigators as "very improved" or "moderately improved" in the active treatment groups compared with less than 70% in the vehicle groups. In the adolescent population, 90% or more were rated by investigators as "very improved" or "moderately improved" in the active treatment groups compared with just over 80% in the vehicle groups.

Subject-Reported Outcomes: One of the other objectives of this study was to describe the effect of Tapinarof cream on the subject-reported impression of severity item, global impression of change items, the expanded POEM, and Daily Sign and Symptom Severity Diary.

Subject Impressions: Subjects provided an overall impression of their severity of eczema as well as their impression of change in eczema symptoms and change in itch.

At Baseline, the majority of subjects in all groups rated their eczema symptoms as moderate or severe; the vehicle BID group had the highest proportion of subjects with severe eczema symptoms. At Week 12, a higher proportion of subjects in the active treatment groups (>80%) rated the severity of their eczema symptoms as "very improved" or "moderately improved" compared with subjects in the vehicle groups (<70%). Similarly, at Week 12 in the Tapinarof groups, 78% or more rated the severity of their itch as "very improved" or "moderately improved" compared with <65% of subjects in the vehicle groups.

Results were similar by age, except for the vehicle BID group, where better ratings were given by the adolescent subjects: 81% were "very improved" or "moderately improved" compared with 53% adult subjects for eczema and 64% versus 36%, respectively, for itch.

Expanded Patient-Oriented Eczema Measure (POEM): The expanded POEM included 7 items plus 3 additional questions to assess sleep quality. Mean Baseline scores were highest (>3 in all treatment groups; indicating 5 or more days per week) for question #1 (relating to itch) and question #7 (relating to dry or rough skin). For questions #1 to #7, there were mean change reductions (improvements) in all active and vehicle groups through Week 12, except for question #4 for the 1% BID group, with the largest mean change reductions generally found in the 0.5% concentration groups. However, this was not consistent for all questions and time points. Standard deviations were large for all treatment groups.

In the adult population, there were mean change reductions in all active and vehicle groups (except question #4) through Week 12 at nearly all visits, but there were no distinct trends across the treatment groups. For most questions and time points, results in the adolescent population were similar to those for the overall population. The mean Baseline scores and the mean change reductions were generally higher in the 0.5% treatment groups than in the other treatment groups in the adolescent population.

An additional 3 questions, not included in the original published instrument, were added to assess sleep quality. For question #8 (how many nights did you wake up at least once because of the eczema?), the mean change reductions were largest in the 0.5% concentration groups (−1.3 and −1.2). For questions #9 (how difficult was it for you to fall asleep because of the eczema?) and #10 (how difficult was it for you to fall back asleep after you had woken up because of the eczema?) the number of subjects finding it difficult or very difficult to fall (back) asleep were lower in all treatment groups at Week 12 compared with Baseline, except for 1 subject in the vehicle BID for question #10. There were mean change reductions (improvements) and fewer subjects having difficulty falling asleep and falling back asleep because of their eczema at Week 12, and in general the largest improvements were in the active treatment groups.

Daily Sign and Symptom Severity Diary Data: One of the other endpoints assessed was the change from Baseline to Week 12 in the weekly average Daily Sign and Symptom Severity Diary score of 11 disease-related symptoms as recorded in the subject diary.

The highest mean Baseline scores were seen for dry or rough skin (range: 6.2 to 6.9), red or discolored skin (range: 4.8 to 6.0), and flaky skin (range: 4.2 to 5.8). For all items there was a reduction in the mean score (i.e., improvement) at Week 12 for all treatment groups. However, no clear differences were observed between the treatment groups, except the reduction was consistently smaller for the vehicle BID group for all items.

Sub-Group Efficacy Analysis: Japanese Population

Out of the 247 subjects randomized in this study, 46 subjects were Japanese. For more details on the demographic and subject baseline characteristics of this subgroup.

Investigator Global Assessment (IGA): In the Japanese population, the primary endpoint analysis, the proportion of subjects who had an IGA score of clear or almost clear (0 or 1) at Week 12 and a minimum 2-grade improvement in IGA score from Baseline to Week 12, showed a numerically higher proportion of subjects in the 1% QD group only. The lowest proportion of subjects with treatment success was in the 0.5% concentration groups, with intermediate responses in the 1% BID group and vehicle groups. With NRI, similar results were obtained, with a clearer separation of both the BID and QD 1% concentration groups from the 0.5% and vehicle groups in IGA treatment success. The highest responder rate was again seen in the 1% QD group. Due to the small number of subjects and large confidence intervals, data should be interpreted with caution.

The proportion of subjects with IGA treatment success in all active treatment and vehicle groups tended to increase over time up to Week 12, with a clear separation observed in the GSK2894512 1% QD treatment group. However, due to low subject numbers the trends were not consistent across treatment groups (e.g., see vehicle QD).

Eczema Area and Severity Index (EASI): A secondary efficacy endpoint, the proportion of subjects with EASI75 from Baseline to each study visit, was consistently higher in the 1% BID and 0.5% BID groups than the vehicle groups in Japanese subjects. EASI showed a more rapid onset of action for active groups versus the vehicle groups; the first response in the vehicle groups was only at Week 4. The 1% QD group showed the most rapid onset of action and highest response rates at Week 1 to Week 4. Due to the small number of subjects and large confidence intervals, data should be interpreted with caution.

There was a trend for a greater mean percent change reduction in EASI scores from Baseline to each study visit in the active treatment groups than in the vehicle groups. The 1% concentration groups showed a greater mean percentage change reduction than the 0.5% concentration groups up to Week 8, inclusive, with the largest reductions in the 1% QD group.

Itch/Pruritus Severity: A secondary objective of the study was to assess the mean change in weekly itch/pruritus from Baseline to Week 12. In the Japanese population, there was separation between active and vehicle groups in the mean change reduction in itch/pruritus at Weeks 2 and 4, but not at other time points, although from Week 2 onwards the lowest mean reduction was consistently seen in the vehicle BID group. For the proportion of subjects who achieved a minimum 3-point improvement in itch/pruritus, there were no clear trends, but the most consistent best response, with approximately 70% of subjects with a response, was seen in the 1% QD group from Week 4 to Week 12. In the ad-hoc NRI, there was a clearer separation between active and vehicle groups and again the highest proportion of responders was seen in the 1% QD group.

Pharmacokinetics: Subjects with atopic dermatitis, BSA involvement >5% and <35%, excluding scalp, and Baseline IGA score of >3 at Baseline, participated in this study in which 2 concentrations of Tapinarof cream (0.5% and 1%) and a vehicle control were evaluated following application to all AD lesions (except on the scalp) once or twice daily for 12 weeks.

A total of 5 blood samples for PK analysis of Tapinarof were collected from each subject at the following clinic visits: Weeks 1, 2, 4, 8, and 12. Subjects were advised to provide PK samples during each of the following 3 time windows: 1 to 3 hours post application, 3 to 6 hours post application, and 6 to 12 hours post application.

Of the 753 plasma samples obtained from subjects on active treatment, 348 plasma samples were quantifiable (lower limit of quantification [LLOQ]=0.04 ng/mL).

Overall, limited Tapinarof PK data are available in AD patients to date. Intensively sampled PK data are only available in AD patients (n=6) from Study 201851 Cohort 2 (1% cream BID); hence, the central tendency and variability in the PK of Tapinarof are not well defined. Given the PK data limitations, no definitive conclusions on Tapinarof PK from Study 203121 can be made at the current time and therefore the data should be interpreted with caution. Therefore, comparison of PK across relevant subpopulations (adults, adolescents, Japanese) is not included.

Plasma Concentration Outliers: Elevations in plasma concentrations (>0.84 ng/mL gender averaged NOAEL Cmax of minipig 28 day, formulation F, 3% [60 mg/kg/day]) were observed in 13 out of 247 (5%) subjects. For all subjects, outlier plasma concentrations were measured at a single time point and all other plasma concentrations sampled in the same patient were below the NOAEL. Among these subjects, there was no relationship between the occurrence of high plasma concentration and timing of AE(s). Reported AEs in these subjects were consistent with the system organ class, frequency, and severity of AEs reported across the Tapinarof Phase 2 studies. All 13 subjects (5 males, 8 females; aged between 12 and 65 years [3 in the adolescent population, 10 in the adult population]), were in the Tapinarof treatment groups. Elevations in plasma concentration were observed in subjects in each of the different treatment groups without evidence of a dose effect (2 subjects from the 0.5% QD group [2/13, 15%], 4 subjects from the 0.5% BID group [4/13, 31%], 2 subjects from the 1% QD group [2/13, 15%], and 5 subjects from the 1% BID group [5/13, 38%]. Nine out of the 13 (69%) subjects experienced AEs: arthralgia, rash, application site pain, local reaction, diarrhea, dizziness, impetigo, blood creatinine decreased, conjunctivitis, dermatitis atopic, superinfection, application site reaction, hyperbilirubinemia, nasopharyngitis, sycosis barbae, and folliculitis. AEs of application site pain and folliculitis were observed in more than 1 subject. Overall, the median time to onset (since Day 1) for these events was 41 days with a median duration of 9 days. The majority of the events were mild to moderate. Four subjects (4/13, 31%) had AEs (rash, local reaction, application site pain, application site reaction, folliculitis) which were considered treatment-related by the investigator. None of the subjects experienced an SAE. Despite a thorough investigation of relevant patient information at the study sites, no root cause was identified that could explain the elevated plasma concentrations. The elevated plasma concentrations of the aforementioned subjects are presumably spurious. Plasma concentrations will continue to be monitored in PK studies.

Subject 110406, a 14-year-old female in the Tapinarof 1% BID group experienced mild AEs of arthralgia on Day 1, rash on Day 23, and application site pain on Day 38, and local reaction on Day 68. A drug interruption (reason: study drug not tolerated) occurred between Day 29 to Day 48 and again from Day 65 to Day 78. PK samples were obtained from this subject at Weeks 1, 2, 4, 8, and 12 with concentration values at 0.233, 0.347, 4.9, 0.514, and no quantifiable level—below the limit of quantification (NQ) ng/mL, respectively. The investigator considered the events of rash, application site pain, and local reaction were related to study treatment and the event of arthralgia was unrelated to study treatment.

Subject 111301, a 12-year-old male in the Tapinarof 0.5% BID group experienced severe AEs of dermatitis atopic on Day 65, superinfection on Day 65, and application site reaction on Day 1 and Day 70. PK samples were obtained from this subject at Weeks 1, 2, and 4 with concentration values at 6.09, 0.438, and 0.649 ng/mL, respectively. The subject had withdrawn treatment on Day 64 and discontinued from the study on Day 69, due to investigator discretion. The Week 1 plasma concentration exceeded the NOAEL Cmax value; however, subsequent plasma samples at Weeks 2 and 4 were below the NOAEL. The investigator considered the events of application site reaction were related to study treatment and the events of dermatitis and superinfection were unrelated to study treatment.

No other subjects with plasma concentrations above the NOAEL had treatment interruptions or withdrew from the study. Plasma concentrations and AEs will continue to be monitored in subsequent studies.

The narratives described below are subjects with plasma concentrations above the NOAEL and experienced a systemic AE.

Subject 110604, a 21-year-old female in the Tapinarof 1% BID group experienced moderate AEs of diarrhea and dizziness on Day 14, and impetigo on Day 15. PK samples were obtained from this subject at Weeks 1, 2, 4, 8, and 12 with concentration values at 1.48, 0.266, 0.430, 0.0716, and 0.311 ng/mL, respectively. The investigator considered the events were unrelated to study treatment.

Subject 316651, a 27-year-old male in the Tapinarof 1% BID group experienced a mild AE of blood creatinine decrease on Day 87. PK samples were obtained from this subject at Weeks 1, 2, 4, 8 and 12 with concentration values at NQ, 181.0, NQ, NQ and NQ ng/mL, respectively. The investigator considered the event was unrelated to study treatment.

Subject 316851, a 20-year-old male in the Tapinarof 0.5% BID group experienced a mild AE of hyperbilirubinemia on Day 102. PK samples were obtained from this subject at Weeks 1, 2, 4, 8 and 12 with concentration values at 0.362, 0.106, NQ, 1.93, and NQ ng/mL, respectively. The investigator considered the event was unrelated to study treatment.

Safety Results

Safety results are reported using the Safety Population. Unless mentioned otherwise, results reported in this section are those of the overall population.

Adverse Events: Treatment-emergent adverse events (TEAEs) were reported in 127 subjects (51%) (the Safety Population comprised 247 subjects). The frequency of TEAEs was higher in the active treatment groups than in the vehicle groups (93 subjects [56%] vs 34 subjects [41%]).

Overall, TEAEs were considered treatment-related in 32/247 subjects (13%). There was a higher proportion of subjects in the active treatment groups than in the vehicle groups with treatment-related TEAEs (24/165 [15%] vs 8/82 [10%]). Thirteen of 247 (5%) subjects permanently discontinued treatment due to TEAEs (7/165 [4%] in the active treatment groups vs 6/82 [7%] in the vehicle groups). One (<1%) subject experienced serious TEAEs (reported from the active treatment group). Most TEAEs were reported as mild (53/165 [32%] in the active treatment groups vs 19/82 [23%] in the vehicle groups) or moderate (36/165 [22%] in the active treatment groups vs 12/82 [15%] in the vehicle groups). Seven (3%) subjects overall experienced severe TEAEs (4/165 [2%] in the active treatment groups vs 3/82 [4%] in the vehicle groups). No treatment-related serious or fatal TEAEs were reported.

In the adult subjects, TEAEs were considered treatment-related in 22/174 subjects (13%); most of these subjects were in the active treatment groups compared with vehicle groups (16/116 [14%] vs 6/58 [10%]). Nine of 174 (5%) subjects permanently discontinued treatment due to TEAEs (4/116 [3%] in the active treatment groups vs 5/58 [9%] in the vehicle groups). No subject experienced serious TEAEs. Most TEAEs were reported as mild (33/116 [28%] in the active treatment groups vs 13/58 [22%] in the vehicle groups) or moderate (29/116 [25%] in the active treatment groups vs 9/58 [16%] in the vehicle groups). Five (3%) subjects in the 18 to 65 years age group experienced severe TEAEs (3/116 [3%] in the active treatment groups vs 2/58 [3%] in the vehicle groups). No treatment-related serious or fatal TEAEs were reported.

In the adolescent subjects, TEAEs were considered treatment-related in 10/73 subjects (14%); most of these subjects were in the active treatment groups compared with vehicle groups (8/49 [16%] vs 2/24 [8%]). Four of 73 (5%) subjects permanently discontinued treatment due to TEAEs (3/49 [6%] in the active treatment groups vs 1/24 [4%] in the vehicle groups). One (1%) subject experienced serious TEAEs (reported from the active treatment group). Most TEAEs were reported as mild (20/49 [41%] in the active treatment groups vs 6/24 [25%] in the vehicle groups) or moderate (7/49 [14%] in the active treatment groups vs 3/24 [13%] in the vehicle groups). Two (3%) subjects in the 12 to 17 years age group experienced severe TEAEs (1/49 [2%] in the active treatment groups vs 1/24 [4%] in the vehicle groups). No treatment-related serious or fatal TEAEs were reported.

In Japanese subjects, TEAEs were considered treatment-related in 5/46 subjects (11%); all of these subjects were in the active treatment groups (5/30 [17%]). One of 46 (2%) subjects permanently discontinued treatment due to TEAEs (1/30 [3%] in the active treatment groups). No subject experienced serious TEAEs. Most TEAEs were reported as mild (15/30 [50%] in the active treatment groups vs 5/16 [31%] in the vehicle groups) or moderate (3/30 [10%] in the active treatment groups vs 2/16 [13%] in the vehicle groups). No Japanese subjects experienced severe TEAEs and no treatment-related serious or fatal TEAEs were reported.

The most frequently reported TEAE was nasopharyngitis, which occurred in 20/247 subjects (8%) (13/165 [8%] in the active groups vs 7/82 [9%] in the vehicle groups). Other TEAEs reported in >5% of subjects in any arm or in total were: folliculitis, reported in 18 subjects (7%) (18/165 [11%] in the active groups vs 0 in the vehicle group), atopic dermatitis in 15 subjects (6%) (6/165, [4%] in the active groups vs 9/82 [11%] in the vehicle groups), upper respiratory tract infection, reported in 15 subjects (6%) (11/165 [7%] in the active groups vs 4/82 [5%] in the vehicle groups), headache, reported in 11 subjects (4%) (9/165 [5%] in the active groups vs 2/82 [2%] in the vehicle groups), acne, reported in 7 subjects (3%) (6/165 [4%] in the active groups vs 1/82 [1%] in the vehicle groups), and impetigo, reported in 4 subjects (2%) (1/165 [1%] in the active groups vs 3/82 [4%] in the vehicle groups). The TEAEs of atopic dermatitis were reported as AD flare, worsening of AD, aggravation of AD, or increased itching of AD.

In Japanese subjects, nasopharyngitis and folliculitis were also the most frequently reported TEAEs.

Overall, 32 subjects (13%) had TEAEs which were considered treatment-related by the investigators. The frequency was higher in the active treatment groups compared to the vehicle groups (24/165 [15%] in the active treatment groups vs 8/82 [10%] in the vehicle groups). Folliculitis was the most frequent TEAE which was considered treatment-related by the investigators; it was reported in 9 subjects (4%), (9/165 [5%] in the active treatment groups vs 0% in the vehicle groups). Of these, all subjects with TEAEs which were considered treatment-related by the investigator were similarly distributed across the Tapinarof treatment groups, concentration 0.5% or 1% and frequency (BID or QD). Application site pain, was the next most frequent TEAE which was considered treatment-related by the investigators; it was reported in 5 subjects (2%), (2/165 [1%] in the active treatment groups vs 3/82 [4%] in the vehicle groups). Of these, 1 subject was in the Tapinarof 1% group and 1 subject in the 0.5% group, both on a frequency of BID. In the vehicle arm, 2 subjects were on a frequency of BID and 1 subject was on QD.

The following TEAEs which were considered treatment-related by the investigators were each reported in 3 subjects (1%) or less: eczema impetiginous, herpes simplex, upper respiratory tract infection, atopic dermatitis, acne, contact dermatitis, dermal cyst, dry skin, hyperkeratosis follicularis et parafollicularis, pain of skin, rash, application site reaction, application site erythema, application site edema, application site pruritus, local reaction, headache, burning sensation, hypoesthesia, diarrhea, nausea, increased hepatic enzyme, and decreased monocyte count.

In the adult and adolescent populations, the following treatment-related TEAEs were reported in both populations: application site pain, application site reaction, acne, atopic dermatitis, folliculitis, and headache. The incidence of these events was similar in the 2 populations, except for application site pain which was more frequently reported in adolescent subjects (5% overall) than in adult subjects (1%).

In the Japanese population, TEAEs related to study treatment were reported in the active treatment groups but a dose-response relationship was not observed.

Overall, TEAEs led to permanent discontinuation of study treatment in 13 subjects (5%). The frequency was higher in the vehicle groups than the active treatment groups (6/82 [7%] in the vehicle groups vs 7/165 [4%] in the active treatment groups). Atopic dermatitis (reported as worsening or flare of AD—see source Listing 39) was the most frequent TEAE that led to study treatment discontinuation; it was reported in 8 subjects (3%), (4/165 [2%] in the active treatment groups vs 4/82 [5%] in the vehicle groups). Of these, all subjects with TEAEs that led to study treatment discontinuation in the active treatment arms were treated with the lower concentrations of cream; 3 subjects (7%) with Tapinarof cream 0.5% BID and 1 subject (2%) with Tapinarof cream 0.5% QD.

In Japan, TEAEs led to permanent discontinuation of study treatment in 1 subject (2%) in the Tapinarof 0.5% BID group. Subject 317102, a 57-year-old female experienced non-serious events of application site edema, burning sensation, and contact dermatitis. All the events started 30 days after the first dose and 1 day after the last dose.

The events occurred on the application site and were considered moderate in intensity. The study treatment was withdrawn and all events resolved 14 days after onset. The investigator considered all 3 events to be related to study treatment.

Serious and Other Significant Adverse Events

Deaths: No deaths were reported during the study.

Other Serious Adverse Events: Serious TEAEs were reported in 1 subject (<1%), who was in the Tapinarof treatment group. Brief summaries of these serious TEAEs are provided below.

Anxiety and attention deficit/hyperactivity disorder: A 14-year-old male with a previous history of anxiety and attention deficit/hyperactivity disorder was randomized to receive Tapinarof 1% BID. The subject was hospitalized due to anxiety and attention deficit/hyperactivity disorder 55 days after the first application and 3 days after the last application. Study treatment was withdrawn and events resolved 10 days later. The investigator considered the events were unrelated to study treatment.

Other Significant Adverse Events: No other significant AEs were reported during the study. However, a summary of the details of the 5 most frequently reported AEs is provided below. The summaries by age showed similar results to those seen in the overall population.

Nasopharyngitis: A total of 20 out of 247 (8%) subjects (11 males, 9 females; aged between 13 and 49 years) experienced nasopharyngitis, 13 of whom (13/20, 65%) were from active treatment groups. The events were reported in 5 subjects from the GSK2894512 1% QD group (5/20, 25%), 4 from the 0.5% BID group (4/20, 20%), 3 from the 1% BID group (3/20, 15%), 1 from the 0.5% QD group (1/20, 5%), and 7 from the vehicle groups (7/20, 35%). The majority of the events were of mild intensity (18/20, 90%) and 2 (2/20, 10%) were considered moderate in intensity. No subjects had treatment withdrawn due to the event. All but 2 of the cases were considered recovered or resolved at the time of reporting. The median time to onset (since Day 1) was 43 days (32 days in the active treatment groups and 52 days in the vehicle groups). The median duration of the event was 8 days (9 days for the active treatment groups and 5 days for the vehicle groups). None of the events were considered related to study treatment by the investigators.

In the adult population, 12 subjects (12/174, 7%) experienced nasopharyngitis, 4 (33%) in the 1% QD group, 2 each (17%) in the 1% and 0.5% BID groups, and 4 (33%) in the vehicle groups. The median time to onset was 32 days in the active treatment groups with a median duration of 9 days. In the vehicle groups the median time to onset was 73.5 days and the median duration 4 days.

In the adolescent population, 8 subjects (8/73, 11%) experienced nasopharyngitis: 2 (25%) in the 0.5% BID group, 1 each (12.5%) in the 1% BID, 1% QD and 0.5% QD groups, and 3 (37.5%) in the vehicle groups. The median time to onset was 31 days in the active treatment groups and 51 days in the vehicle groups, with a median duration of 9 days in both cases.

Folliculitis: A total of 18 out of 247 (7%) subjects (8 males, 10 females; aged between 12 and 49 years), experienced folliculitis, all from the active treatment groups. Most of these events were reported from the Tapinarof 1% QD group (8/18, 44%). A majority of the events were mild (13/18, 72%) and the rest were considered moderate (5/18, 28%). No severe events were reported. No subject had treatment withdrawn due to the event. Most (10/18, 56%) of the events occurred at the study drug application site. The median start date (since Day 1) of folliculitis was Day 17. The majority of these events were ongoing/resolving (11 ongoing/resolving and 7 resolved) at the end of the study follow-up period. Therefore, the AE end dates are not provided in many subjects, indicating that the AE was not resolved at the end of the follow-up period in those subjects. Half (9/18, 50%) of the subjects had events of folliculitis considered related and the other half were considered not related to study treatment by the investigators.

In the adult population, 14 subjects (14/174, 8%) experienced folliculitis, all in the active treatment groups: 6 subjects (430%) in the 10% QD group, 3 (21%) each in the 1% BID and 0.5% QD groups, and 2 (14%) in the 0.5% BID. The median time to onset was 17 days.

In the adolescent population, 4 subjects (3/73, 5%) experienced folliculitis: 2 (50%) in the 1% QD group, 1 each (25%) in the 1% BID and 0.5% BID groups, and none in the vehicle groups. The median time to onset was 23.5 days.

Atopic Dermatitis: A total of 15 out of 247 (6%) subjects (10 males, 5 females; aged between 12 and 59 years) experienced a worsening or flare of atopic dermatitis, 6 of whom (6/15, 40%) were from active treatment groups. The events were reported in 9 subjects from the vehicle group (9/15, 60%), 2 from the Tapinarof 1% BID group (2/15, 13%), 3 from the 0.5% BID group (3/15, 20%), and 1 from the 0.5% QD group (1/15, 7%). A majority of the events were of moderate intensity (9/15, 60%), 2/15 (13%) were considered mild, and 4/15 (27%) were considered severe. Eight subjects (8/15, 53%) had treatment withdrawn and 3 subjects (3/15, 20%) had treatment interrupted due to the event. Six subjects (6/15, 40%) had ongoing events at the time of reporting and the rest were resolving/resolved. Seven subjects (7/15, 47%) had events which occurred at the study drug application site. The median time to onset (since Day 1) was 21 days (40.5 days in the active treatment groups and 12 days in the vehicle groups). The median duration of the event was 8.5 days (12.5 days for the active treatment groups and 8 days for the vehicle groups). Three subjects (3/15, 20%) had events which were considered related to study treatment by the investigators.

In the adult population, 12 subjects (12/174, 7%) experienced atopic dermatitis, 2 (17%) in the 1% BID group, 1 each (8%) in the 0.5% BID and QD groups, and 4 each (33%) in the vehicle BID and QD groups. The median time to onset was 40.5 days in the active treatment groups with a median duration of 22.5 days. In the vehicle groups the median time to onset was 9 days and the median duration 8 days.

In the adolescent population, 3 subjects (3/73, 4%) experienced atopic dermatitis: 2 (67%) in the 0.5% BID group and 1 (33%) in the vehicle QD group. The median time to onset was 34 days in the active treatment group with a median duration of 6.5 days, the event in the vehicle group started 68 days after Day 1 and lasted 17 days.

Upper Respiratory Tract Infection: A total of 15 out of 247 (6%) subjects (10 males, 5 females; aged between 14 and 59 years) experienced upper respiratory tract infection, 11 of whom (11/15, 73%) were from active treatment groups. The events were reported in 4 subjects from the Tapinarof 1% BID group (4/15, 27%), 2 from the 1% QD group (2/15, 13%), 3 from the 0.5% BID group (3/15, 20%), and 2 from the 0.5% QD group (2/15, 13%). The majority of the events were of mild intensity (10/15, 67%) and the rest (5/15, 33%) were considered moderate. No subjects had treatment withdrawn due to the event. Two events were ongoing and the rest were considered resolved at the time of reporting. The median time to onset (since Day 1) was 32.5 days (32.5 days in the active treatment groups and 29.5 days in the vehicle groups). The median duration of the event was 11.5 days (16.5 days for the active treatment groups and 10.5 days for the vehicle groups). Only 1 of these events was considered related to study treatment by the investigator.

In the adult population, 13 subjects (13/174, 7%) experienced upper respiratory tract infection, 4 (31%) in the 1% BID group, 3 (23%) in the 0.5% BID group, 2 (15%) in the 1% QD group, 1 (8%) in the 0.5% QD group, and 3 (23%) in the vehicle groups. The median time to onset was 38 days in the active treatment groups with a median duration of 22 days. In the vehicle groups the median time to onset was 9 days and the median duration 9 days.

In the adolescent population, 2 subjects (2/73, 3%) experienced upper respiratory tract infection, 1 (50%) in the 0.5% QD group and 1 (50%) in the vehicle BID group. The time to onset was 8 days in the active treatment group with a duration of 6 days, the event in the vehicle group started 50 days after Day 1 and lasted 12 days.

Headache: A total of 11 out of 247 (4%) subjects (6 males, 5 females; aged between 14 and 41 years) experienced headache, 9/11 (82%) from active treatment groups and 2/11 (18%) from vehicle groups. The most events of headache were reported in subjects in the Tapinarof 1% BID group (4/11 [36%]). The majority of subjects had events (8/11, 73%) that were of mild intensity and the rest (3/11, 27%) were considered moderate in intensity. One subject (1/11, 9%) had treatment withdrawn due to the event. All, except 1 event, were considered resolved at the time of reporting. The median time to onset (since Day 1) was 3 days (2 days in the active treatment groups and 52 days in the vehicle groups). The median duration of the event was 1.5 days (2 days for the active treatment groups and 1 day for the vehicle groups). Three of the events were considered related to study treatment by the investigators.

In the adult population, 9 subjects (9/174, 5%) experienced headache: 3 (33%) in the 1% BID group, 2 (22%) subjects in the 0.5% QD group, and 1 each (11%) in the 1% QD and the 0.5% BID groups, and 2 (22%) in the vehicle QD group. The median time to onset was 3 days in the active treatment groups with a median duration of 2 days. In the vehicle group the median time to onset was 52 days and the median duration 1 day.

In the adolescent population, 2 subjects (2/73, 2%) experienced headache: 1 each (50%) in the 1% BID and 0.5% QD groups, and none in the vehicle groups. The median time to onset was 1 day in the active treatment groups with a median duration of 2 days.

Clinical Laboratory Evaluations: Elevations in liver chemistries (ALT/aspartate aminotransferase [AST] >2×ULN) were seen in 6 subjects, all in Tapinarof treatment groups. The elevations did not trigger protocol-mandated liver stopping criteria, the subjects all continued treatment, and all elevations resolved. Plasma concentrations for these subjects were reviewed to determine if any relationship with systemic exposure and/or timing of liver chemistry elevations existed; no relationships were observed.

Seven subjects had laboratory-related AEs which are presented below:

Subject 317101, a 12-year-old male, in the Tapinarof 0.5% BID group had a mild non-serious AE of decreased monocyte count (0.07 G/L). The event started 97 days after the first application and 15 days after the last application, during the follow-up period. The event of decreased monocyte count was ongoing at the time of reporting. The investigator considered the event was related to study treatment.

Subject 316651, a 27-year-old male, in the Tapinarof 1% BID group had a mild non-serious AE of blood creatinine decreased (63.6 μmol/L). The event started 87 days after the first application and 3 days after the most recent application. The study drug dose was not changed and the event resolved 15 days after onset (value of 70.7 μmol/L). The investigator considered the event was unrelated to study treatment.

Subject 316652, a 22-year-old male, in the vehicle BID group had a mild non-serious AE of blood creatinine decreased (61.9 μmol/L). The event started 29 days after the first application and 2 days after the most recent application. The study drug dose was not changed and the event resolved 75 days after onset (value of 69 μmol/L). The investigator considered the event was unrelated to study treatment.

Subject 316851, a 20-year-old male, in the Tapinarof 0.5% BID group had a mild non-serious AE of hyperbilirubinemia (42 μmol/L). The event started 102 days after the first application and 18 days after the last application. The event was ongoing at the time of reporting. The investigator considered the event was unrelated to study treatment.

Subject 110360, a 19-year-old female, in the Tapinarof 1% BID group had a moderate non-serious AE of alanine aminotransferase increased (183 IU/L). Her AST value was also >6×ULN (590 IU/L) at the time of the event. The event started 58 days after the first application. The study drug dose was not changed and the event resolved 11 days after onset (ALT 18 IU/L and AST 23 IU/L). The investigator considered the event was unrelated to study treatment.

Subject 110202, a 41-year-old female, in the Tapinarof 0.5% QD group had a mild non-serious AE of transaminases increased (ALT 91 IU/L, AST 44 IU/L). The event started 15 days after the first application and 1 day after the most recent application. The study drug dose was not changed and the event resolved 14 days after onset (ALT 16 IU/L, AST 15 IU/L). The investigator considered the event was unrelated to study treatment.

Subject 111103, a 19-year-old male, in the Tapinarof 0.5% BID group had a mild non-serious AE of increased hepatic enzyme (ALT 89 IU/L, AST 75 IU/L). The event started 16 days after the first application and 1 day after the most recent application. The study drug dose was not changed due to this event and the event resolved 28 days after onset (ALT 17 IU/L, AST 30 IU/L). The investigator considered the event was related to study treatment.

Other Safety Evaluations: Overall, there were no clinically significant changes in vital signs during the study. Overall, 10 subjects (4%) had systolic blood pressure readings, 6 subjects (2%) had diastolic blood pressure readings, and 3 subjects (1%) had pulse rates which were of potential clinical importance, but no corresponding related AEs were reported.

A total of 49 subjects (20%) had abnormal clinically significant ECGs at any post-screening visit during the study. Of these, more subjects were in the 1% treatment groups (12 subjects [30%] were in the Tapinarof 1% BID group and 10 subjects [24%] in the Tapinarof 1% QD), compared to 5 subjects (12%) in the Tapinarof 0.5% BID group and 8 subjects (21%) in the Tapinarof 0.5% QD group. However, the incidences in the vehicle groups were also similar to the active groups (5 subjects [12%] in the vehicle BID group and 9 subjects [23%] in the vehicle QD group).

Tolerability Evaluations by Subjects and Investigators: One of the secondary objectives of the study was to describe the tolerability of Tapinarof cream as assessed by the investigator and subject measuring local (application site) tolerability scores over time as a secondary endpoint.

No difference in subject-reported tolerability scores was apparent between the 2 Tapinarof cream concentrations (0.5% and 1%) or between the 2 frequencies of application (QD or BID) tested. Tolerability scores improved during the course of the study. The proportion of subjects with the best tolerability score (score 0 or "none") increased from Week 1 to Week 12 across all study treatment groups.

In total, investigators assessed most subjects (>70%) as having the lowest irritation score (0 or "no irritation") from Week 1 onwards. By treatment group, the lowest proportion of subjects with "no irritation" tended to be seen in the 1% BID group and the vehicle QD group.

Pregnancies: No pregnancies were reported during the study.

Immunoglobulins and Immunophenotyping: No clinically-significant changes were observed for either the adult or the adolescent populations in immunoglobulins (IgA, IgG, and IgM) across all treatment groups receiving either Tapinarof or vehicle and regardless of dosing frequency.

No clinically-significant changes were observed for either the adult or the adolescent populations in immunophenotyping across all treatment groups receiving either Tapinarof or vehicle regardless of dosing frequency.

Health Outcomes

One of the objectives of this study was to describe the effect of Tapinarof cream on subject-reported outcomes, for which subjects completed a Subject Impression of Severity and Change questionnaire, the expanded POEM, and the Daily Sign and Symptom Severity Diary (including the NRS itch/pruritus item).

Discussion and Conclusions

Discussion

The objective of this randomized, double-blind, vehicle controlled Phase II study was to evaluate the efficacy and safety of two doses of Tapinarof/GSK4985212 cream (0.5% or 1%) applied either QD or BID in adolescent and adult subjects with AD over a 12-week treatment period. The characterization of population PK of Tapinarof cream after topical application was also an objective of the study.

Study population: The population enrolled in this study was consistent with a moderate to severe AD patient population. Specifically, subjects had a mean Baseline IGA score of 3.1 and 3.0 in the overall and the Japanese populations, respectively. Demographic and Baseline characteristics were generally similar across treatment groups. Withdrawal rates were higher in the 2 vehicle groups (>30%) than the 4 active treatment groups (12% to 28%).

Efficacy Discussion

Overall: Treatment success rates at Week 12 were: 53% [1% BID]; 46% [1% QD]; 37% [0.5% BID]; 59 34% [0.5% QD]; 24% [vehicle BID]; 28% [vehicle QD]. The rate (53%) of 1% BID was statistically significantly higher than (24%) vehicle BID. Treatment success was maintained for 4 weeks after end of tapinarof treatment. Treatment-emergent adverse events (TEAE) were higher with tapinarof (93/165; 56%) vs. vehicle (34/82; 41%) and mild-to-moderate in intensity.

The primary analysis showed a separation between 3 of the active treatment groups (1% BID, 1% QD, and 0.5% BID) and the vehicle groups with regards to the primary endpoint (proportion of subjects who achieved an IGA score of 0 or 1 at Week 12 and a minimum 2-grade improvement in IGA score from Baseline to Week 12). FIG. 1 demonstrates Tapinarof 1% showed statistical significance over vehicle after 4 weeks of treatment at multiple time points. Generally, an increase in IGA treatment success could be seen in all groups by Week 2, with separation of active from vehicle at Week 4. The proportion of subjects with IGA treatment success then tended to increase in magnitude up to Week 12, with the 1% concentration groups having a higher proportion of responders at each time point compared to the 0.5% concentration groups. The only exception to this was in the QD active groups, where the proportion improved to Week 8 and then decreased slightly at Week 12. After the end of treatment the proportion of subjects with IGA treatment success started to decrease again in all groups.

The secondary endpoint of the proportion of subjects with EASI75 from Baseline to each study visit was higher in all 4 active treatment groups than in the vehicle groups from Week 2, with the clearest difference seen with the same 3 active treatment groups (1% BID, 1% QD, and 0.5% BID) as was seen for the primary endpoint. The maintenance of response in the 4 weeks after the end of treatment was also improved in the BID groups compared with vehicle.

Mean percent change reduction in EASI scores from Baseline to each study visit was higher in active treatment groups than in vehicle groups throughout the treatment period. Similar improvement over time was observed for the mean percent change reduction in EASI scores for both 1% concentration groups (BID and QD), leading to the conclusion that the QD application had similar efficacy level to BID and would provide lower exposure than BID; therefore, it should be chosen for future Phase III studies. Also, the QD application offers an ease of use advantage that could lead to future subject treatment adherence.

Figure 2:
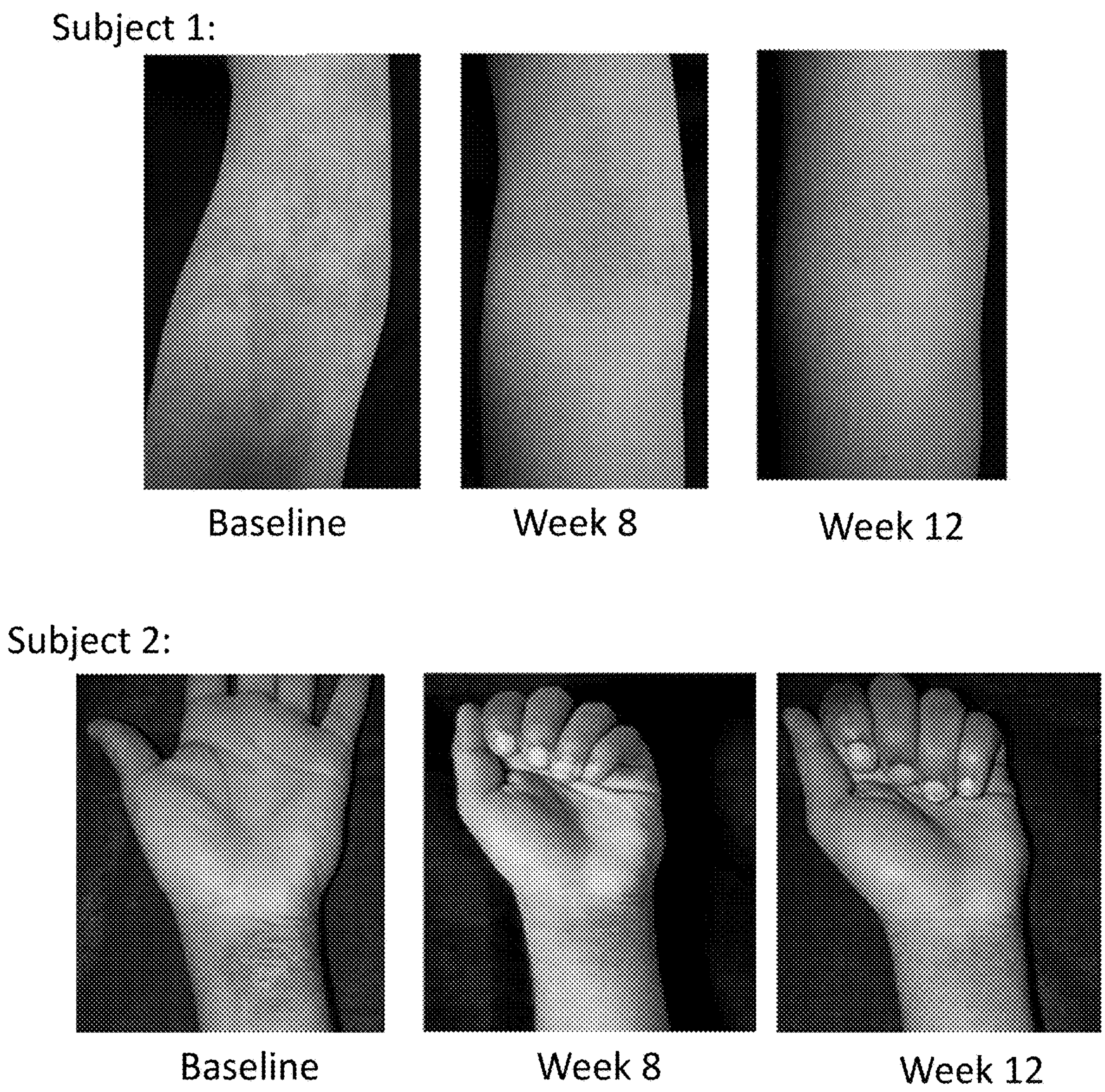
FIG. 2 shows the clinical feature of two patients with atopic dermatitis who received tapinarof (1% QD).
Figure 3:
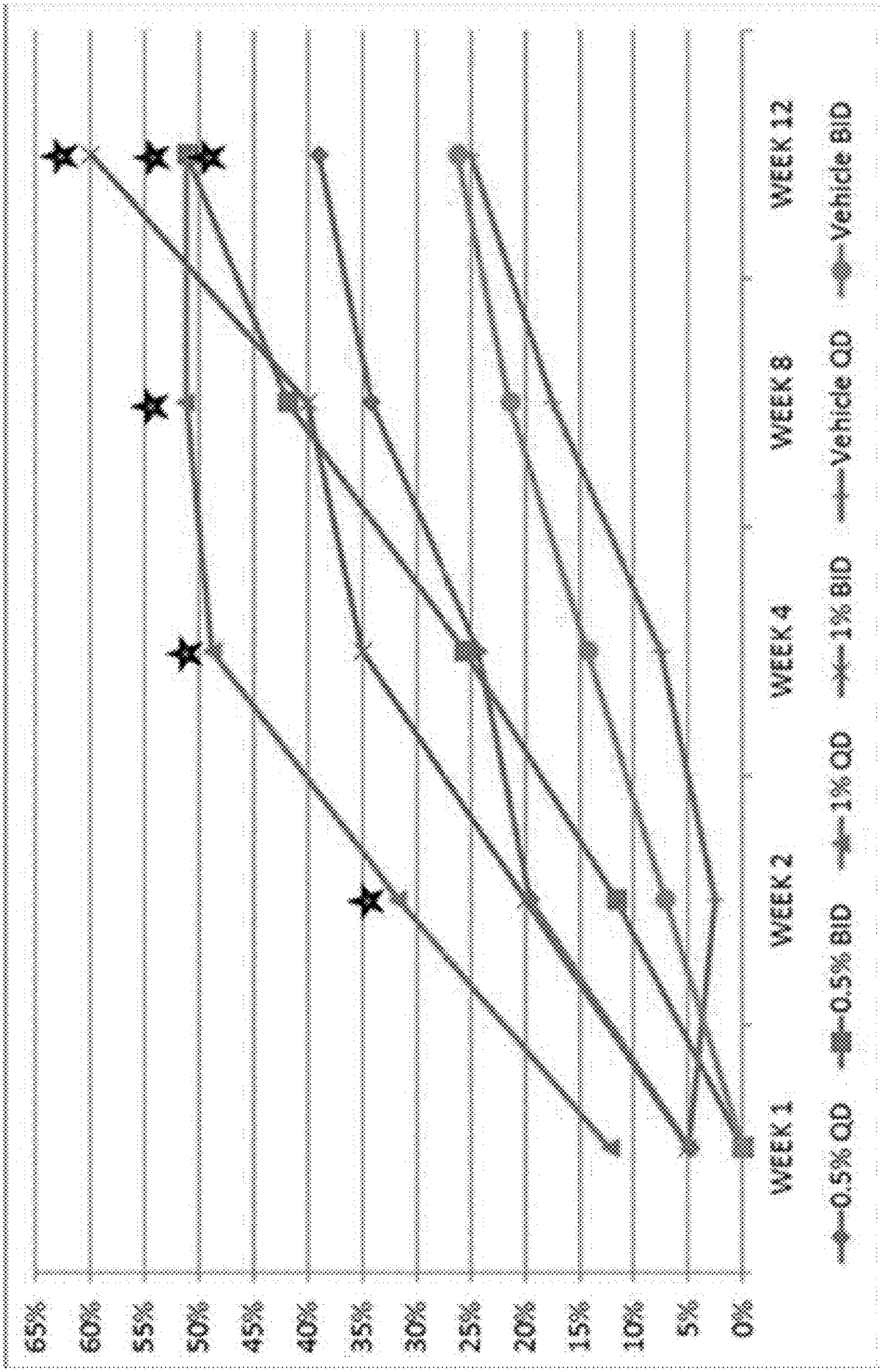
FIG. 3 demonstrates that the Tapinarof 1% QD concentration demonstrated statistical significance (*) over the vehicle at $\alpha$=0.05 level after two weeks of treatment.

FIG. 2 provides photographs which demonstrate improvement in IGA and EASI at Weeks 8 and 12. FIG. 3 provides a graphical depiction of the proportion of patients with greater than or equal to 75% improvement in EASI (EASI75) from baseline (EASI75) at each study visit using non-responder imputation.

The frequency of application of Tapinarof, QD or BID, had no clear effect on the primary or main secondary endpoints.

Generally the adult population demonstrated a pattern consistent to that of the overall population with regard to efficacy endpoints: the primary endpoint analysis showed a higher proportion of subjects responded in the active treatment groups than the vehicle groups. For EASI75 and mean reduction in % BSA the response patterns were also consistent. In the adolescent population, patterns differed somewhat, with stronger responses seen in the vehicle BID group compared with the other populations across the efficacy endpoints, but due to the smaller sample size of this population, the data should be interpreted with caution.

To adjust for the higher dropout rates in the vehicle group, the efficacy data were reanalyzed after unblinding using NRI method. Overall, with this method, the aforementioned efficacy results were unaltered, confirming the robustness of the data. In addition, the efficacy results showed a clear separation between each of the doses of the active treatment and the vehicle groups with each the active groups showing a higher response rate than the vehicle groups at Week 12.

Figure 4:
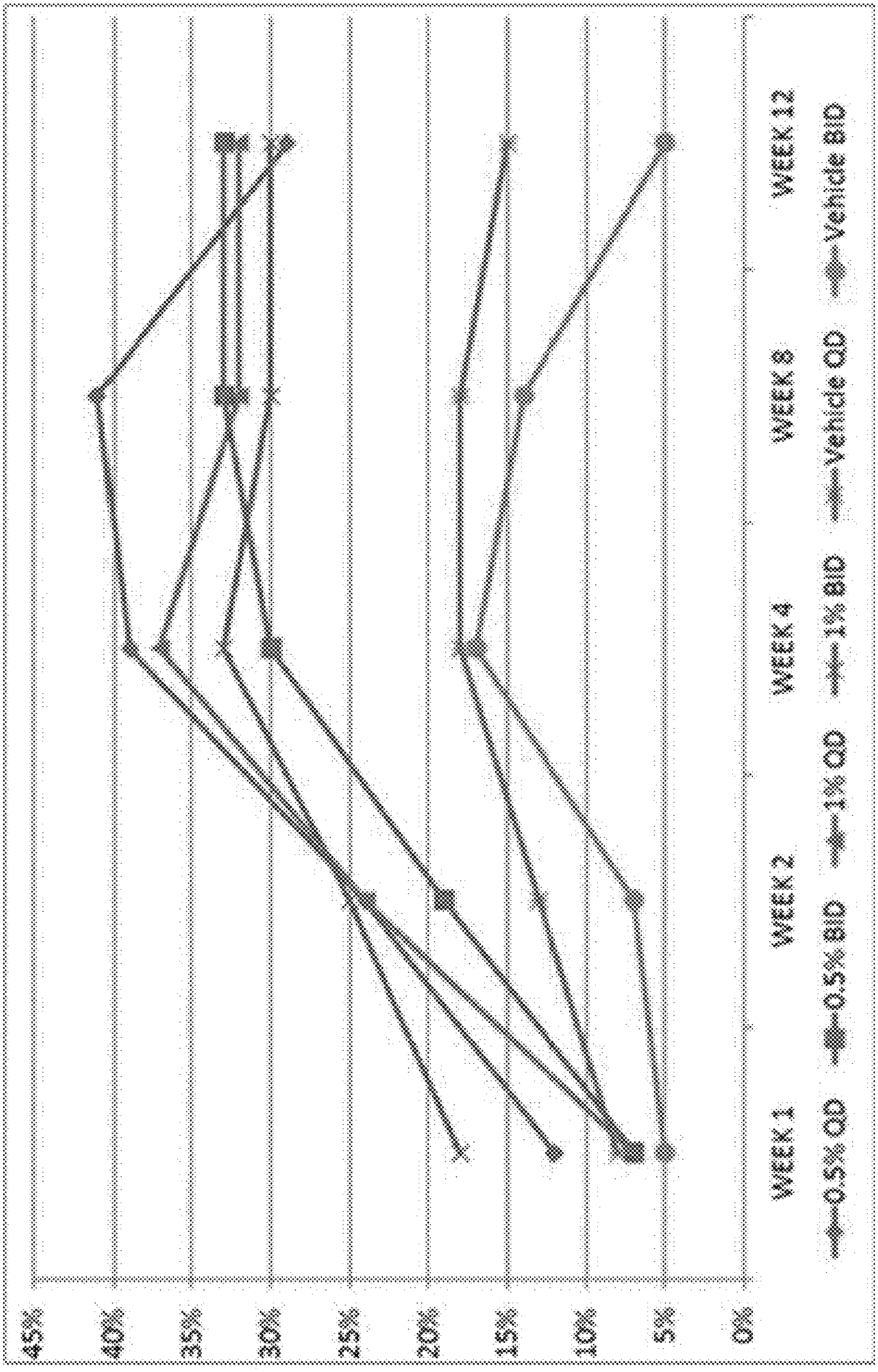
FIG. 4 demonstrates that a difference can be seen after 2 weeks in the tapinarof groups compared to the vehicle groups.

Results from other clinical evaluations assessed from Baseline to each study visit such as mean change reduction in % BSA affected and TSS, and reduction in itch/pruritus symptoms were also supportive of the therapeutic effect of Tapinarof cream, as compared to vehicle. FIG. 4 graphically depicts the patients who achieved a minimum 3-point improvement in weekly average of Itch/Pruritus NRS from baseline at each study visit—non-responder imputation (ITT Population). However, data from the POEM and the Daily Sign and Symptom Severity Diary did not follow this pattern: there were no consistent differences observed between active treatment groups and vehicle groups, although the mean reductions (improvements) were consistently smaller for the vehicle BID group compared with the other treatment groups for the Daily Sign and Symptom Severity Diary. Also, for the assessment of sleep quality in the expanded POEM, the largest improvements at Week 12 were generally in the active treatment groups.

Subjects' impressions of the severity of their eczema symptoms from Baseline to Week 12, as well as investigators' assessments, corresponded with the clinical evaluations. Most subjects rated the change in the severity of their eczema symptoms, as well as the change in the severity of their itch, as "very improved" or "moderately improved" by the end of 12 weeks of treatment with Tapinarof cream.

Figure 5A:
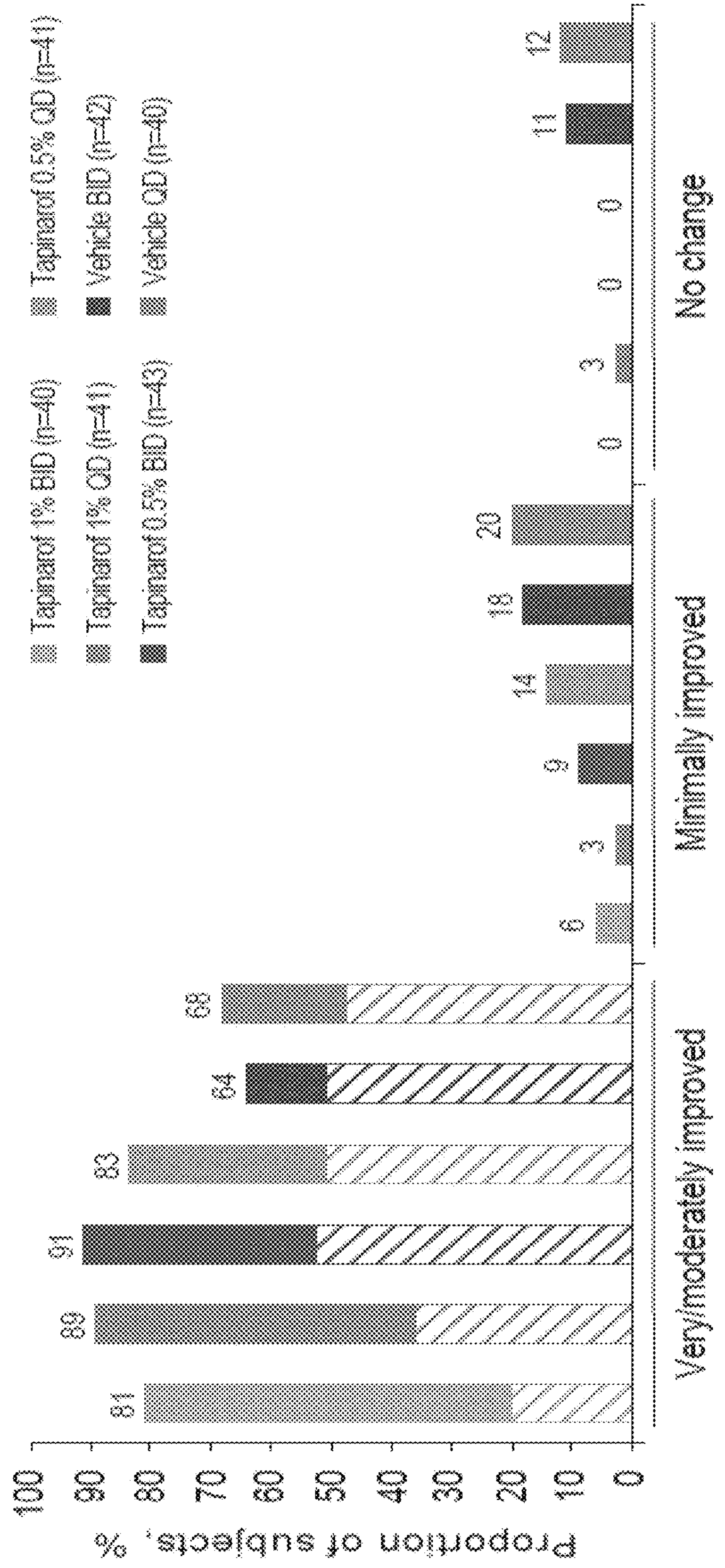
FIG. 5*a* presents subject impression of change in severity of AD symptoms at Week 12.
Figure 5B:
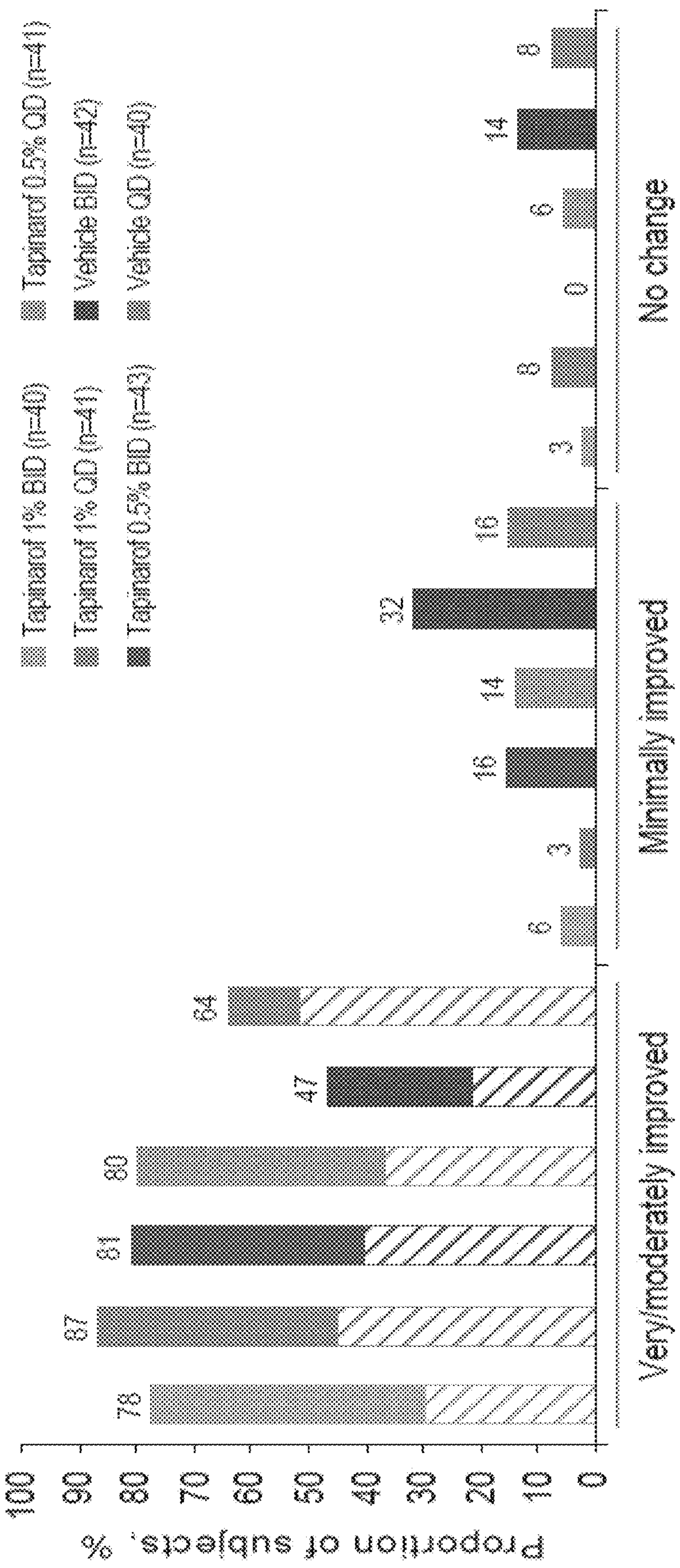
FIG. 5*b* presents subject impression of change in severity of pruritus symptoms at Week 12.

Subject impressions: At baseline, 86% of subjects rated their AD symptoms as moderate or severe across all treatment groups: 28-60% rated as moderate and 28-53% rated as severe. At Week 12, 64% (1% BID), 59% (1% QD), 47% (0.5% BID) and 40% (0.5% QD) of subjects in the tapinarof cream groups reported the severity of their AD symptoms as 'very improved' vs 21% (BID) and 28% (QD) in the vehicle groups (FIG. 5*a*). At Week 12, the majority of subjects treated with tapinarof cream (78-87% in the 1% groups and 80-81% in the 0.5% groups) rated the severity of their pruritus symptoms as 'very improved' or 'moderately improved' compared with the vehicle groups (47-64%) (FIG. 5*b*).

Expanded POEM: At Week 12, improvements were observed in all tapinarof cream and vehicle treated groups on all seven POEM items, except for the question relating to weeping or oozing for the 1% BID group. The three additional items in the expanded POEM showed overall sleep quality improved across all treatment groups, with the largest improvements in the tapinarof cream groups. For item 8 related to how many nights did subjects wake up at least once because of AD, the mean change reductions were largest in the tapinarof cream 0.5% groups (BID: −1.3 and QD: −1.2). For items 9 and 10 related to how difficult it was it for subjects to fall asleep or fall back asleep after waking because of AD, the number of subjects finding it difficult or very difficult to fall (back) asleep were lower in all treatment groups at Week 12 compared with baseline, except for one subject in the vehicle BID group for item 10.

Daily Sign and Symptom Severity Diary: The highest mean baseline scores were seen for dry or rough, red or discolored, and flaky skin. Overall there was an improvement in dry or rough, red or discolored, and flaky skin in all treatment groups as measured by the Daily Sign and Symptom Severity Diary scores, with the improvement being consistently smaller for the vehicle BID group vs the active tapinarof treatment groups for all items.

In the Japanese population, subject numbers were low, and there was a strong response in the vehicle BID group, so trends were not so clear.

Limited Tapinarof PK data are available in AD patients to date. Intensively sampled PK data are available in AD patients (n=6) from Study 201851; hence, the central tendency and variability in the PK of Tapinarof are not well defined. Given the PK data limitations, no definitive conclusions on the plasma PK of Tapinarof from Study 203121 can be made at the current time and therefore the data should be interpreted with caution. Therefore, comparison of PK across relevant subpopulations (adults, adolescents, Japanese) is not included.

Safety Discussion

The frequency of TEAEs was higher in the active treatment groups than in the vehicle groups (56% and 41%, respectively) and more TEAEs were considered treatment related in the active treatment groups (15%) than in the vehicle groups (10%). Most TEAEs were mild or moderate, with 2% and 4% (in active treatment and vehicle groups, respectively) being reported as severe. The frequency of TEAEs leading to permanent discontinuation of study treatment was higher in the pooled vehicle groups than the pooled active treatment groups (7% vs 4%), with the most common AE leading to discontinuation being worsening or flare of atopic dermatitis, which was reported in the 0.5% treatment groups and vehicle groups only; this may indicate a lack of efficacy compared with the 1% treatment groups. One subject in the 1% BID active treatment group experienced SAEs of anxiety and attention deficit/hyperactivity disorder that were considered unrelated to study treatment. No deaths and no other significant AEs were reported during the study.

The 1% QD treatment may have a slightly better safety profile than the 1% BID treatment, based on a lower frequency of TEAEs (54% versus 70%).

Overall, the most commonly reported TEAEs (>5% in any arm or in total, regardless of relationship to study treatment) were nasopharyngitis (8%), folliculitis (7%), atopic dermatitis (6%), upper respiratory tract infection (6%), headache (4%), acne (3%), and impetigo (2%). Comparing active with vehicle, the most commonly reported TEAEs (>5% in either pooled arm) were folliculitis (11% in the active groups versus 0% in the vehicle groups), nasopharyngitis (8% versus 9%), upper respiratory tract infection (7% versus 5%), headache (5% versus 2%), and atopic dermatitis (4% versus 11%). The most common treatment-related TEAEs (>5% in any arm) were folliculitis (5% and 0% in active treatment and vehicle groups, respectively) followed by application site pain (1% and 4%, respectively), and atopic dermatitis (1% and 2%, respectively). All other treatment-related TEAEs were reported in <1% of subjects overall: eczema impetiginous, herpes simplex, upper respiratory tract infection, atopic dermatitis, acne, contact dermatitis, dermal cyst, dry skin, hyperkeratosis follicularis et parafollicularis, pain of skin, rash, application site reaction, application site erythema, application site edema, application site pruritus, local reaction, headache, burning sensation, hypoesthesia, diarrhea, nausea, increased hepatic enzyme, and decreased monocyte count. No treatment-related TEAEs were assessed as serious.

The incidence and type of AEs in the adult and adolescent populations were consistent with that seen in the overall population: in all 3 populations the overall frequency of TEAEs was just over 50%, drug-related TEAEs were just under 15%, and TEAEs leading to permanent discontinuation of study treatment were 5%. In the adolescent population, compared with the adult population, there was a lower incidence of TEAEs of moderate intensity in the active treatment groups (14% in the adolescent population versus 25% in the adult population); the incidence in the vehicle groups was similar (13% and 16%, respectively).

The topical tolerability of Tapinarof cream, as judged by subjects as well as investigators, was very similar compared with vehicle and across concentration groups (0.5% and 1%) and with both frequencies of application (QD or BID). Tolerability improved from Week 1 to Week 12.

Elevations in liver chemistries (ALT/AST >2×ULN) were seen in 6 subjects, all in Tapinarof treatment groups. The elevations did not trigger protocol-mandated liver stopping criteria, the subjects all continued treatment, and all elevations resolved. No other clinically significant changes in laboratory values were reported.

Safety: Overall, 51% (127/247) of subjects had treatment-emergent AEs (TEAEs): 56% in the tapinarof cream groups and 41% in the vehicle groups (Table 4), and were mostly mild to moderate in severity. The most frequently reported TEAE was nasopharyngitis, which occurred in 20 (8%) subjects (8% in the tapinarof cream groups and 9% in the vehicle groups).

Mean percent change reduction in EASI scores from Baseline to each study visit was higher in all active treatment groups than in vehicle groups throughout the treatment period.

The frequency of application (QD or BID) had little effect on the mean percent change reduction in EASI scores, and indicates that the QD application has similar efficacy level to BID and would provide lower exposure than BID; therefore, it should be chosen for future Phase III studies. Also, the QD application offers an ease of use advantage that could lead to future subject treatment adherence.

Evaluation of mean change reduction in % BSA affected and TSS, and reduction in itch/pruritus symptoms were also supportive of the therapeutic effect of Tapinarof cream, as compared to vehicle.

Generally the adult population demonstrated a pattern consistent to that of the overall population with regard to the main efficacy endpoints. In the adolescent population, patterns differed somewhat, with stronger responses seen in the vehicle BID group across the efficacy endpoints, but the sample size was small.

Subject, as well as investigator, impressions of the severity of AD symptoms corresponded with clinical evaluations.

TABLE 4

Safety overview and most common TEAEs occurring in ≥5% of subjects in any group

| | Tapinarof 1% | | Tapinarof 0.5% | | Vehicle | |
|---|---|---|---|---|---|---|
| Preferred term, n (%) | BID (n = 40) | QD (n = 41) | BID (n = 43) | QD (n = 41) | BID (n = 42) | QD (n = 40) |
| Any TEAE | 28 (70) | 22 (54) | 20 (47) | 23 (56) | 19 (45) | 15 (38) |
| Treatment-related TEAEs | 6 (15) | 6 (15) | 8 (19) | 4 (10) | 6 (14) | 2 (5) |
| Serious TEAEs | 1 (3) | 0 | 0 | 0 | 0 | 0 |
| Discontinuous due to TEAEs | 1 (3) | 0 | 5 (12) | 1 (2) | 4 (10) | 2 (5) |
| TEAEs occurring in ≥5% of subjects in any group | | | | | | |
| Nasopharyngitis | 3 (8) | 5 (12) | 4 (9) | 1 (2) | 4 (10) | 3 (8) |
| Folliculitis | 4 (10) | 8 (20) | 3 (7) | 3 (7) | 0 | 0 |
| Dermatitis atopic | 2 (5) | 0 | 3 (7) | 1 (2) | 4 (10) | 5 (13) |
| URTI | 4 (10) | 2 (5) | 3 (7) | 2 (5) | 3 (7) | 1 (3) |
| Headache | 4 (10) | 1 (2) | 1 (2) | 3 (7) | 0 | 2 (5) |
| Acne | 2 (5) | 0 | 1 (2) | 3 (7) | 1 (2) | 0 |
| Impetigo | 1 (3) | 0 | 0 | 0 | 0 | 3 (8) |

Overall, Tapinarof cream showed an acceptable safety and tolerability profile.

Conclusions

The proportion of subjects who achieved an IGA score of clear or almost clear (0 or 1) at Week 12 and a minimum 2-grade improvement in IGA score from Baseline to Week 12 was higher in 3 of the active treatment groups (1% BID or 1% QD, or 0.5% BID) than in vehicle groups.

IGA treatment success in active treatment groups were observed from Week 1, separated from vehicle at Week 4, peaked at Week 8 or Week 12 and started to decrease after the end of treatment.

The frequency of application (BID or QD) had no clear effect on the IGA treatment success over time.

The proportion of subjects with EASI75 from Baseline to Week 12 was clearly higher in all active treatment groups than in vehicle groups.

In general, in the active groups, EASI75 appeared from Week 2, peaked at Week 12 and was durable, lasting up to 4 weeks after the end of treatment, particularly in the 0.5% BID group.

Most subjects rated the change in the severity of their eczema symptoms as "very improved" or "moderately improved" by the end of treatment with Tapinarof cream (Week 12).

Given the limited available data, Tapinarof population PK was not characterized.

Tapinarof cream showed an acceptable safety profile. There were no treatment-related serious TEAEs reported. The most frequent treatment-related TEAEs (>5% in any arm) were folliculitis, followed by application site pain, and atopic dermatitis.

The incidence and type of AEs in the adult and adolescent populations were generally consistent with that seen in the overall population; there was a lower incidence of moderate AEs in the adolescent population than in the overall and adult populations.

Elevations in liver enzymes were seen in 6 subjects in the active treatment groups, however the elevations did not trigger protocol-mandated liver stopping criteria, the subjects continued treatment, and all elevations resolved. No other clinically significant changes in laboratory values were reported.

The topical tolerability of Tapinarof cream, as judged by subjects as well as investigators, was similar across concentration groups (0.5% and 1%) and with both frequencies of application (QD or BID). Tolerability improved from Week 1 to Week 12.

Based on the lower incidence of TEAEs, the 1% QD treatment may have a slightly better safety profile than the 1% BID treatment.

Additional Analysis.

Primary endpoint—efficacy based on percentage of patients who achieved minimum two-point improvement in IGA score and assessment of "clear" or "almost clear" skin, referred to as "treatment success."

Secondary endpoint—EASI score, BSAA score, itch improvement, change in total severity score, subject impressions of symptom severity and safety and tolerability.

Using a post-hoc analysis to account for missing data due to the high rate of dropout in the vehicle group, at week 12, 53% of patients treated with 1% BID (statistically significant compared to vehicle) and 46% treated with 1% QD met treatment success, compared with 24% and 28% for vehicle BID and QD, respectively. At week 12, 37% of patients treated with 0.5% BID and 34% treated with 0.5% QD met treatment success.

At week 12, 60% and 510% of patients achieved a 75% improvement in EASI score in 1% BID and 1% QD groups, respectively (statistically significant compared to vehicle). Statistical significance was achieved, and the endpoint was met, for all tapinarof groups compared to vehicle, with the exception of 0.5% QD.

At week 12, subjects treated with both 0.5% and 1% concentrations showed greater improvements in mean change in percentage BSA affected from baseline (as demonstrated by an absolute change in percent BSA affected of 11.2 for 1% BID and 11.6 for 1% QD, respectively, compared with 6.0 for BID vehicle and 5.4 for QD vehicle). While statistical significance was not evaluated for this endpoint, the endpoint was determined to be met.

At week 12, subjects treated with both 0.5% and 1% concentrations showed greater improvements in mean change in total severity score (reduction of 5.8 for 1% BID and 5.5 for 1% QD, compared with 4.6 for BID vehicle and 5.2 for QD vehicle). Statistical significance was not evaluated for this endpoint and we could not determine that the endpoint was met.

At week 12, subjects treated with both 0.5% and 1% concentrations showed greater improvements in subject impressions of symptom severity (64% for 1% BID and 59% for 1% QD categorized symptoms as very improved, compared with 21% for BID vehicle and 28% for QD vehicle). While statistical significance was not evaluated for this endpoint, the endpoint was determined to be met. In particular, at week 12, based on subject impressions of change in severity of pruritus, most patients treated with tapinarof 1% (78% BID and 86% QD) rated their itch to be "moderately improved" to "very improved" compared to patients treated with vehicle (46% BID and 64% QD). While statistical significance was not evaluated for this endpoint, the endpoint was determined to be met.

At week 12, 30% and 33% of patients treated with tapinarof 1% BID and 0.5% BID, respectively, achieved a minimum three-point improvement in itch numerical rating score, or NRS, compared to 5% treated with vehicle BID. Similarly, at week 12, 32% and 29% of patients treated with tapinarof 1% QD and 0.5% QD, respectively, achieved a minimum three-point improvement in itch NRS, compared to 15% treated with vehicle QD. While statistical significance was not evaluated for this endpoint, the endpoint was determined to be met.

Generally well tolerated at 0.5% and 1% concentrations, with majority of AEs and treatment emergent AEs reported as mild or moderate. 133 subjects experienced at least one AE (97 in treatment groups). 127 subjects experienced at least one treatment-emergent adverse event, or TEAE (93 in treatment groups). A TEAE is defined as an AE which occurred on or after the start date of study treatment and on or before the last visit.

32 subjects had TEAEs that were considered related to treatment (24 subjects in the treatment groups). The most common treatment-related TEAEs were folliculitis, application-site pain, and atopic dermatitis upper respiratory tract infection and headache. One subject reported a serious TEAE, which was not considered related to treatment. 13 subjects discontinued prior to end of treatment period due to TEAEs.

Example 2—Results of Phase II Clinical Study in Psoriasis

The present study, which included 227 subjects, was conducted to evaluate the efficacy and safety of a range of concentrations of Tapinarof cream for the topical treatment of psoriasis. Results of this study will be used to select the most appropriate concentration and application frequency of Tapinarof cream to evaluate in confirmatory Phase III clinical studies.

The study objectives and the associated endpoints were as described in Table 5.

TABLE 5

Study Objectives and Associated Endpoints

| Objectives | Endpoints |
|---|---|
| Primary | |
| To estimate the relationship between Tapinarof cream concentrations (0.5% and 1%) and application frequency with efficacy response, based upon clinical evaluations in subjects with plaque psoriasis | Proportion of subjects who had a PGA score of clear or almost clear (0 or 1) at Week 12 and a minimum 2-grade improvement in PGA score from Baseline to Week 12 |
| Secondary | |
| To estimate the efficacy of Tapinarof cream | Proportion of subjects with ≥75% improvement in PASI from Baseline to each study visit<br>Proportion of subjects with a minimum 2-grade |

TABLE 5-continued

| Study Objectives and Associated Endpoints | |
|---|---|
| Objectives | Endpoints |
| | improvement in PGA score from Baseline to each study visit<br>Proportion of subjects with a PGA score of 0 or 1 at each study visit<br>Mean change in % BSA affected from Baseline to each study visit<br>Mean change in PASI score from Baseline to each study visit<br>PGA scores at each study visit<br>Mean change in PGA score from Baseline to each study visit<br>Mean change in individual target lesion grading scores (erythema, scaling, and induration) from Baseline to each study visit<br>Mean change in itch/pruritus NRS from Baseline to each study visit<br>Proportion of subjects who achieved a PGA score of 0 or 1 and a minimum 2-grade improvement from Baseline to each study visit |
| To describe the safety and tolerability of Tapinarof cream | Incidence, frequency, and nature of AEs and SAEs<br>Local tolerability scores over time<br>Change over time in clinical laboratory tests and frequency of clinically-significant abnormal test results<br>Change over time in vital signs and frequency of clinically-significant abnormal results<br>Incidence and nature of abnormal ECGs |
| Other | |
| To describe the effect of Tapinarof cream on subject-reported outcomes | Change over time in daily PSD<br>Subject impression of change in psoriasis symptom severity from Baseline to Week 12 |
| To characterize the population pharmacokinetics (PK) of Tapinarof after topical application of Tapinarof cream | Population estimates of PK parameters, as data permit |
| To explore the relationship between topical application (as cream concentration and % BSA treated), efficacy, and/or safety, and systemic exposure of Tapinarof, as data permit | Relationship between cream concentration and/or % BSA treated and changes in systemic exposure as data permit<br>Relationship between systemic exposure and changes in efficacy (e.g., PGA score) and/or safety endpoints, as appropriate |
| To estimate the duration of response of Tapinarof cream | Proportions of subjects who achieved a PGA score of 0 or 1 and a minimum 2-grade improvement from Baseline at Week 12 and maintained the improvement at 2 and 4 weeks post-treatment<br>Proportions of subjects who achieved improvement with respect to individual secondary efficacy endpoints at Week 12 and maintained the improvement at 2 and BSA, Body Surface Area; ECG, electrocardiogram; NRS, numeric rating scale; PASI, Psoriasis Area and Severity Index; PGA, Physician Global Assessment; PSD, Psoriasis Symptom Diary; SAE, serious adverse event.<br>4 weeks post-treatment, as appropriate |

Study Design

This was a multicenter (United States, Canada, and Japan), randomized, double-blind (Sponsor-unblind), vehicle-controlled, 6-arm, parallel-group, dose-finding study in adult subjects with psoriasis. Certain study personnel at each site were unblinded to dose-frequency.

The study consisted of 3 periods: up to 4 weeks Screening, 12 weeks double-blind treatment, and 4 weeks post-treatment follow-up. Study visits occurred at Screening; Baseline; weeks 1, 2, 4, 8, and 12 during the treatment period; and 2 and 4 weeks after the last application of study treatment (i.e., at weeks 14 and 16). Additional visits could occur, as needed, for early withdrawals or to follow-up on any skin reactions or ongoing AEs. A subject's total duration of study participation was approximately 16 to 20 weeks.

Two concentrations of Tapinarof cream (0.5% and 1%) and a vehicle control were evaluated following application to all psoriasis lesions (except on the scalp) once (QD) or twice daily (BID) for 12 weeks. There were no planned dose adjustments during the study.

It was expected that approximately 270 adult subjects would be screened to achieve 228 randomized subjects (1:1:1:1:1:1; N=38 for each of the 6 treatment groups; vehicle once daily: vehicle twice daily: 0.5% once daily: 0.5% twice daily: 1% once daily: 1% twice daily) and approximately 204 evaluable subjects overall. Approximately 30 subjects were to be randomized in Japan to achieve at least 24 evaluable Japanese subjects.

The intent-to-treat (ITT) Population included all randomized subjects. Subjects that prematurely discontinued from the study were not replaced.

Efficacy was assessed by using a 5-point static Physician Global Assessment (PGA) (0-4 scale), the Psoriasis Area and Severity Index (PASI), % BSA involvement, target lesion assessments (erythema, scaling, and plaque thickness), and subject-reported itch/pruritus severity using a numeric rating scale (NRS) (from the Psoriasis Symptom Diary [PSD]). Additional subject-reported outcomes included the daily PSD (which also contained severity and bother items for 3 additional symptoms). Investigator global impression of change item (assessing change in severity of psoriasis symptoms) and 2 subject global impressions of change items (assessing change in severity of psoriasis symptoms and change in severity of itch/pruritus) were also assessed.

Safety was assessed by the monitoring and recording of all AEs and serious adverse events (SAEs); evaluation of local (application site) tolerability; monitoring of hematology (including peripheral blood Immunophenotyping and Immunoglobulins), clinical chemistry, and vital signs; and the performance of ECGs and physical examinations.

An Independent Data Monitoring Committee (IDMC) met to monitor safety of the Tapinarof cream.

An interim analysis was carried out (database lock: 6 Jul. 2016) to identify the appropriate drug concentration and topical application frequency of Tapinarof for use in Phase III clinical studies. The interim analysis had originally been planned to be conducted when 100 subjects had completed 8 weeks of treatment. However, due to GCP noncompliance being discovered at 1 site (see Section 5.2.1), the number of subjects required for the interim analysis was increased to 130 in order to have approximately 100 subjects in the modified ITT (mITT) interim Population.

Discussion of Study Design

The randomized, double-blind (Sponsor-unblind), vehicle-controlled study design was selected to minimize the potential for subjective bias related to possible identification of which subjects were receiving active treatment and to minimize selection and allocation bias by balancing potential prognostic factors. The study was conducted at multiple study centers to enhance the possibility of inclusion of a wider range of population groups and to subsequently increase generalizability of the results.

Clinical studies in skin conditions have historically shown a notable vehicle (as well as placebo) response rate, which could be attributable to the effects of skin moisturization or to the increased emphasis on proper skin care while participating in a clinical study. A vehicle control group was included in this study to provide a control for comparison and to ensure study assay sensitivity for characterization of the safety and efficacy profile of Tapinarof cream.

The predicted maximum systemic exposure to Tapinarof in this study was expected to be lower than the no observed adverse effects level (NOAEL) identified in nonclinical toxicology studies. Exposure predicted based on in vitro flux data and topical minipig relative bioavailability showed a lesser systemic exposure for 1% cream formulation F versus Formulations C or E. This provided a safety margin of 4- to 8-fold for predicted area under the concentration-time curve $(AUC)_{(0-24)}$ and 4- to 6-fold for predicted maximum observed concentration (Cmax) for 1% cream (formulation F) applied BID when compared with the NOAEL obtained from the rat subcutaneous 3 mg/kg/day, 13-week toxicology study (99 ng·h/mL for AUC(0-24) and 31.6 ng/mL for Cmax).

The treatment duration was 12 weeks. Previous studies of Tapinarof cream (using formulation C) showed some efficacy within the first 14 days of treatment and increasing efficacy over 12 weeks of treatment. The 12-week treatment endpoint in this study was expected to be an adequate duration of treatment to measure response and is in line with the duration of treatment in other studies of topical treatments for psoriasis.

Inclusion Criteria: A subject was eligible for inclusion in this study only if all of the following criteria applied: 1. Male or female aged 18 years to 65 years, inclusive, at the time of informed consent; 2. Clinical diagnosis of chronic stable plaque psoriasis for ≥6 months; 3. Body surface area involvement ≥1% and ≥15%, excluding scalp, at Screening and Baseline; 4. A PGA of psoriasis score ≥2 at Baseline; 5. One target plaque located on the trunk or proximal parts of extremities (excluding knees, elbows, and intertriginous areas) that was at least 3 cm×3 cm in size at Screening and Baseline with a severity representative of the subject's overall disease; 6. A female subject was eligible to participate if she was not pregnant (as confirmed by a negative urine human chorionic gonadotrophin [hCG] test), not lactating, and when at least one of the following conditions applied: a. Non-reproductive potential defined as: Pre-menopausal females with 1 of the following: documented tubal ligation, documented hysteroscopic tubal occlusion procedure with follow-up confirmation of bilateral tubal occlusion, hysterectomy, documented bilateral oophorectomy; postmenopausal was defined as 12 months of spontaneous amenorrhea (in questionable cases a blood sample with simultaneous follicle stimulating hormone [FSH] and estradiol levels consistent with menopause [refer to laboratory reference ranges for confirmatory levels]). Females on hormone replacement therapy (HRT) and whose menopausal status was in doubt were required to use 1 of the highly effective contraception methods if they wished to continue their HRT during the study. Otherwise, they had to discontinue HRT to allow confirmation of postmenopausal status prior to study enrolment. b. Reproductive potential and agreed to follow 1 of the options listed in the Modified List of Highly Effective Methods for Avoiding Pregnancy in Females of Reproductive Potential (FRP) from 30 days prior to the first dose of study medication and until (at least 5 terminal half-lives OR until any continuing pharmacologic effect had ended, whichever was longer) after the last dose of study medication and completion of the follow-up visit. The investigator was responsible for ensuring that subjects understood how to properly use these methods of contraception.

Exclusion Criteria: A subject was not eligible for inclusion in this study if any of the following criteria applied: 1. Any sign of infection of any of the psoriatic lesions; 2. A history or ongoing serious illness or medical, physical, or psychiatric condition(s) that, in the investigator's opinion, could have interfered with the subject's completion of the study; 3. Known hypersensitivity to the study treatment excipients (for a detailed description of the ingredients of the study treatment, refer to, or a history of drug or other allergy that, in the opinion of the investigator, contraindicated participation; 4. Current or chronic history of liver disease, known hepatic or biliary abnormalities (with the exception of Gilbert's syndrome or asymptomatic gallstones), presence of hepatitis B surface antigen (HBsAg), or positive hepatitis C antibody test result within 3 months of Screening; 5. Liver function tests: alanine aminotransferase (ALT) ≥2× upper limit of normal (ULN); alkaline phosphatase and bilirubin <1.5×ULN (isolated bilirubin >1.5×ULN was acceptable if bilirubin was fractionated and direct bilirubin <35%); 6. QT interval corrected for heart rate (QTc) ≥450 msec or QTc ≥480 msec for subjects with bundle branch block. The QTc is the QT interval corrected for heart rate, with machine overread. The QTc was to be based on a single ECG obtained over a brief recording period. If QTc was outside of the threshold value, triplicate ECGs could be performed with the QTc values averaged (see Protocol Section 7.4.5 for information on QTc correction formula.) 7. Ultraviolet (UV) light therapy or prolonged exposure to natural or artificial sources of UV radiation (e.g., sunlight or tanning booth) within 4 weeks prior to the Baseline visit and/or intention to have such exposure during the study, which was thought by the investigator to potentially impact the subject's psoriasis. 8. Used any of the following treatments within the indicated washout period before the Baseline visit: a. 12 weeks or 5 half-lives (whichever was longer)—biologic agents (e.g., 24 weeks for alefacept, 12 weeks for etanercept, 15 weeks for ustekinumab); b. 12 weeks—oral retinoids (e.g., acitretin or isotretinoin); c. 8 weeks—cyclosporin, interferon, methotrexate, other systemic immunosuppressive or immunomodulating agents, or psoralen plus ultraviolet A (UVA) light treatment; d. 4 weeks—systemic corticosteroids or adrenocorticotropic hormone analogs; e. 2 weeks—immunizations; drugs known to possibly worsen psoriasis, such as R blockers (e.g., propranolol), lithium, iodides, angiotensin-converting enzyme inhibitors, and indomethacin, unless on a stable dose for >12 weeks; f. 2 weeks—topical treatments: corticosteroids, immunomodulators, anthralin (dithranol), Vitamin D derivatives, retinoids, or coal tar (used on the body); 9. Participated in a clinical study and received an investigational product within the following time period prior to the Baseline visit: 4 weeks, 5 half-lives, or twice the duration of the biological effect of the investigational product (whichever was longer); 10. History of alcohol or other substance abuse within the last 2 years; 11. Participated in a previous study using Tapinarof (GSK2894512 or WBI-1001).

Investigational Product and Reference Therapy: The term 'study treatment' is used throughout this document to describe the product (i.e., Tapinarof or vehicle) received by subject as per the protocol design, as shown in Table 6.

TABLE 6

Investigational Product and Reference Therapy

| Drug | Dose/Form/Route | Frequency/Duration |
|---|---|---|
| Tapinarof | 1% (10 mg/g), cream, topically | BID, 12 weeks |
| Tapinarof | 1% (10 mg/g), cream, topically | QD, 12 weeks |
| Tapinarof | 0.5% (5 mg/g), cream, topically | BID, 12 weeks |
| Tapinarof | 0.5% (5 mg/g), cream, topically | QD, 12 weeks |
| Vehicle | 0%, cream, topically | BID, 12 weeks |
| Vehicle | 0%, cream, topically | QD, 12 weeks |

The list of excipients include are propylene glycol, diethylene glycol monoethyl ether, polysorbate 80, medium chain triglycerides, emulsifying wax non-ionic, polyoxyl stearyl ether 2, polyoxyl stearyl ether 20, benzoic acid, butylated hydroxytoluene, purified water, sodium citrate, citric acid monohydrate, and edetate disodium.

Primary Endpoint

The primary endpoint was the proportion of subjects who had a PGA score of clear or almost clear (0 or 1) at Week 12 and a minimum 2-grade improvement in PGA score from Baseline to Week 12.

Physician Global Assessment: The PGA is a clinical tool for assessing the current state/severity of a subject's psoriasis. It is a static 5-point morphological assessment of overall disease severity, as determined by the investigator, using the clinical characteristics of erythema, plaque thickness, and scaling as guidelines. At each specified time point, the PGA is made without reference to previous scores. Variations of the PGA are frequently used in clinical studies because it is a simple assessment that is more similar to the assessments actually used in clinical practice. Scoring system ranges from 0 (=Clear) to 4 (=Severe).

Secondary Endpoints

The secondary endpoints were the following: 1) Proportion of subjects with ≥75% improvement in PASI from Baseline to each study visit; 2) Proportion of subjects with a minimum 2-grade improvement in PGA score from Baseline to each study visit; 3) Proportion of subjects with a PGA score of 0 or 1 at each study visit; 4) Mean change in % BSA affected from Baseline to each study visit; 5) Mean change in PASI score from Baseline to each study visit; 6) PGA scores at each study visit; 7) Mean change in PGA score from Baseline to each study visit; 8) Mean change in individual target lesion grading scores (erythema, scaling, and induration) from Baseline to each study visit; 9) Mean change in itch/pruritus NRS from Baseline to each study visit; 10) Proportion of subjects who achieve a PGA score of 0 or 1 and a minimum 2-grade improvement from Baseline to each study visit.

Psoriasis Area and Severity Index: The PASI scoring system is a widely-used standard clinical tool for assessing the severity of psoriasis that takes into account the overall severity of erythema (redness), thickness (induration), and scale, as well as the extent of BSA affected with psoriasis. The 3 clinical signs are each graded on a 5 point scale (0 to 4) and the % BSA affected is scored on a 7-point scale (0 to 6) for each of the 4 specified body regions (head, upper extremities, trunk, and lower extremities). The individual scores are multiplied by a weighted factor for each body region; the sum of these scores gives the overall PASI score. Higher scores indicate more severe disease. PASI is a static assessment made without reference to previous scores.

Body Surface Area: The extent of BSA affected by psoriasis is a general indicator of disease severity and was measured throughout the study. The extent of BSA to which study treatment was applied was also recorded. For the purpose of approximate clinical estimation, the total palmar surface of the palm plus 5 digits was assumed to be approximately equivalent to 1% BSA.

Target Lesion Grading: A single target lesion was selected at Baseline to assess efficacy in treating a discrete area rather than an overall average of all areas. For that lesion, the severity of erythema, scaling, and plaque thickness was assessed by the investigator on a 5-point scale ranging from "0=none" to "4=severe".

Itch/Pruritus Severity: Subject-reported itch severity was obtained from the itch NRS item from the PSD.

Investigator Impression of Change Item: This was a single item that asked the investigator to rate the change from Baseline in the subject's overall psoriasis symptoms. Response options ranged from "1=very improved" to "7=very worse". Results will also be used as a clinical anchor in analyses of the minimally important differences in itch and daily symptom severity.

Other Efficacy Endpoints: Other efficacy endpoints were as follows: Relationship between cream concentration and/or % BSA treated and changes in systemic exposure as data permit. Proportions of subjects who achieved a PGA score of 0 or 1 and a minimum 2 grade improvement from Baseline at Week 12 and maintained the improvement at 2 and 4 weeks post-treatment. Proportions of subjects who achieved improvement with respect to individual secondary efficacy endpoints at Week 12 and maintained the improvement at 2 and 4 weeks post-treatment, as appropriate. Endpoints related to systemic exposure: Relationship between systemic exposure and changes in efficacy (e.g., PGA score) and/or safety endpoints, as appropriate.

Pharmacokinetics: Sparse PK sampling throughout the duration of the study was intended to be used to develop a population PK model and to estimate population PK parameters (i.e., apparent clearance [CL/F], apparent volume of distribution [V/F]) of systemic exposure, according to the Time and Events Table. Plasma analysis was performed under the management of Bioanalysis, Immunogenicity & Biomarkers, IVIVT, PTS, GSK.

Health Outcomes

In order to evaluate symptoms and symptom impact, subjects completed the PSD daily as well as an overall severity of psoriasis symptoms item and global impression of change items (assessing change in severity of psoriasis symptoms and itch/pruritus). Each investigator also completed a global impression of change item (assessing change in severity of psoriasis symptoms) for each subject.

Psoriasis Symptom Diary (PSD): The PSD was developed to assess daily self-reports of psoriasis symptoms and the functional impact related to the underlying pathophysiology of the disease. Each item was rated using an 11-point NRS. Questions asked about how severe and how bothersome various signs and symptoms were to the subject. The recall period was the last 24 hours. In addition to the 16 questions included in the already established version of the PSD, 6 questions were added to assess the severity and bother of skin flaking, dryness, and bleeding and were similar in wording to the items in the established version of the PSD.

Subject Impression of Severity and Change Items: At Baseline, subjects were asked to rate the overall severity of their psoriasis symptoms on a scale ranging from "1=mild" to "4=very severe." The global impression of change items asked subjects to rate their change from Baseline to Week 12 in overall severity of psoriasis symptoms and in overall severity of itch. Response options ranged from "1=very improved" to "7=very worse."

Primary Efficacy Endpoint

The primary efficacy analyses were planned to be conducted on the mITT and PP Population, but since more than 95% of the PP Population was in the mITT Population, no analyses were conducted on PP Population.

The study day relative to Day 1 was used as a covariate in the model.

The primary analysis was a repeated measures factorial logistic regression for the primary endpoint (proportion of subjects who had a PGA score of 0 or 1 at Week 12 and a minimum 2-grade improvement in PGA score from Baseline to Week 12) with covariates for dose (0% for vehicle, 0.5% and 1%), frequency of administration (QD or BID), and study day as well as a dose by frequency interaction term. The response at each visit was modeled as repeated measures via inclusion of a random subject effect. Estimated population mean dose/frequency-response curves along with their corresponding 95% confidence bands were provided for all dose levels and frequencies by time points of interest. Estimated mean difference in response rate with 95% confidence interval between GSK2894512 and vehicle cream for BID and QD were provided by time points of interest.

Supportive statistical analyses of the primary endpoint based on Japanese subjects in the mITT Population was conducted for 2 frequencies (QD or BID) separately using simple logistic regression model with covariate for dose (0% for vehicle, 0.5% and 1%). The same analysis was done for the overall mITT Population to compare the results of Japanese Population and Overall Population.

Summary statistics of the number of subjects providing data at the relevant time point, frequency counts and percentages, and 95% exact confidence interval were provided for the PGA response rate for each treatment group at each study visit. Mean and 95% confidence interval were provided for the difference of (each BID dose—vehicle BID) and the difference of (each QD dose—vehicle QD) in PGA response rate at each visit.

Secondary Efficacy Endpoints

The secondary efficacy analyses were based on the mITT Population, unless otherwise specified. The proportion of subjects who achieved a PGA score of 0 or 1 and a minimum 2-grade improvement from Baseline to each study visit, the proportion of subjects with ≥75% improvement in PASI from Baseline to each study visit and the proportion of subjects with ≥50% improvement in PASI from Baseline to each study visit were analyzed based on the mITT Population.

For continuous endpoints, a repeated measures Emax model with Integrated two-component prediction (ITP) time component was fitted to the data. All dichotomous secondary endpoints were modeled in the same logistic regression model described in the primary statistical analysis. For continuous data, summary statistics of the mean, SD, median, minimum, maximum and number of observations were provided for each treatment group at each study visit. For data of proportions, summary statistics of the number of subjects providing data at the relevant time point, frequency counts and percentages, and 95% exact confidence interval were provided for each treatment group at each study visit. Mean and 95% confidence intervals were provided for the difference of (each BID dose—vehicle BID) and the difference of (each QD dose—vehicle QD) in the proportion at each visit.

Demographics and Baseline Characteristics

Overall, mean demographic and Baseline characteristics were comparable across treatment groups. Most subjects (80%) had a Baseline PGA category of "moderate" and a Baseline mean PASI score of 8.81 (standard deviation [SD] 4.472). Most Japanese subjects (75%) also had a Baseline PGA category of "moderate" and had a higher Baseline mean PASI score (12.44 [SD 6.469]) than the Overall Population.

The vehicle QD group included a slightly smaller number of women than the rest of the groups ("gender" is not known to affect psoriasis).

The total number of subjects that completed the itch/pruritus NRS item at Baseline was slightly smaller than the number of subjects for which there were other Baseline data available (190 vs 196, respectively).

Baseline PASI scores were higher in the 1% BID group in the Overall and Japanese Populations.

Baseline duration of psoriasis in the Japanese Population was slightly shorter in the 1% (QD and BID) groups than the rest of the groups.

A total of 227 subjects (of the 290 subjects originally screened) were randomized into the study at 17 sites in the United States, 12 sites in Canada, and 11 sites in Japan (intent-to-treat [ITT] analysis population). Of those randomized, 175 subjects (77%) completed the study including the Week 16 follow-up visit. Overall, mean demographic and baseline characteristics were comparable across treatment groups (Table 7). Most subjects (80%) had a baseline PGA category of 3 (moderate) and a baseline mean Psoriasis Area and Severity Index (PASI) score of 8.8 (SD 4.5). Primary endpoint: PGA response rates (defined as PGA score 0 or 1 and ≥2-grade improvement) at Week 12 were higher in the tapinarof cream groups than the vehicle groups (65% [1% BID]; 56% [1% QD]; 46% [0.5% BID]; 36% [0.5% QD]; 11% [vehicle BID], and 5% [vehicle QD]) and were maintained for 4 weeks after the end of study treatment.

TABLE 7

| Baseline subject demographics and characteristics | | | | | | |
|---|---|---|---|---|---|---|
| | Tapinarof 1% | | Tapinarof 0.5% | | Vehicle | |
| | BID (n = 38) | QD (n = 38) | BID (n = 38) | QD (n = 38) | BID (n = 37) | QD (n = 38) |
| Mean age, years (SD) | 45.9 (11.9) | 48.5 (10.6) | 49.6 (10.9) | 48.7 (9.7) | 46.7 (12.6) | 46.4 (10.2) |
| Male sex, n (%) | 26 (68) | 26 (68) | 24 (63) | 25 (66) | 23 (62) | 29 (76) |
| Mean weight, kg (SD) | 85.6 (22.5) | 86.7 (22.6) | 88.6 (27.4) | 89.3 (23.1) | 87.8 (28.3) | 91.6 (21.6) |
| PGA score, mean (SD) | 2.9 (0.4) | 2.7 (0.5) | 3.0 (0.5) | 2.9 (0.4) | 3.0 (0.3) | 2.8 (0.4) |
| PASI score, mean (SD) | 10.6 (5.0) | 8.5 (3.6) | 8.2 (4.5) | 7.9 (4.8) | 9.0 (4.3) | 8.7 (4.4) |
| BSA affected, % (SD) | 8.2 (4.5) | 6.5 (3.3) | 7.2 (4.5) | 6.1 (4.3) | 6.6 (3.6) | 7.0 (4.6) |
| Pruritus score, mean (SD)* | 5.6 (2.6) | 4.4 (2.9) | 6.2 (2.2) | 4.5 (2.6) | 5.5 (2.8) | 4.9 (2.4) |

*Mean scores based on a scale of 0 'absent' to 10 'worst imaginable'. Demographics provided for the safety analysis population (n = 227) and characteristics provided for the mITT analysis population (n = 196). The mITT analysis population included subjects in the ITT population minus the subjects from one site due to concerns regarding data accuracy.

BID, twice daily; BSA, body surface area; ITT, intent-to-treat; mITT, modified intent-to-treat; PASI, Psoriasis Area and Severity Index; PGA, Physician Global Assessment; QD, once daily; SD, standard deviation.

Efficacy Results

Efficacy results are reported using the mITT Population. No analysis based on the PP Population was conducted since more than 95% (188/196=96%) of the PP Population was in the mITT Population. Unless mentioned otherwise, results reported in this section are those of the Overall Population and refer to observed cases (OC) imputation method.

Interim Analysis: A "go" decision was reached based on a clinically meaningful efficacy profile and a well-tolerated safety profile (the analysis included 100 subjects): Response rates of 42%, 32%, 36%, 46% at Week 8 for the primary endpoint with GSK2894512 cream concentrations 1% BID, 1% QD, 0.5% BID, 0.5% QD, respectively, and 0% for vehicle BID and vehicle QD. Efficacy responses were better at each study visit in the 1% concentration based on PASI. Mild to moderate application site reactions (folliculitis and contact dermatitis) as the main AEs.

Physician Global Assessment (PGA): The primary objective of this study was to estimate the relationship between Tapinarof cream concentrations (0.5% and 1%) and application frequency (QD or BID) with efficacy response based upon clinical evaluation in subjects with plaque psoriasis. The primary endpoint was the proportion of subjects who had a PGA score of clear or almost clear (0 or 1) at Week 12 and a minimum 2-grade improvement in PGA score from Baseline to Week 12.

The planned repeated measures factorial logistic regression model with ITP did not fit the data well. Therefore, summary statistics of the number of subjects providing data at the relevant time point, frequency counts and percentages, and 95% exact confidence interval were provided for the PGA response rate for each treatment group at each study visit. Mean and 95% confidence interval were provided for the difference of (each BID dose—vehicle BID) and the difference of (each QD dose—vehicle QD) in PGA response rate at each visit.

Figure 6:
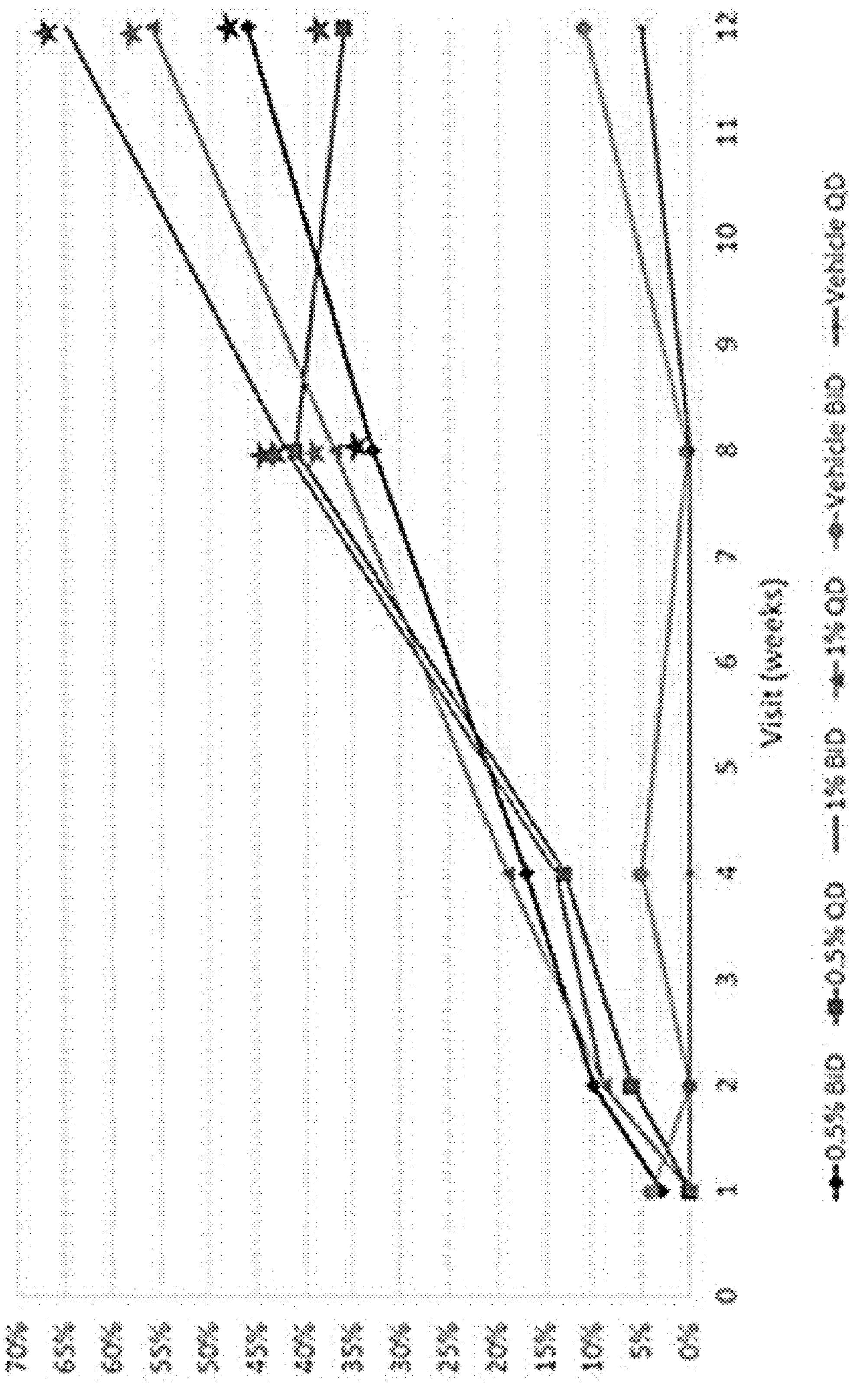
FIG. 6 depicts the proportion of patients who achieved a PGA score of 0 or 1 and a minimum 2-grade improvement from baseline (mITT Population) (OC). All tapinarof groups showed a clear separation from vehicle reaching statistical significance after 8 weeks of treatment, with 1% concentration showing highest response rates.

The primary endpoint analysis showed a higher proportion of subjects in the active treatment groups than in the vehicle groups at Week 12. The 1% concentration treatment groups showed a higher rate of response than the 0.5% concentration groups. PGA response rates (treatment success defined by PGA score 0 or 1 and a minimum 2-grade improvement) at Week 12 were statistically significantly higher (at 0.05 significance level) in the tapinarof groups than the vehicle groups (65% [1% BID]; 56% [1% QD]; 46% [0.5% BID]; 36% [0.5% QD]; 11% [vehicle BID], and 5% [vehicle QD](FIG. 6). Differences between active and vehicle were (95% CI): 54.7% (25.9%, 76.6%) [1% BID-vehicle BID], 51.0% (22.2%, 73.2%) [1% QD-vehicle QD], 35.6% (6.3%, 60.5%) [0.5% BID-vehicle BID], 30.7% (1.6%, 55.9%) [0.5% QD-vehicle QD]). PGA treatment success was statistically significantly greater (at 0.05 significance level) in the tapinarof treatment groups than in the vehicle groups at Week 12 and was maintained for 4 weeks after the end of study treatment—Week 16 except for the 0.5% BID group (58% [1% BID]; 54% [1% QD]; 35% [0.5% BID]; 36% [0.5% QD]; 5% [vehicle BID], and 0 [vehicle QD] (FIG. 6).

PGA secondary endpoint analyses revealed: An increasing proportion of subjects who had a minimum 2-grade improvement in PGA score from Baseline to each study visit in the active treatment groups compared with the vehicle groups. The 1% concentration treatment groups showed a higher rate of responders than the 0.5% concentration groups at Week 12.

An increased proportion of subjects who had a PGA score of 0 or 1 and a minimum 2-grade improvement in PGA scores from Baseline to Week 12 and maintained the improvement at 2 and 4 weeks post-treatment in the active treatment groups compared with the vehicle groups. The 1% concentration treatment groups showed a higher rate of responders than the 0.5% concentration groups. Specifically, 67% (10 of 15) of subjects in the 1% BID group and 86% of subjects (12 of 14) in the 1% QD group maintained response from Week 12 to Week 16. This secondary endpoint result indicates a durability of the effect of Tapinarof cream after the 12-week treatment period, and a sustained PGA treatment response.

An increasing proportion of subjects who had a PGA score of 0 or 1 at each study visit in the active treatment groups compared with the vehicle groups. The 1% concentration treatment groups showed a higher rate of responders than the 0.5% concentration groups at Week 12.

Decreasing PGA scores at each study visit in the active treatment groups compared with the vehicle groups.

Increasing mean change reductions in PGA scores from Baseline to each study visit in the active treatment groups compared with the vehicle groups.

Psoriasis Area and Severity Index (PASI): The main secondary objective of this study was to estimate the efficacy of GSK2894512 cream. The main secondary endpoint was the proportion of subjects with ≥75% improvement in PASI (PASI75) from Baseline to each study visit.

The planned repeated measures factorial logistic regression model with ITP did not fit the data well. Therefore summary statistics of the number of subjects providing data at the relevant time point, frequency counts and percentages, and 95% exact confidence interval were provided for the PASI75 response rate for each treatment group at each study visit.

Mean and 95% confidence interval were provided for the difference of (each BID dose—vehicle BID) and the difference of (each QD dose—vehicle QD) in PASI75 response rate at each visit.

The main secondary endpoint analysis showed a higher proportion of subjects in the active treatment groups than in the vehicle groups. The 1% concentration treatment groups showed a higher rate of responders than the 0.5% concentration groups, using the OC and LOCF imputation methods.

PASI secondary endpoint analyses revealed: A higher increasing mean percent change reduction in PASI scores from Baseline to each study visit in the active treatment groups than in the vehicle groups. The 1% concentration treatment groups showed a higher mean percentage change reduction than the 0.5% concentration groups at all visits.

The mean percent change reductions in PASI scores from Baseline continued to improve over time. The effects of Tapinarof cream on this parameter after QD and BID applications were similar.

An increased proportion of subjects with ≥75% improvement in PASI from Baseline to Week 12 was observed and this improvement was maintained at 2 and 4 weeks post-treatment in the active treatment groups compared with the vehicle groups. The 1% concentration treatment groups showed a more sustained improvement than the 0.5% concentration groups. Specifically, 80% (12 of 15) of subjects in the 1% BID group and 93% of subjects (12 of 14) in the 1% QD group maintained response from Week 12 to Week 16. This secondary endpoint result indicates a durability of the effect of Tapinarof cream after the 12-week treatment period, and a sustained PASI treatment response.

Psoriasis Area and Severity Index (PASI) Ad Hoc Analysis

Analyses of PASI endpoints PASI90, PASI=0, PASI≤1, PASI≤3 revealed: A higher proportion of subjects reached each endpoint in the active treatment groups than in the vehicle groups. The 1% concentration treatment groups showed a higher rate of responders than the 0.5% concentration groups, using OC data.

PASI90, PASI=0, PASI≤1, PASI≤3 continued to improve over time.

The effects of GSK2894512 cream on these endpoints (PASI90, PASI=0, PASI≤1 and PASI≤3) after QD and BID applications were similar.

Body Surface Area (BSA): A secondary objective was to assess the mean change in percent of total BSA affected from Baseline to each study visit.

An increase in the mean change reduction in percent of total BSA affected from Baseline to each study visit was higher in the active treatment groups than in the vehicle groups.

The increase in the mean change reduction in percent of total BSA affected from Baseline continued to improve over time. The effects of GSK2894512 cream on the mean change reduction in percent of total BSA affected from Baseline to each study visit after QD and BID applications were similar.

Target Lesion Grading: A secondary objective of the study was to assess the mean change in total target lesion grading scores (erythema, scaling and induration/plaque thickness) from Baseline to each study visit.

An increase in the mean change reduction in total target lesion grading scores from Baseline to each study visit was higher from Week 2 in the active treatment groups than in the vehicle groups. Table 8 provides a summary of psoriasis target lesion grading scale.

TABLE 8

Summary of Psoriasis Target Lesion Grading Scale

| Visit | Category | | Percent change from Baseline: Tapinarof 1% cream twice daily | Tapinarof 1% cream once daily | Tapinarof 0.5% cream twice daily | Tapinarof 0.5% cream once daily | Vehicle cream twice daily | Vehicle cream once daily |
|---|---|---|---|---|---|---|---|---|
| Week 1 | Erythema | Mean | −12.50 | −17.14 | −9.95 | −14.25 | −6.55 | −3.13 |
| | Scaling | Mean | −25.00 | −24.29 | −12.37 | −20.97 | −17.26 | −9.38 |

TABLE 8-continued

Summary of Psoriasis Target Lesion Grading Scale

| | | | Percent change from Baseline | | | | | |
|---|---|---|---|---|---|---|---|---|
| Visit | Category | | Tapinarof 1% cream twice daily | Tapinarof 1% cream once daily | Tapinarof 0.5% cream twice daily | Tapinarof 0.5% cream once daily | Vehicle cream twice daily | Vehicle cream once daily |
| | Plaque thickness | Mean | −18.75 | −13.10 | −14.52 | −10.22 | −14.29 | −5.21 |
| Week 2 | Erythema | Mean | −25.52 | −35.68 | −23.61 | −28.13 | −7.25 | −4.94 |
| | Scaling | Mean | −32.55 | −32.81 | −35.00 | −34.38 | −33.33 | −8.95 |
| | Plaque thickness | Mean | −33.33 | −30.47 | −33.89 | −26.04 | −21.01 | −8.33 |
| Week 4 | Erythema | Mean | −44.94 | −51.88 | −45.54 | −35.48 | −19.05 | −11.22 |
| | Scaling | Mean | −55.65 | −53.49 | −50.89 | −51.34 | −36.51 | −13.46 |
| | Plaque thickness | Mean | −48.51 | −47.04 | −44.64 | −42.47 | −33.33 | −14.42 |
| Week 8 | Erythema | Mean | −62.50 | −65.06 | −62.33 | −50.81 | −28.70 | −15.28 |
| | Scaling | Mean | −70.51 | −71.79 | −60.00 | −68.01 | −44.44 | −16.20 |
| | Plaque thickness | Mean | −62.82 | −60.90 | −62.67 | −60.75 | −35.19 | −18.06 |
| Week 12 | Erythema | Mean | −77.65 | −81.88 | −76.52 | −65.06 | −18.42 | −22.81 |
| | Scaling | Mean | −78.79 | −83.33 | −78.03 | −72.76 | −34.21 | −25.88 |
| | Plaque thickness | Mean | −81.82 | −70.29 | −71.59 | −67.31 | −35.96 | −25.88 |
| Follow-up Week 14 | Erythema | Mean | −65.42 | −70.65 | −68.25 | −63.77 | −19.79 | −31.86 |
| | Scaling | Mean | −67.50 | −67.39 | −68.65 | −67.75 | −21.88 | −23.04 |
| | Plaque thickness | Mean | −67.50 | −70.29 | −67.86 | −67.39 | −30.21 | −27.94 |
| Follow-up/ Week 16 | Erythema | Mean | −78.33 | −74.24 | −59.47 | −73.96 | −20.37 | −15.74 |
| | Scaling | Mean | −77.50 | −71.59 | −57.95 | −69.79 | −21.30 | −12.96 |
| | Plaque thickness | Mean | −76.67 | −65.91 | −54.92 | −71.53 | −24.07 | −17.59 |
| Early WD | Erythema | Mean | −46.67 | −47.62 | −25.00 | 8.33 | −18.33 | −1.85 |
| | Scaling | Mean | −52.50 | −57.14 | −41.67 | −16.67 | −16.67 | −3.70 |
| | Plaque thickness | Mean | −46.67 | −60.71 | −33.33 | 0.00 | −20.00 | 20.37 |

Itch/Pruritus Severity: A secondary objective of the study was to assess the mean change in weekly itch/pruritus NRS item from Baseline to each study visit.

There was no clear difference in the mean change reduction in itch/pruritus from Baseline to each study visit between the active treatment groups compared to the vehicle groups. The same pattern was observed for subjects with a Baseline NRS score ≥4. Additionally, no clear difference was observed in the proportion of subjects with a Baseline NRS score ≥who achieved a minimum 4-point improvement in itch/pruritus NRS from Baseline to each study visit between the active treatment groups and the vehicle groups. A BID application appeared to be more beneficial when compared to vehicle. Overall, most patients had a decrease (minimum 4-point improvement) in itch/pruritus symptoms over the study period.

Severity of Psoriasis Symptoms: One of the secondary endpoints assessed during the study was the change over time in weekly psoriasis symptoms as recorded daily in the PSD. The PSD includes 16 items from the already established version of the PSD as well as 6 newly developed items.

Overall, mean change reduction in the weekly average scores from the PSD was generally higher in the active treatment groups than in the vehicle groups. Of interest, PSD questions #2, #11, #12, #13, #14, #17, #18, #19 and #20 revealed a high mean severity score (5.0 or above) at Baseline; by Week 12, scores from these items had reduced (improved) more in the active treatment groups compared with the vehicle groups.

Investigator Impressions: As part of the efficacy assessment, investigators' impressions of change in psoriasis symptom severity from Baseline to Week 12 were reported. Responses were rated by investigators as "very improved" or "moderately improved" in >80% of subjects in the 1% concentration groups and 76% to 85% in the 0.5% concentration groups. In the "very improved" category, a clear difference was observed between the active treatment groups and the vehicle groups.

Subject Impressions: A secondary endpoint was to monitor subject impressions of change in psoriasis symptom severity from Baseline to Week 12.

Figure 7:
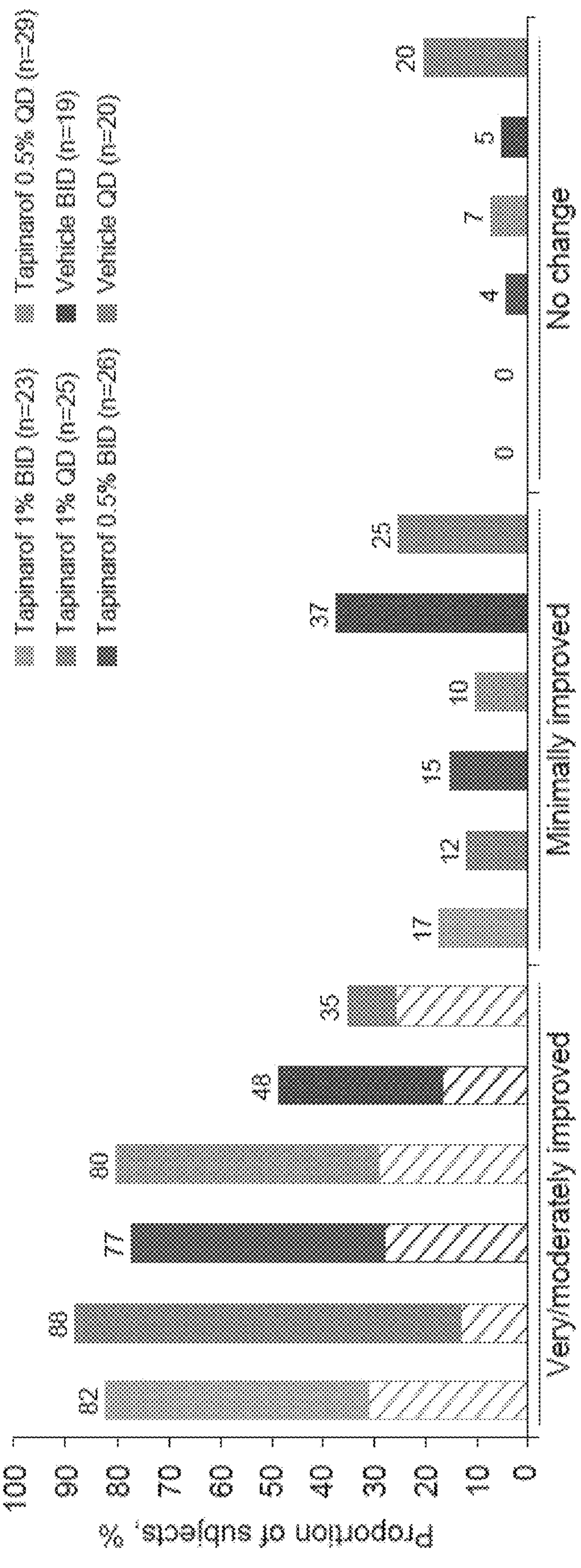
FIG. 7 depicts subject impression of change in severity of psoriasis symptoms at Week 12.
Figure 8:
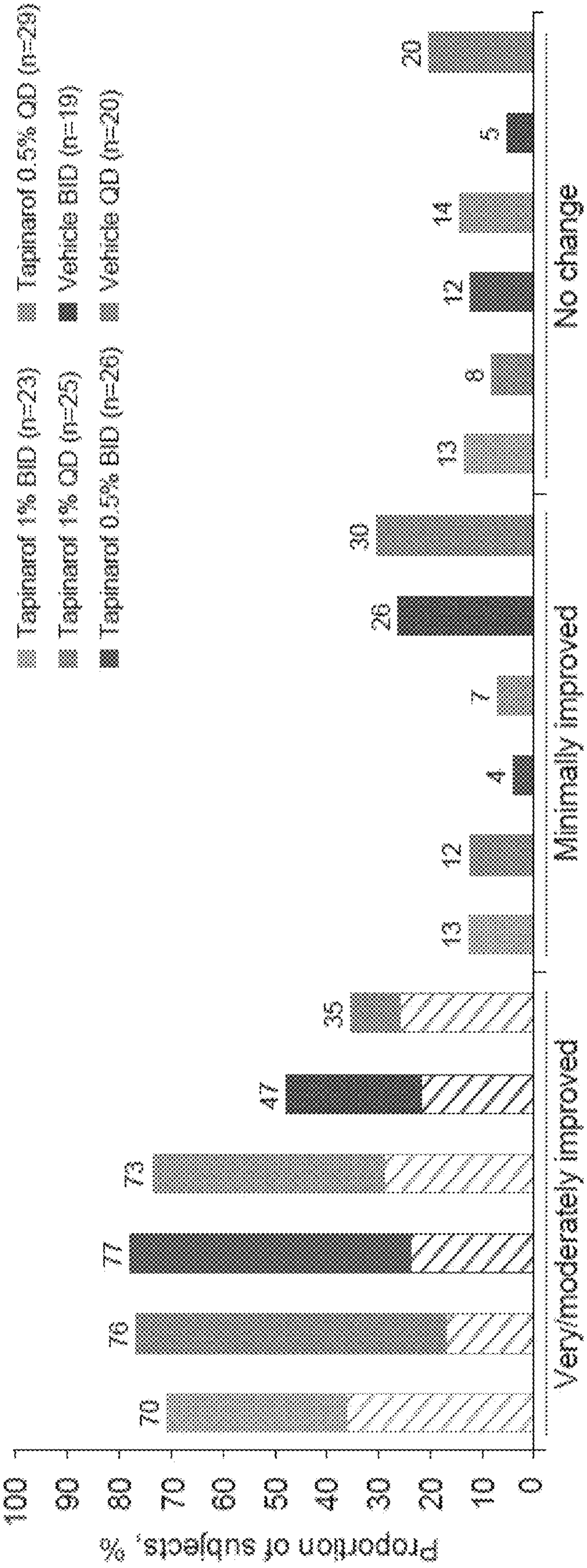
FIG. 8 depicts subject impression of change in severity of pruritus symptoms at Week 12.

At baseline, 88% of subjects rated their psoriasis symptoms as moderate or severe across all treatment groups: 43-61% rated as moderate and 28-44% rated as severe. At Week 12, most subjects in the tapinarof cream groups (82-88% in the 1% groups and 77-80% in the 0.5% groups) rated the severity of their overall psoriasis symptoms as 'very improved' or 'moderately improved' compared with 35-48% in the vehicle groups (FIG. 7). The majority of subjects treated with tapinarof cream (70-76% in the 1% groups and 73-77% in the 0.5% groups) rated the severity of their pruritus symptoms as 'very improved' or 'moderately improved' compared with 35-47% in the vehicle groups at Week 12 (FIG. 8).

Between 43% and 61% of subjects rated their Baseline psoriasis symptoms as moderate. At Week 12, most subjects in the Tapinarof groups (>80% in the 1% concentration groups and between 77-80% in the 0.5% concentration groups) rated the severity of their overall psoriasis symptoms as "very improved" or "moderately improved." Similarly, most subjects in the Tapinarof groups (70-77% in the 1% and 0.5% concentration groups) rated the severity of their itch symptoms as "very improved" or "moderately improved."

Sub-group Efficacy Analysis: Japanese Population: Out of the 227 subjects randomized in this study, 36 subjects were Japanese.

Primary and main secondary endpoint analyses for the Japanese sub-group were consistent with the Overall Population.

Global Assessment (PGA): The primary efficacy endpoint, the proportion of subjects who had a PGA score of 0 or 1 and a minimum 2-grade improvement in PGA score from Baseline to Week 12 was higher in the active treatment groups than in the vehicle groups. The 1% concentration treatment groups showed a higher proportion of responders than the 0.5% concentration groups, using the OC and the LOCF imputation methods. No responders were observed in the vehicle groups.

Psoriasis Area and Severity Index (PASI): The main secondary efficacy endpoint, the proportion of subjects with ≥75% improvement in PASI from Baseline to each study visit was higher in the active treatment groups than in the vehicle groups (apart from Week 4, when the vehicle BID group exceeded both GSK2894512 0.5% groups). The 1% concentration treatment groups showed a higher percentage of subjects with ≥75% improvement than the 0.5% concentration groups, in the OC and LOCF imputation methods.

Similarly, the increasing mean percent change reduction in PASI scores from Baseline to each study visit was higher in the active treatment groups than in the vehicle groups. The 1% concentration treatment groups showed a higher mean percentage change reduction than the 0.5% concentration groups with the OC and LOCF imputation methods.

Pharmacokinetics: One of the secondary objectives of this study was to characterize the population PK of GSK2894512 cream after topical application. Bioanalysis of the plasma samples from 225 subjects was performed. All PK samples were analyzed; however, all results were 'not reportable (NR)' due to the ISR failing to meet the acceptance criteria.

The bioanalytical method used to support the study was a fully validated Liquid Chromatography-Tandem Mass Spectrometry (LC-MS/MS) method in accordance with FDA/EU/MHLW guidelines [US Department of Health and Human Services, Food and Drug Administration Draft Guidance for Industry: Bioanalytical Method Validation, 2013] [European Medicines Agency Guideline on Bioanalytical Method Validation, 2011] [Japanese Ministry of Health Guideline on Bioanalytical Method Validation in Pharmaceutical Development, 2013].

One hundred and fifty samples (17% of total number of samples) were re-analyzed for ISR evaluation. It was observed that 55% of the ISR repeat results and original results were within 20% of the mean of the 2 values; this was not within the acceptance criteria (more than 66% of number of samples should be within 20%). The ISR investigation provided no assignable cause to explain the high variability on re-analyzing study samples. Further investigation of ISR failure could not be performed due to the sample depletion.

Plasma concentrations were measured for 860 samples from patients receiving an active dose of Tapinarof; 649 samples were below the Lower Limit of Quantitation (LLQ), 54 samples were not measurable and 157 samples were quantified. Based on the available data, the plasma concentrations samples fell mainly within the region of the assay LLQ. Generally, there was an aspect of the bioanalytical methodology that led to variability (e.g., extraction) in the region near the LLQ. In fact, the acceptance criteria for accuracy and precision at LLQ were 20% wider than at higher concentrations (15%) according to MHLW guideline. Therefore, lower exposures in psoriasis may likely have contributed to the ISR variability. Additionally, these lower levels of systemic exposures were not unexpected as a low total BSA was treated in the study (6.32%).

As a result of the NR data, one of the secondary objectives of the study, the exploration of the relationship between topical application (as cream concentration and % BSA treated), efficacy and/or safety, and systemic exposure of Tapinarof, was not met.

An increased understanding of PK for both indications will come from the planned maximum use pharmacokinetics (MUPK) studies, which will use a new bioanalytical method with a lower LLQ.

Safety Results

Safety results are reported using the Safety Population. Unless mentioned otherwise, results reported in this section are those of the Overall Population.

Adverse Events: Treatment-emergent adverse events (TEAEs) were reported in 104 subjects (46%) (the Safety Population comprised 227 subjects). The frequency of TEAEs was higher in the active treatment groups than in the vehicle groups (85/152 subjects [56%] vs 19/75 subjects [25%]).

TEAEs were considered treatment-related in 36/227 subjects (16%); most of these subjects were in the active treatment groups compared with the vehicle treatment groups (34/152 [22%] vs 2/75 [3%]) (approximately 33% females and 67% males). Sixteen of 227 subjects (7%) permanently discontinued treatment due to TEAEs (15/152 [10%] in the active treatment groups vs 1/75 [1%] in the vehicle treatment groups). Seven subjects (3%) experienced serious TEAEs (all were reported from the active treatment groups). Treatment-emergent adverse events (TEAEs) were reported in 46% of patients (68% [1% BID]; 53% [1% QD]; 58% [0.5% BID]; 45% [0.5% QD]; 24% [vehicle BID], and 26% [vehicle QD]) with most TEAEs reported as mild to moderate intensity. The most commonly (≥5%) reported TEAEs (regardless of relationship to study treatment) were folliculitis (20/227, 9% [19/152, 13% tapinarof groups and 1/75, 1% vehicle groups]) and contact dermatitis (12/227, 5%; all in the tapinarof groups [12/152, 8%]). Folliculitis was also the most frequent (≥5%) treatment-related 260 TEAE (16/227, 7% overall; 15/152 [10%] tapinarof groups vs 1/75 [1%] vehicle groups). Other treatment related TEAEs were: contact dermatitis (3%) (all tapinarof groups) and application site dermatitis, application site irritation, allergic dermatitis, monocyte count decreased and headache (1% each) (all tapinarof groups except for one case of monocyte count decreased, occurring in a vehicle patient). TEAEs led to permanent discontinuation of study treatment in 16/227 (7%) patients (15/152 [10%] tapinarof groups vs 1/75 [1%] vehicle groups). Contact dermatitis was the most common reason for study treatment permanent discontinuation, occurring in 6/227 (3%) of patients (all in tapinarof groups), patch testing was not performed to evaluate if these were cases of allergic or irritant contact dermatitis. Two patients treated with 1% tapinarof (1-QD group, 1-BID group) permanently discontinued treatment due to 'application site dermatitis'. Tolerability improved from Week 1 to Week 12 in both concentration groups (0.5% and 1%) and with both frequencies of application (QD or BID). The 1% QD treatment may have a slightly better tolerability profile than the 1% BID treatment, based on a lower frequency of TEAEs. Eight SAEs (alcoholic pancreatitis, dehydration, malignant melanoma [not at application site], hemolytic uremic syndrome, coronary artery disease, enlarged uvula, acute cardiac failure and atrial fibrillation) were reported in 7 patients (3%), all in tapinarof groups, none were treatment-related judged by the investigators. All patients, except the patient with malignant melanoma, had a pre-existing illness related to the event. In addition, there were no clinically-significant differences in mean changes in vital signs, ECG parameters, and laboratory evaluations between study groups during the study.

Most TEAEs were reported as mild (41/152 [27%] in the active treatment groups vs 13/75 [17%] in the vehicle treatment groups) or moderate (33/152 [22%] in the active treatment groups vs 4/75 [5%] in the vehicle treatment groups). Thirteen subjects (6%) experienced severe TEAEs (11/152 [7%] in the active treatment groups vs 2/75 [3%] in the vehicle treatment groups). None of the serious TEAEs were treatment-related.

The most frequently reported TEAE was folliculitis, which occurred in 20 subjects (9%) (19/152 [13%] in the active treatment groups vs 1/75 [1%] in the vehicle treatment groups). Other TEAEs included contact dermatitis, reported in 12 subjects (5%); (all reported in the active treatment groups), nasopharyngitis, reported in 9 subjects (4%) (7/152 [5%] in the active treatment groups vs 2/75 [3%] in the vehicle treatment groups), headache in 8 subjects (4%) (6/152, [4%] in the active treatment groups vs 2/75 [3%] in the vehicle treatment groups) and vomiting, reported in 4 subjects (2%) (3/152 [2%] in the active treatment groups vs 1/75 [1%] in the vehicle treatment groups).

The following TEAEs were each reported in 3 subjects (1%) each: atrial fibrillation (1 subject in the 1% QD group, 1 in the 0.5% BID and 1 in the vehicle group; none had any relevant medical history), hypertension (1 subject in the 1% QD group, 1 in the 1% BID and 1 in the 0.5% BID group; none had any prior medical history), acne, application site dermatitis, application site irritation, arthralgia, laceration, miliaria, back pain, allergic dermatitis, gastritis, ligament sprain, monocyte count decreased, pruritus, upper respiratory tract infection and urticaria.

TEAEs considered treatment-related by the investigators consisted mainly of folliculitis, which occurred in 16 subjects (7%) (15/152 [10%] from the active treatment groups vs 1/75 [1%] from the vehicle treatment groups (approximately 7% females and 7% males had this TEAE). Other treatment-related TEAEs were: contact dermatitis in 7 subjects (3%) (all in the active treatment groups), application site dermatitis and application site irritation, in 3 subjects each (1% each)(all in the active treatment groups), allergic dermatitis in 2 subjects (1%) (both in the active treatment groups), monocyte count decreased in 2 subjects (1%) (1/152 [1%] in the active treatment groups vs 1/75 [1%] in the vehicle treatment groups) and headache in 2 subjects (1%) (both in the active treatment groups).

Treatment-emergent AEs led to permanent discontinuation of study treatment in 16 subjects (7%). The frequency was higher in the active treatment groups than in the vehicle groups (15/152 [10%] in the active treatment groups vs 1/75 [1%] in the vehicle treatment groups). Contact dermatitis was the most frequent TEAE that led to study treatment discontinuation; it was reported in 6 subjects (3%), all in the active treatment groups, 5 of whom were treated with the higher GSK2894512 cream concentration (1% QD and BID), and 1 was treated with GSK2894512 cream 0.5% QD. Application site dermatitis was the next most frequent TEAE leading to study treatment discontinuation; it was reported in 2 subjects, both of them treated at the higher GSK2894512 cream concentration (1% QD and BID).

Serious and Other Significant Adverse Events

Deaths: No deaths were reported during the study.

Other Serious Adverse Events: Serious TEAEs were reported in 7 subjects (3%), all of whom were in the Tapinarof treatment groups Brief summaries of these serious TEAEs are provided below.

Acute cardiac failure and atrial fibrillation: A 55-year-old male with a previous history of diabetes mellitus, hyperlipidemia, and atrial fibrillation was randomized to receive Tapinarof 0.5% BID. The subject was hospitalized due to acute cardiac failure and atrial fibrillation 53 days after the first application. Study treatment was interrupted for 4 days. The subject was treated and events were resolved 40 days later. The investigator considered the events were unrelated to study treatment.

Alcoholic pancreatitis: A 42-year-old male was randomized to receive Tapinarof cream 1% BID. The subject experienced abdominal pain, nausea and vomiting and was hospitalized due to acute pancreatitis 5 days after the first application of study treatment. He reported several recent celebrations and had increased his alcohol intake during that time. He was treated with ondansetron, pantoprazole, intravenous fluids and morphine. Study treatment was continued. The event resolved after 2 days. The investigator considered that the event was not related to study medication.

Dehydration: A 37-year-old male was hospitalized due to dehydration (grade 3) 49 days after the first application of Tapinarof cream 0.5% BID. The subject ingested large quantities of beer 24 hours before the event; he was outdoors on a hot day and did not stay hydrated. The subject received intravenous fluids and dehydration resolved on the same day. The investigator considered that the event was unrelated to the study treatment.

Malignant melanoma: A 58-year-old male with a history of sun exposure and a sister with a history of malignant melanoma received Tapinarof cream 0.5% BID. The subject developed grade 3 malignant melanoma in an anatomically distinct area separate from the site of study treatment application, 16 days after the first application of study treatment. Study treatment was continued. Surgery was performed and the event resolved after 28 days. The investigator considered that the event was unrelated to study treatment.

Hemolytic uremic syndrome: A 43-year-old male with a personal and family history of hemolytic uremic syndrome due to an inherited enzyme deficiency received Tapinarof cream 1% QD. The subject was hospitalized due to grade 3 renal failure 59 days after the first application of study treatment. The event resolved and the subject was discharged after 2 days. No abnormalities were observed at any of the subject's scheduled laboratory investigations. The investigator considered that the event was not related to study treatment.

Coronary artery disease: A 61-year-old male experienced grade 3 coronary artery disease 80 days after the first application of Tapinarof cream 1% QD. The subject was hospitalized. He had a history of coronary artery bypass surgery, diabetes mellitus, hypercholesterolemia, and hypertension. Study treatment was discontinued and the subject was treated with furosemide, clopidogrel, perindopril, and metoprolol. The event resolved 10 days later. The investigator considered that the event was unrelated to study treatment.

Enlarged uvula: A 52-year-old male was hospitalized due to uvula swelling (grade 3) 9 days after the first application of Tapinarof cream 1% QD. The subject had a history of unreported intermittent uvula swelling since beginning lisinopril treatment, and was taking lisinopril during the study. The subject was treated with methylprednisolone sodium succinate, diphenhydramine, famotidine, sodium chloride, paracetamol, dexamethasone, and zolpidem tartrate. Tapinarof cream was continued. The event resolved 2 days later. The investigator considered that the event was not related to the study treatment.

Other Significant Adverse Events: No other significant AEs were reported during the study. However, a summary of the details of the 4 most frequently reported AEs is provided below.

Folliculitis: A total of 20 out of 227 (9%) subjects (15 male, 5 female; aged between 21 to 63 years), experienced folliculitis, 19 from the active treatment and 1 from the vehicle groups. Most of these events were reported from GSK2894512 1% BID group (8/20, 40%). A majority of the events were mild (15/20, 75%) and the rest were considered moderate (5/20, 25%). No severe events were reported. Treatment was withdrawn in one subject due to the event. Most (14/20, 70%) of the events occurred at the study drug application site. The median time to onset (since Day 1) was 24.5 days (26 days in the active treatment groups and 8 days in the vehicle groups). Fifteen (75%) cases were considered either resolved or resolving at the time of the report. Where the event resolved, the median duration of the event was 48.5 days (55 days in the active treatment groups and 7 days in the vehicle groups). A majority (16/20, 80%) of these events were considered related to study treatment by the investigators.

Contact dermatitis: A total of 12 out of 227 (5%) subjects (7 male, 5 female; aged between 29 to 61 years) experienced contact dermatitis, all from the active treatment groups. Three of the 12 subjects experienced irritant contact dermatitis. Most of these events were reported from Tapinarof 1% groups (8/12, 67%), 4/12 (33%) from the 1% BID group and 4/12 (33%) from the 1% QD group. A majority of the events were of moderate intensity (7/12, 58%), 4/12 (33%) were considered mild and 2/12 (17%) were considered severe. Six subjects (6/12, 50%), including 2 subjects with irritant contact dermatitis, had treatment withdrawn due to the event. At the time of the report, events were ongoing in 1 subject, had an unknown outcome in 1 subject and were considered either recovered or resolved in 10 (83%) subjects. Half (6/12, 50%) of the events occurred at the study drug application site. The median time to onset (since Day 1) was 30 days. The median duration of the event was 32 days. Over half (7/12, 58%) of these events were considered related to study treatment by the investigators.

Nasopharyngitis: A total of 9 out of 227 (4%) subjects (7 male, 2 female; aged between 33 to 65 years) experienced nasopharyngitis, 7 of whom (7/9, 78%) were from the active treatment groups. Most of these events were reported from Tapinarof 0.5% BID group (4/9, 44%), 2 from the Tapinarof 0.5% QD group (2/9, 22%), 1 from the GSK2894512 1% BID group (1/9, 11%), and 2 from the vehicle groups (2/9, 22%). A majority of the events were of mild intensity (7/9, 78%) and 2 (2/9, 22%) were considered moderate in intensity. No subjects had treatment withdrawn due to the event and no events were ongoing at the time of reporting (all cases were considered recovered or resolved at the time of the report). The median time to onset (since Day 1) was 45 days (13 days in the active treatment groups and 63.5 days in the vehicle groups). The median duration of the event was 7 days (12 days in the active treatment groups and 7 days in the vehicle groups). None of the events were considered related to study treatment by the investigators.

Headache: A total of 8 out of 227 (4%) subjects (6 male, 2 female; aged between 29 to 60 years) experienced headache, 6/8 (75%) from the active treatment groups and 2/8 (25%) from the vehicle groups. Half of these events were reported from Tapinarof 1% BID group (4/8 [50%]). The majority of the events (6/8, 75%) were of a mild nature, 1 (1/8, 13%) was considered moderate and one (1/8, 13%) was considered severe. No subjects had treatment withdrawn due to the event and no events were ongoing (all cases were considered recovered or resolved) at the time of reporting. The median time to onset (since Day 1) was 5 days (2.5 days in the active treatment groups and 60 days in the vehicle groups). The median duration of the event was 1 day (3 days for the active treatment groups and 1 day for the vehicle groups). Two (2/8, 25%) of the events were considered related to study treatment by the investigators.

Clinical Laboratory Evaluations

No clinically-significant changes in laboratory evaluations were reported during the study.

Four subjects experienced ALT and/or AST elevation >2×ULN; two each in active and vehicle treatment groups. Of these four patients, one (a 51-year-old female) in the Tapinarof cream 1% BID group had ALT >3×ULN approximately 1 month after the first exposure to study treatment (Week 4). The elevation did not meet the liver stopping criteria and the study treatment was continued. The event resolved after 20 days. Of the remaining three patients, one had AST >2×ULN and two had ALT >2×ULN. Except in one patient, the elevated AST or ALT values resolved within 2 weeks despite study treatment continuation.

Two patients (a 19- and a 29-year-old, both with baseline bilirubin levels above normal), had bilirubin elevations over 1.5×ULN. Both of them were treated in the vehicle groups. These abnormalities were not accompanied by ALT/AST abnormalities. The event resolved after 2 weeks in one of the patients (the 29-year-old) and remained elevated throughout the study in the other patient (the 19-year-old).

Other Safety Evaluations: No clinically-significant ECGs were observed in this study. A summary of change from Baseline in ECG values over time did not demonstrate any abnormalities.

Tolerability Evaluations: One of the secondary objectives of the study was to describe the tolerability of Tapinarof cream by measuring local (application site) tolerability scores as a secondary endpoint.

No difference in tolerability scores was reported by subjects between the 2 Tapinarof cream concentrations (0.5% and 1%) or between the 2 frequencies of application (QD or BID) tested. Tolerability scores improved during the course of the study. The proportion of subjects with the best tolerability score (score 0 or "none") increased from Week 1 to Week 12 across all study treatment groups. The number of subjects who permanently discontinued the study treatment due to potential tolerability issues was relatively small (approximately 8 subjects in total), which does not affect the interpretation of the overall tolerability trend.

Investigators assessed most subjects (≥70%) as having the lowest irritation score (0 or "no irritation") from Week 1 onwards.

Pregnancies: No pregnancies were reported during the study.

Immunoglobulins and Immunophenotyping: No clinically-significant changes were observed in Immunoglobulins (IgA, IgG, and IgM) across all treatment groups receiving either Tapinarof or vehicle and regardless of dosing frequency.

No clinically-significant changes were observed in Immunophenotyping across all treatment groups receiving either Tapinarof or vehicle regardless of dosing frequency.

Health Outcomes

One of the objectives of this study was to describe the effect of Tapinarof cream on subject-reported outcomes, for which subjects completed the PSD (including the NRS itch/pruritus item) as well as 2 global impressions of change items Discussion and Conclusions Discussion The objective of this randomized, double-blind, vehicle-controlled Phase II study was to evaluate the efficacy and safety of 2 doses of Tapinarof cream (0.5% or 1%) applied either QD or BID in adult subjects with psoriasis over 12 weeks. The characterization of population PK of Tapinarof cream after topical application was also an objective of the study; however, plasma concentrations were not reported mainly due to the ISR failing to meet the acceptance criteria. Bioanalysis and data were not reported.

Study Population: The population enrolled in this study was consistent with a moderate to severe psoriasis patient population. Specifically, subjects had a mean PGA score of 2.9 and 3.0 in the overall and the Japanese populations, respectively. Demographic and Baseline characteristic were generally similar across treatment groups.

Efficacy Discussion

Treatment success defined by PGA 0 or 1 and a 2-Grade Improvement at Week 12 were statistically significantly higher (at a 0.05 significance level) in the tapinarof groups than the vehicle groups: (65% [1% BID]; 56% [1% QD]; 46% [0.5% BID]; 36% [0.5% QD]; 11% [vehicle BID], and 5% [vehicle QD]) and was maintained for 4 weeks post treatment. Treatment-emergent adverse events (TEAEs) were higher with tapinarof (85/152 patients [56%] compared to vehicle 19/75 patients [25%]) and mild-to-moderate in intensity. Severe TEAEs were reported in all tapinarof groups except 0.5% QD. Study results showed a clear difference between the active treatment (Tapinarof cream) and the vehicle groups with regards to the primary endpoint (proportion of subjects who achieved a PGA score of 0 or 1 at Week 12 and a minimum 2-grade improvement in PGA score from Baseline to Week 12). Moreover, the 1% concentration groups showed a higher proportion of responder subjects than the 0.5% concentration groups at Week 12. Responses started at Week 2 and increased in magnitude throughout the study with the 1% concentration groups, having a higher proportion of responders at each time point compared to the 0.5% concentration groups. PGA responses persisted for 4 weeks after the end of treatment. Both application frequencies (QD or BID) had a similar effect on the PGA response rate within each cream concentration.

Figure 9:
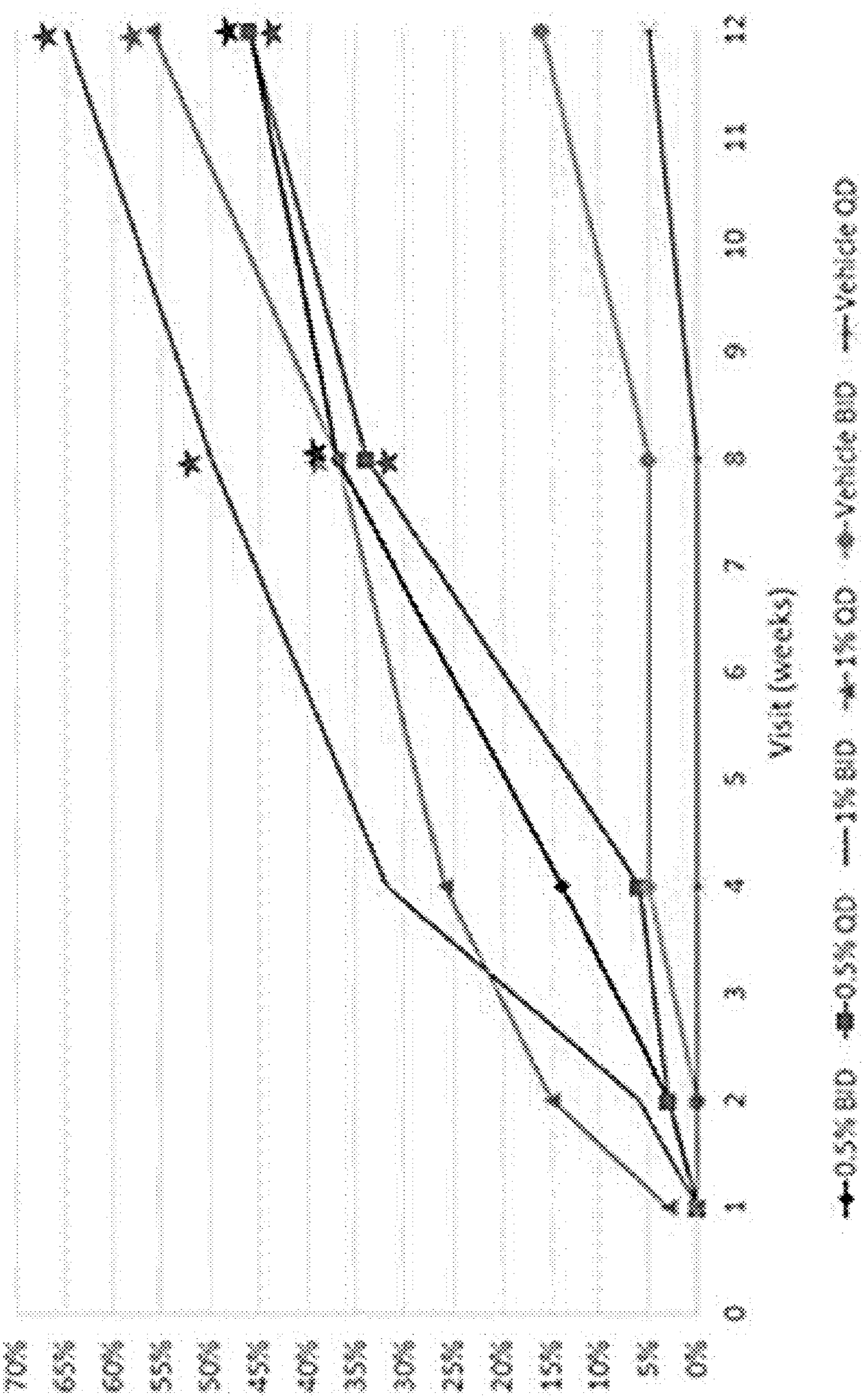
FIG. 9 depicts the proportion of patients with greater than or equal to 75% improvement in PASI from Baseline (mITT Population) (OC).

In a very similar pattern to the PGA response rate, the main secondary endpoint, the proportion of subjects with ≥75% improvement in PASI (PASI75) from Baseline to each study visit, was clearly higher in the active treatment than in the vehicle groups. All tapinarof groups showed a clear separation from vehicle reaching statistical significance after 8 weeks of treatment, with 1% concentration showing highest response rates (FIG. 9).

Similarly, the 1% concentration groups showed a higher proportion of responder subjects than the 0.5% concentration groups. Responses started at Week 2 and increased in magnitude throughout the study with the 1% concentration groups, having a higher proportion of responders at each time point compared to the 0.5% concentration groups. PASI75 responses lasted at least 4 weeks after the end of treatment. Mean percent change reduction in PASI scores from Baseline to each study visit, as well as the rate of PASI75 responders, was higher in the 1% concentration than in the 0.5% concentration groups.

Nearly identical improvement over time was observed for the mean percent change reduction in PASI scores for both 1% concentration groups (QD and BID), leading to the conclusion that the QD application had similar efficacy level to BID and would provide lower exposure than BID; therefore, it should be chosen for future Phase III studies. Also, the QD application offers an ease of use advantage that could lead to future subject treatment adherence.

The aforementioned efficacy results were unaltered when data were analyzed using a LOCF imputation method, confirming the robustness of the data.

Results from other clinical evaluations assessed from Baseline to each study visit such as mean change reduction in percent of total BSA affected, total target lesion grading scores (erythema, scaling and induration/plaque thickness) and subject-reported outcomes (severity of psoriasis daily symptoms) as assessed by subject responses recorded in a daily symptom diary, were also supportive of the therapeutic effect of Tapinarof cream, as compared to vehicle. However, the secondary endpoint of itch/pruritus severity did not follow this pattern; despite most subjects experiencing a decrease in itch/pruritus symptoms over the study period, no clear differences were observed between the active treatment groups and the vehicle groups in the reduction of the symptom of itch/pruritus.

Subject's impressions of the severity of their psoriasis symptoms from Baseline to Week 12, as well as investigators' assessments, corresponded with the clinical evaluations.

Most subjects rated the change in the severity of their psoriasis symptoms, as well as the change in the severity of their itch symptoms, as "very improved" or "moderately improved" by the end of 12 weeks of treatment with Tapinarof cream. Mean change reduction in weekly average PSD symptom scores was higher in the active treatment groups than in the vehicle groups. Further, when data from 9 items with high severity scores at baseline were analyzed, weekly average change scores improved more for active treatment groups when compared to the vehicle groups at Week 12.

Primary and main secondary endpoint analyses for the Japanese sub-group were consistent with the Overall Population.

Safety Discussion: The frequency of TEAEs was higher in the active treatment groups than in the vehicle groups (56% and 25%, respectively) and more TEAEs were considered treatment-related in the active treatment groups (22%) than in the vehicle groups (3%). Most TEAEs were mild or moderate, with 7% and 3% (in the active treatment and the vehicle groups, respectively) being reported as severe. No deaths, no other significant AEs and no clinically-significant changes in laboratory evaluations were reported during the study. The 1% QD treatment may have a slightly better safety profile than the 1% BID treatment, based on a lower frequency of TEAEs.

The most commonly reported TEAE (regardless of relationship to study treatment) was folliculitis (9%), which was also the most frequent treatment-related TEAE (7%) (10% and 1% in the active treatment and the vehicle groups, respectively). Other treatment-related TEAEs were: contact dermatitis (3%) (all in the active treatment group) and application site dermatitis, application site irritation, allergic dermatitis, monocyte count decreased and headache (1% each) (all in the active treatment groups except for 1 case of monocyte count decreased). The application site AEs occurred more frequently in the active treatment groups compared with the vehicle groups. The contact dermatitis may have been provoked by the topical treatment being directly applied on the skin; the application site dermatitis and the allergic dermatitis may have been related to the contact dermatitis. Headache was the fourth most frequent TEAE observed in this study, has already been reported in a Tapinarof Phase I study, and may show dose-response.

None of the serious TEAEs were treatment-related.

The tolerability of Tapinarof cream was very similar across concentration groups (0.5% and 1%) and with both frequencies of application (QD or BID). Tolerability improved from Week 1 to Week 12.

Safety: Overall, 46% (104/227) of subjects had treatment-emergent AEs (TEAEs): 56% in the tapinarof cream groups and 25% in the vehicle groups (Table 9), and were mostly mild to moderate in severity. The most frequently reported TEAE was folliculitis, which occurred in 20 (9%) subjects (13% in the tapinarof cream groups and 1% in the vehicle groups).

TABLE 9

Safety overview and most common TEAEs occurring in ≥5% of subjects in any group

| | Tapinarof 1% | | Tapinarof 0.5% | | Vehicle | |
|---|---|---|---|---|---|---|
| Preferred term, n (%) | BID (n = 40) | QD (n = 41) | BID (n = 43) | QD (n = 41) | BID (n = 42) | QD (n = 40) |
| Any TEAE | 26 (68) | 20 (53) | 22 (58) | 17 (45) | 9 (24) | 10 (26) |
| Treatment-related TEAEs | 10 (26) | 10 (26) | 6 (16) | 8 (21) | 1 (3) | 1 (3) |
| Serious TEAEs | 1 (3) | 3 (8) | 3 (8) | 0 | 0 | 0 |
| Discontinuous due to TEAEs | 5 (13) | 5 (13) | 4 (11) | 1 (3) | 0 | 1 (3) |
| TEAEs occurring in ≥5% of subjects in any group | | | | | | |
| Folliculitis | 8 (21) | 2 (5) | 4 (11) | 5 (13) | 1 (3) | 0 |
| Dermatitis contact | 4 (11) | 4 (11) | 1 (3) | 3 (8) | 0 | 0 |
| Headache | 4 (11) | 1 (3) | 0 | 1 (3) | 1 (3) | 1 (3) |
| Nasopharyngitis | 1 (3) | 0 | 4 (11) | 2 (5) | 0 | 2 (5) |
| Vomiting | 0 | 0 | 3 (8) | 0 | 1 (3) | 0 |
| Acne | 2 (5) | 0 | 1 (3) | 0 | 0 | 0 |
| Application-site dermatitis | 1 (3)* | 2 (5) | 0 | 1 (3) | 0 | 0 |
| Miliaria | 0 | 2 (5) | 0 | 1 (3) | 0 | 0 |
| Dermatitis allergic | 2 (5) | 0 | 0 | 0 | 0 | 0 |
| Urticaria | 0 | 2 (5) | 0 | 0 | 0 | 0 |

TEAE is defined as an AE which occurred on or after study treatment start date and on or before the last visit.
*All TEAEs occurred once in each subject except 'application site dermatitis', which occurred twice in a subject from the 1% BID group.
BID, twice daily; QD, once daily; TEAE, treatment-emergent adverse event.

Overall, Tapinarof cream showed an acceptable safety and tolerability profile.

Conclusions

The proportion of subjects who achieved a PGA score of clear or almost clear (0 or 1) at Week 12 and a minimum 2-grade improvement in PGA score from Baseline to Week 12 was clearly higher in the active treatment groups than in the vehicle groups and was dose-dependent.

PGA responses were observed from Week 2, peaked at around Week 12 and were durable, lasting up to 4 weeks after the end of treatment.

The effects of Tapinarof cream on the PGA response rate after QD and BID applications were similar.

The proportion of subjects with ≥75% improvement in PASI from Baseline to each study visit, was clearly higher in the active treatment groups than in the vehicle groups and was also dose-dependent.

PASI75 responses were observed from Week 2, peaked at around Week 12 and were durable, lasting up to 4 weeks after the end of treatment.

Mean percent change reduction in PASI scores from Baseline to each study visit, as well as the rate of early PASI75 responders, were higher in the 1% concentration group.

The effects of Tapinarof cream on the mean percent change reduction in PASI scores after QD and BID applications were similar, indicating that the QD application has similar efficacy level to BID and would provide lower exposure than BID; therefore, it should be chosen for future Phase III studies. Also, the QD application offers an ease of use advantage that could lead to future subject treatment adherence.

Evaluation of mean change reduction in percent of total BSA affected, total target lesion grading scores (erythema, scaling and induration/plaque thickness), and subject-reported outcomes (severity of psoriasis daily symptoms) as assessed by subject responses recorded in a personal symptom diary, were all supportive of the therapeutic effect of Tapinarof cream, as compared to vehicle.

Subject, as well as investigator impressions of the severity of psoriasis symptoms corresponded with clinical evaluations. Most subjects rated the change in the severity of their psoriasis symptoms as "very improved" or "moderately improved" by the end of treatment with Tapinarof cream (Week 12).

Tapinarof cream showed an acceptable safety profile. There were no treatment-related serious TEAEs reported.

The most frequent treatment-related TEAE was folliculitis, followed by contact dermatitis, application site dermatitis and application site irritation, allergic dermatitis, monocyte count decreased and headache.

No clinically-significant changes in laboratory evaluations were reported during the study.

The tolerability of Tapinarof cream was similar across concentration groups (0.5% and 1%) and with both frequencies of application (QD or BID). Tolerability improved from Week 1 to Week 12. The 1% QD treatment may have a slightly better safety profile than the 1% BID treatment.

Additional Analysis

Primary endpoint—efficacy based on percentage of patients who achieved minimum two-point improvement in PGA score and assessment of "clear" or "almost clear" skin, referred to as "treatment success."

Secondary endpoint—PASI score, BSA score, change in target lesion grading scores, psoriasis symptom diary scores, subject impressions of symptom severity and safety and tolerability.

At week 12, 65% of patients treated with 1% BID and 56% treated with 1% QD met treatment success, compared with 11% and 5% for vehicle BID and QD, respectively. At week 12, 46% of patients treated with 0.5% BID and 36% treated with 0.5% QD met treatment success.

At week 12, 65% and 56% of patients achieved a 75% improvement in PASI score in 1% BID and 1% QD groups, respectively, compared to 16% and 5% for BID and QD vehicle, respectively. The endpoint was met; statistical significance was achieved for all tapinarof arms compared to vehicle ($p<0.001$).

At week 12, subjects treated with both 0.5% and 1% concentrations showed greater improvement in mean change in percentage BSA affected from baseline (as demonstrated by an absolute mean change in percent BSA affected of 4.9 for 1% BID and 4.3 for 1% QD, respectively, compared with 1.6 for BID vehicle and 1.0 for QD vehicle). While statistical significance was not evaluated for this endpoint, the endpoint was determined to be met.

At week 12, subjects treated with both 0.5% and 1% concentrations showed greater improvement in mean change in total target lesion grading scores (decreases of 6.9 for 1% BID and 7.0 for 1% QD, compared with 2.5 for BID vehicle and 2.1 for QD vehicle). The maximum total target lesion grading score is 12 with a higher score indicating increased severity. The endpoint was met; statistical significance was achieved for all tapinarof arms compared to vehicle ($p<0.001$).

For psoriasis symptom diary scores, overall mean change reduction in the weekly average scores was generally higher in the treatment groups than in vehicle groups. While statistical significance was not evaluated for this endpoint, the endpoint was determined to be met.

At week 12, based on subject impressions of change in pruritus symptoms, most patients treated with tapinarof 1% (70% BID and 76% QD) and tapinarof 0.5% (77% BID and 72% QD) rated their itch to be "moderately improved" to "very improved" compared to patients treated with vehicle (47% BID and 35% QD). Statistical significance was achieved, and the endpoint was met, for all tapinarof arms compared to vehicle ($p<0.05$), with the exception of 1% BID.

At week 12, based on subject impression of symptom severity, most subjects in the treatment groups (over 80% in the 1% groups and between 77% and 79% in the 0.5% groups) rated the severity of their overall symptoms, including reduction in severity of itch, as "very improved" or "moderately improved." The endpoint was met; statistical significance was achieved for all tapinarof arms compared to vehicle ($p<0.05$).

There was no significant percentage change versus vehicle at week 12 for mean change in reduction in itch from baseline based on patients who achieved a minimum four-point improvement in the itch NRS. Overall, most patients had a minimum four point improvement in itch over the study period. As a result, we could not determine that this endpoint was met.

Generally well tolerated at 0.5% and 1% concentrations, with majority of AEs and TAEs reported as mild or moderate. 109 subjects experiences at least one AE (89 in treatment groups). 104 subjects experienced at least one TEAE (85 in treatment groups). 36 subjects experience TEAEs that were considered related to treatment (34 subjects in treatment groups). The most common treatment-related TEAs were folliculitis, contact dermatitis and headache. Seven subjects reported SAEs, none of which considered related to treatment. 16 subjects discontinued prior to end of treatment period.

Secondary Efficacy Outcomes from the Phase 2b, Randomized Dose-Finding Study of Tapinarof Cream for the Treatment of Plaque Psoriasis Study: This phase 2b, double-blind, six-arm, vehicle-controlled randomized study (NCT02564042) assessed the efficacy and safety of tapinarof cream in subjects with psoriasis. Subjects (aged 18-65 years) with chronic stable plaque psoriasis (≥6 months), BSA involvement ≥1 and ≤15% and Physician Global Assessment (PGA) score ≥2 at baseline were randomized 1:1:1:1:1:1 to tapinarof cream 0.5% or 1.0% once (QD) or twice daily (BID) or vehicle QD or BID for 12 weeks. Secondary efficacy outcomes reported here include mean change from baseline in PGA, 50% reduction in Psoriasis Area and Severity Index (PASI50), PASI90, target lesion grading scores, and pruritus numeric rating scale (NRS).

Results: Of 227 subjects randomized, 174 completed the study. Higher PASI50 and PASI90 response rates, and greater reductions in mean PGA and total target lesion grading scores were observed in tapinarof groups vs vehicle at Week 12; results were maintained for 4 weeks after the end of study treatment (Table 10). Most treatment-emergent adverse events were mild or moderate, and the most common (≥5%) across all groups were folliculitis (9%) and contact dermatitis (5%). Most incidences of folliculitis and contact dermatitis were mild or moderate.

Conclusion: These results support the primary analysis showing that tapinarof cream was efficacious and well tolerated in adults with psoriasis.[1] A phase 3 program is planned to further investigate tapinarof cream (1% QD) as a new treatment option for psoriasis.

TABLE 10

Secondary efficacy results at Week 12

| | Tapinarof 1% cream | | Tapinarof 0.5% cream | | Vehicle | |
|---|---|---|---|---|---|---|
| Mean change in PGA scores (SD) from baseline at Week 12 | BID (n = 23) −1.8* (0.9) | QD (n = 25) −1.7* (1.0) | BID (n = 26) −1.7* (1.1) | QD (n = 28) −1.3* (0.8) | BID (n = 19) −0.5 (0.8) | QD (n = 20) −0.4 (0.7) |
| Mean change in total target lesion grading scores (SD) from baseline at Week 12 | BID (n = 23) −6.9* (2.9) | QD (n = 25) −7.0* (3.1) | BID (n = 26) −6.2* (3.0) | QD (n = 29) −5.8* (3.0) | BID (n = 19) −2.5 (2.8) | QD (n = 20) −2.1 (2.2) |
| PASI50 response rates at Week 12 | BID (n = 23) 83%* | QD (n = 25) 92%* | BID (n = 26) 85%* | QD (n = 28) 71%* | BID (n = 19) 32% | QD (n = 20) 10% |
| PASI75 response rates at Week 12 | BID (n = 23) 65%† | QD (n = 25) 56%* | BID (n = 26) 46%‡ | QD (n = 28) 46%† | BID (n = 19) 16% | QD (n = 20) 5% |
| PASI90 response rates at Week 12 | BID (n = 23) 39%† | QD (n = 25) 40%† | BID (n = 26) 31%† | QD (n = 28) 18% | BID (n = 19) 0 | QD (n = 20) 0 |
| Proportion of subjects who achieved ≥4 improvement in pruritus NRS score from baseline at Week 12 for subjects with baseline NRS score ≥4 | BID (n = 11) 55% | QD (n = 11) 73% | BID (n = 18) 56% | QD (n = 14) 57% | BID (n = 10) 60% | QD (n = 12) 33% |

*P < 0.001 vs Vehicle.
†P < 0.01 vs Vehicle.
‡P < 0.05 vs Vehicle.

Patient-Reported Outcomes in Subjects with Plaque Psoriasis Treated with Tapinarof Cream: Results from a Phase 2b, Randomized Parallel-Group Study Study: This phase 2b, double-blind, six-arm, vehicle-controlled, randomized study (NCT02564042) assessed the efficacy and safety of tapinarof cream in subjects with psoriasis. Subjects (aged 18-65 years) with chronic stable plaque psoriasis (≥6 months), BSA involvement ≥1 and ≤15% and Physician Global Assessment score ≥2 at baseline were randomized 1:1:1:1:1:1 to tapinarof cream 0.5% or 1.0% once (QD) or twice daily (BID) or vehicle QD or BID for 12 weeks. The primary endpoint data was previously reported.[1] Patient-reported outcomes reported here include change in Psoriasis Symptom Diary (PSD) scores and subject global impression of overall severity of psoriasis symptoms and overall severity of pruritus from baseline to Week 12.

Results: Of 227 subjects randomized, 174 completed the study. Overall, 43-61% of subjects rated their baseline symptoms as moderate; 28-44% as severe; and 3-13% as very severe. At week 12, a greater proportion of subjects in the tapinarof groups rated the overall severity of their psoriasis symptoms and pruritus symptoms as 'very/moderately improved' compared with subjects in the vehicle groups (Table 11). Most treatment-emergent adverse events were mild or moderate, and the most common (≥5%) across all groups were folliculitis (9%) and contact dermatitis (5%). Most incidences of folliculitis and contact dermatitis were mild or moderate.

Conclusion: Subjects treated with tapinarof cream reported improvements in symptoms, including pruritus from psoriasis, after 12 weeks vs vehicle. Overall, tapinarof cream was well tolerated.

TABLE 11

Patient-reported outcomes results at Week 12

| | Tapinarof 1% cream | | Tapinarof 0.5% cream | | Vehicle | |
|---|---|---|---|---|---|---|
| Proportion of subjects with severity of psoriasis symptoms rated as 'very/moderately improved' from baseline to Week 12 | BID (n = 23) 83%‡ | QD (n = 25) 88%* | BID (n = 26) 77%‡ | QD (n = 29) 79%† | BID (n = 19) 47% | QD (n = 20) 35% |
| Proportion of subjects with severity of pruritus symptoms rated as 'very/moderately improved' from baseline to Week 12 | BID (n = 23) 70% | QD (n = 25) 76%† | BID (n = 26) 77%‡ | QD (n = 29) 72%‡ | BID (n = 19) 47% | QD (n = 20) 35% |
| Mean change in nine items of the PSD from baseline at Week 12 [range 1 (very improved) to 7 (very worse)] | BID (n = 14) −4.5‡ | QD (n = 20) −4.0† | BID (n = 21) −4.2‡ | QD (n = 24) −4.1† | BID (n = 15) −2.6 | QD (n = 18) −1.9 |

*P < 0.001 vs Vehicle.
†P < 0.01 vs Vehicle.
‡P < 0.05 vs Vehicle.

Example 3—Phase 2b, Randomized Clinical Trial of Tapinarof Cream for the Treatment of Plaque Psoriasis: Secondary Efficacy and Patient-Reported Outcomes Introduction Psoriasis is a chronic, immune-mediated disease that is characterized by scaly, erythematous and pruritic plaques that can be painful and disfiguring. The burden of psoriasis is similar to that of other long-term conditions, such as congestive cardiac failure and chronic lung disease, and has a profound impact on mental health and well-being.

Up to 71% of patients with psoriasis report a ‘moderate-to-extremely high impact’ on their daily life. People with psoriasis experience a high treatment burden, with 88% reporting use of prescription topical medications and 83% reporting concomitant use of prescription and over-the-counter therapies. Patient satisfaction and preferences are closely related to treatment compliance. For topical treatments, the vehicle can have a significant impact on adherence and long-term effectiveness, with patients preferring creams to ointments, as creams are considered less sticky and easier to apply.

Topical agents used as first-line therapy for psoriasis include vitamin D derivatives, corticosteroids, vitamin A derivatives (tazarotene), and anthralin. There are well-documented concerns and limitations with current topical treatments, for example the vitamin D derivative, calcipotriene cream (0.005%) has been associated with skin irritation and elevated serum calcium levels; the topical retinoid, tazarotene cream (0.05% and 0.1%), has adverse events (AEs) that include pruritus, erythema, and burning; and mid-to-high-potency topical steroids have limitations on duration and location of use due to concerns about local and systemic side effects. There is a clear need, therefore, for effective topical therapies that can be used without body surface area (BSA) restrictions or duration of treatment limitations.

Tapinarof cream is a first-in-class therapeutic aryl hydrocarbon receptor (AhR) modulating agent (TAMA) that is under investigation for the treatment of psoriasis and atopic dermatitis. The efficacy of tapinarof in psoriasis is attributed to AhR-modulated downregulation of interleukin-17, skin barrier function enhancement, and antioxidant properties via activation of the Nrf2 antioxidant pathway, a major regulator of cytoprotective responses.

In the primary analysis of a phase 2b study in adults with psoriasis, tapinarof cream was efficacious and well-tolerated. Here we report additional efficacy and patient-reported outcomes (PROs) to further explore the efficacy and tolerability of tapinarof cream in subjects with psoriasis.

Methods

Study design: In this multicenter (United States, Canada, and Japan), phase 2b, double-blind, vehicle-controlled study, adult subjects with psoriasis were randomized 1:1:1:1:1:1 to receive tapinarof cream 0.5% or 1% once (QD) or twice daily (BID) or vehicle QD or BID for 12 weeks and followed up for 4 weeks after the end of study treatment. Detailed study design and primary endpoints were reported above. The study consisted of 3 periods: up to 4 weeks' screening, 12 weeks' double-blind treatment, and 4 weeks' treatment-free follow-up. Study visits occurred at screening; baseline; Weeks 1, 2, 4, 8, and 12 during the treatment period; and 2 and 4 weeks after the last application of study treatment.

The study was conducted in compliance with the guidelines for Good Clinical Practice and the Declaration of Helsinki. Approval was obtained from the local ethics committee or institutional review board at each study center. All subjects provided written informed consent.

Subjects: Subjects were male or female adults aged 18-65 years, with a clinical diagnosis of chronic stable plaque psoriasis for ≥6 months, BSA involvement ≥1% to ≤15% (excluding scalp) at screening and baseline, Physician Global Assessment (PGA) score ≥2 at baseline, and 1 target plaque located on the trunk or proximal parts of the extremities (excluding knees, elbows, and intertriginous areas) that measured ≥3 $cm^2$ at screening and baseline with severity representative of the subject's overall disease. Key exclusion criteria were lesion infections and a history of, or ongoing, serious illness. Use of medications or treatments that would significantly influence or exaggerate responses to the study treatment were prohibited, including biologic agents, retinoids, immunomodulators, corticosteroids, and coal tar.

Study treatment: Subjects were instructed to apply a thin layer of tapinarof cream or vehicle to all psoriasis lesions (excluding scalp) QD or BID (at approximately the same time daily or 12 hours apart). Subjects were to continue to treat all original areas of involvement, even in the event of clearing of lesions, and were to apply cream to any new lesions.

Outcome measures and statistical analysis: The previously reported primary efficacy endpoint was the proportion of subjects with a PGA score of clear or almost clear (0 or 1) and ≥2-grade improvement in PGA score from baseline to Week 12. Additional efficacy outcomes included PGA scores, mean change in PGA and total target lesion grading scores, and ≥50%, ≥75%, and ≥90% improvement in Psoriasis Area and Severity Index (PASI50, PASI75, and PASI90) from baseline to each study visit.

PROs included change over time in daily Psoriasis Symptom Diary (PSD) scores and subject global impression of change in overall severity of psoriasis symptoms and pruritus symptoms from baseline to Week 12. The PSD is a disease-specific, psychometrically validated, daily self-report tool for the symptoms and functional impact of psoriasis. The PSD used included the 16 questions in the established version, plus 6 additional questions to assess the severity and bother of skin flaking, dryness, and bleeding. Each PSD item is rated using an 11-point Numeric Rating Scale, from 0 (absent) to 10 (worst imaginable). Subject global impression of change in overall severity of psoriasis symptoms and overall severity of pruritus symptoms from baseline to Week 12 were also assessed. Subjects were asked to rate the overall severity of their psoriasis symptoms and pruritus symptoms at baseline on a scale of 1 (mild) to 4 (very severe), and the change in overall severity of psoriasis symptoms and pruritus symptoms from baseline to Week 12 from 1 (very improved) to 7 (very worse).

Safety assessments included incidence, frequency and severity of AEs, evaluation of local (application-site) tolerability, clinical laboratory parameters, vital signs, electrocardiogram changes, and physical examinations. An unblinded Independent Data Monitoring Committee monitored patient safety. Investigators assessed the overall degree of irritation at the application sites using a scale of 0 (no irritation) to 4 (very severe/strong reaction) at each study visit. A score of 3 or 4 was reported as an AE. Study treatment was discontinued if a score of 4 was noted. Subject-reported tolerability was assessed using a 5-point tolerability scale of 0 (none) to 4 (strong/severe) to assess the presence and degree of burning/stinging and itching at the application site within 2 hours following application of tapinarof or vehicle.

Efficacy analyses were conducted on observed cases in the modified intention-to-treat (mITT) population, which included all randomized subjects minus the subjects from one site, due to a protocol violation. Summary statistics of the number of subjects providing data at the relevant time point, frequency counts and percentages, and 95% exact confidence interval were provided for each treatment group at each study visit.

Differences between arms were considered statistically significant at an α=0.05 level, where 95% confidence intervals excluded 0. P values for differences between tapinarof cream groups and corresponding vehicle groups for PASI response rates at Weeks 12 and 16 were calculated post hoc using Barnard's and Fisher's exact tests. P values for PGA scores and total target lesion grading scores at Weeks 12 and 16 were based on a post-hoc analysis of covariance with main effect of treatment and covariates of average baseline selected score and pooled country.

Results

Subject disposition: Of the 290 subjects screened, 227 were randomized, 196 were included in the mITT population, and 175 (77%) completed the 12-week treatment phase. Overall, mean demographic and baseline characteristics were comparable across treatment groups (Table 12). Most subjects (80%) had a baseline PGA category of 3 (moderate). Baseline mean PASI score was 8.8 (standard deviation, 4.5).

PASI50, PASI75, and PASI90: PASI50 and PASI75 response rates were significantly higher in all tapinarof groups compared with vehicle groups from Week 8 onwards. PASI50 response rates at Week 12 were 83% (1% BID), 92% (1% QD), 85% (0.5% BID), and 71% (0.5% QD) versus 32% (vehicle BID) and 10% (vehicle QD) (all P<0.001). Significant PASI50 responses with tapinarof were maintained after the end of treatment through Week 16: 83% (P<0.001; 1% BID), 77% (P<0.001; 1% QD), 62% (P=0.023; 0.5% BID), and 71% (P<0.001; 0.5% QD) versus 26% (vehicle BID) and 16% (vehicle QD).

Figure 10:
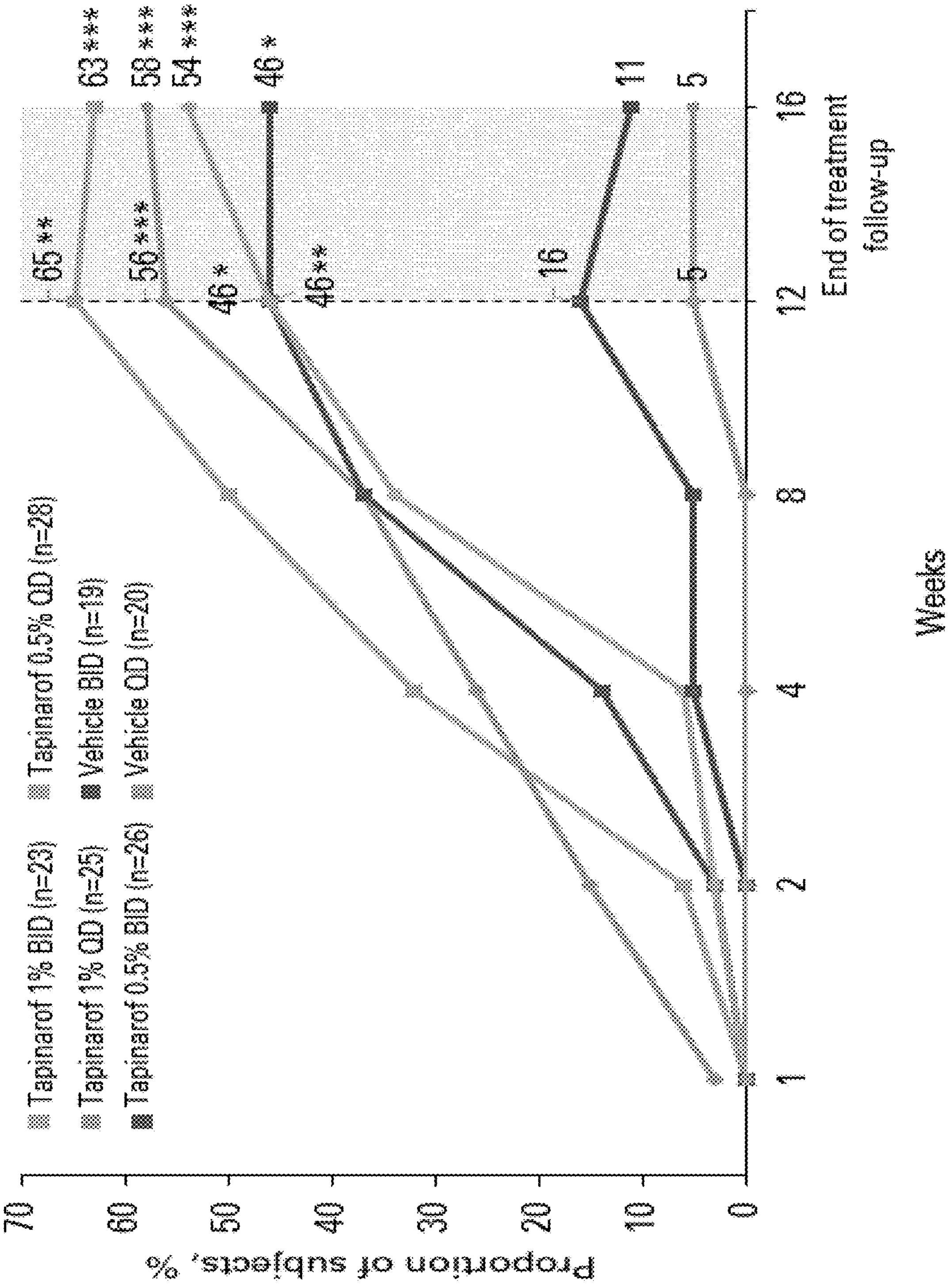
FIG. 10 shows the proportion of subjects with ≥75% improvement in Psoriasis Area and Severity Index from baseline to week 12 and week 16 (end of treatment follow-up). Difference versus vehicle is statistically significant at *P<0.05, P<0.01, *P<0.001. n designates the number of subjects with results available at week 12. BID, twice daily; QD, once daily.

PASI75 response rates at Week 12 were 65% (P=0.001; 1% BID), 56% (P<0.001; 1% QD), 46% (P=0.035; 0.5% BID), and 46% (P=0.002; 0.5% QD) versus 16% (vehicle BID) and 5% (vehicle QD). Significant PASI75 responses with tapinarof were maintained after the end of treatment through Week 16: 63% (P<0.001; 1% BID), 58% (P<0.001; 1% QD), 46% (P=0.012; 0.5% BID), and 54% (P<0.001; 0.5% QD) versus 11% (vehicle BID) and 5% (vehicle QD) (FIG. 10).

Figure 11:
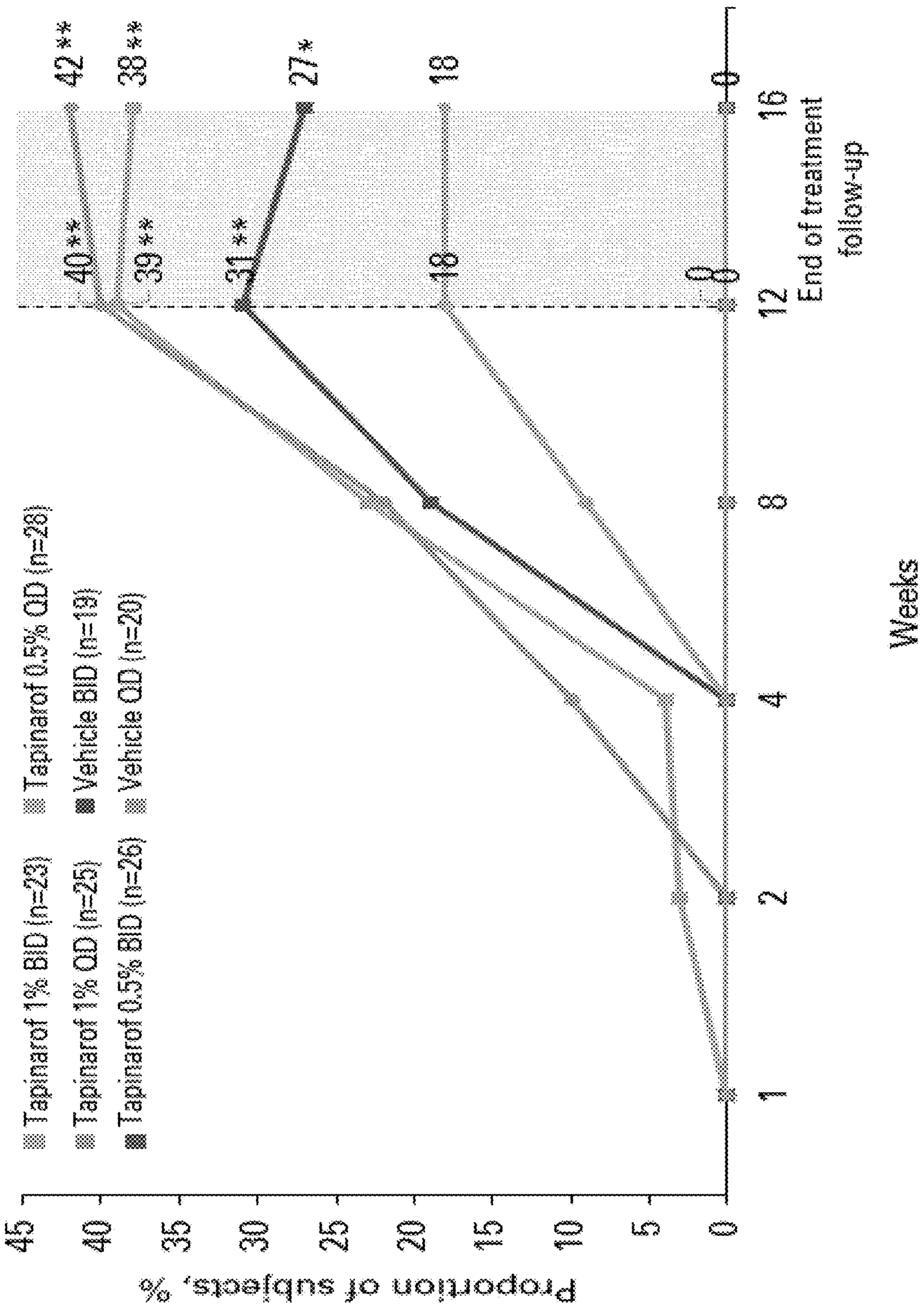
FIG. 11 shows the proportion of subjects with ≥90% improvement in psoriasis area and severity index from baseline to Week 12 and Week 16 (end of treatment follow-up). Difference versus vehicle is statistically significant at *P<0.05, **P<0.01. n is number of subjects with available results at Week 12. BID, twice daily; QD, once daily.

PASI90 responses rates were significantly higher in all tapinarof groups, except the 0.5% QD group, compared with vehicle at Week 12: 39% (P=0.002; 1% BID), 40% (P=0.001; 1% QD), 31% (P=0.008; 0.5% BID), and 18% (P=0.057; 0.5% QD); 0% (vehicle BID); and 0% (vehicle QD). Significantly higher PASI90 responses in the tapinarof groups were maintained after the end of treatment through Week 16: 38% (P=0.002; 1% BID), 42% (P=0.001; 1% QD), 27% (P=0.014; 0.5% BID), and 18% (P=0.057; 0.5% QD) versus 0% (vehicle BID) and 0% (vehicle QD) (FIG. 11).

PASI50/75/90 responses with tapinarof generally showed a separation versus vehicle starting at Week 2, with significantly superior efficacy maintained to Week 12 and after the end of treatment, through Week 16.

Figure 12:
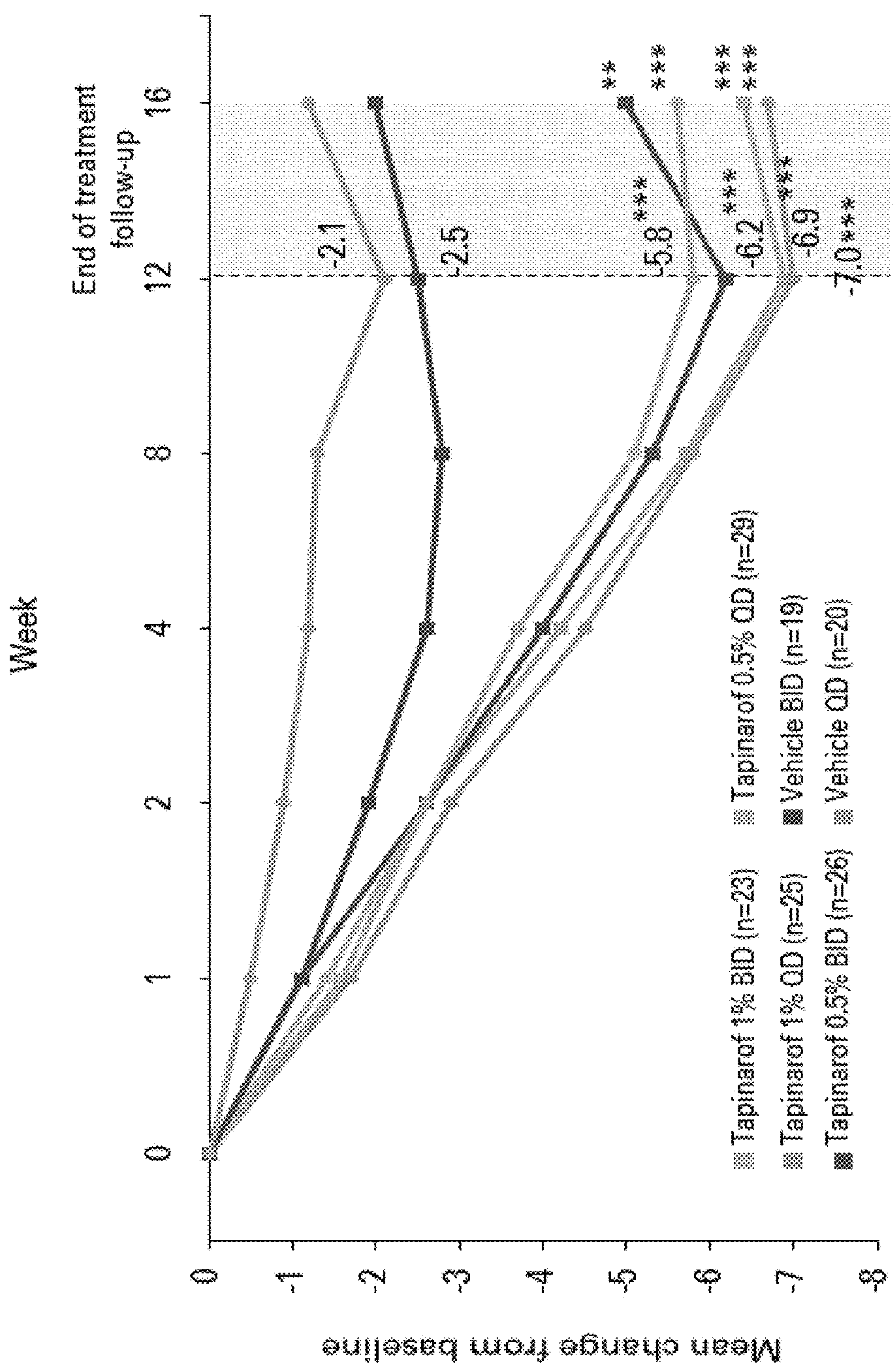
FIG. 12 depicts the mean change in total target lesion grading scores† from baseline to Week 12 and Week 16 (end of treatment follow-up). Difference versus vehicle is statistically significant at P<0.01, *P<0.001. n is number of subjects with available results at Week 12. †Erythema, scaling, and induration of plaque thickness. BID, twice daily; QD, once daily.

Total target lesion grading: Greater reductions in total target lesion grading scores from baseline were observed in all tapinarof groups compared with vehicle groups from Week 2 onwards, with significantly greater reductions observed at Week 12 (all comparisons P<0.001). Significant improvements in total target lesion grading scores with tapinarof versus vehicle were maintained after the end of study treatment through Week 16 (FIG. 12). The target

TABLE 12

Baseline subject demographics and characteristics

| | Tapinarof 1% cream | | Tapinarof 0.5% cream | | Vehicle | |
|---|---|---|---|---|---|---|
| | BID (n = 38) | QD (n = 38) | BID (n = 38) | QD (n = 38) | BID (n = 37) | QD (n = 38) |
| Age, mean (SD), years | 45.9 (11.9) | 48.5 (10.6) | 49.6 (10.9) | 48.7 (9.7) | 46.7 (12.6) | 46.4 (10.2) |
| Male sex, n (%) | 26 (68) | 26 (68) | 24 (63) | 25 (66) | 23 (62) | 29 (76) |
| Weight, mean (SD), kg | 85.6 (22.5) | 86.7 (22.6) | 88.6 (27.4) | 89.3 (23.1) | 87.8 (28.3) | 91.6 (21.6) |
| PGA score, mean (SD*) | 2.9 (0.4) | 2.7 (0.5) | 3.0 (0.5) | 2.9 (0.4) | 3.0 (0.3) | 2.8 (0.4) |
| PASI score, mean (SD)* | 10.6 (5.0) | 8.5 (3.6) | 8.2 (4.5) | 7.9 (4.8) | 9.0 (4.3) | 8.7 (4.4) |
| BSA affected, mean (SD), %* | 8.2 (4.5) | 6.5 (3.3) | 7.2 (4.5) | 6.1 (4.3) | 6.6 (3.6) | 7.0 (4.6) |
| Pruritus score, mean (SD)*† | 5.6 (2.6) | 4.4 (2.9) | 6.2 (2.2) | 4.5 (2.6) | 5.5 (2.8) | 4.9 (2.4) |

Primary efficacy endpoint: As previously reported, PGA response rate at Week 12 was significantly higher in all tapinarof cream groups compared with vehicle groups (65% [1% BID]; 56% [1% QD]; 46% [0.5% BID]; 36% [0.5% QD] vs 11% [vehicle BID] and 5% [vehicle QD]) and was maintained for 4 weeks after the end of treatment through Week 16 in all active treatment groups except for the 0.5% BID group. PGA response rates were significantly higher in all tapinarof groups compared with vehicle groups from Week 8 onwards.

Figure 13:
FIG. 13 shows plaque psoriasis at baseline (left panel), Week 8 (middle), and Week 12 (right panel). Representative photographs of one target lesion in one subject (randomized to receive tapinarof 1% QD) with baseline plaque psoriasis, plus responses at Week 8 and Week 12. QD, once daily.

PGA scores: Mean improvements in PGA scores (SD) from baseline at Week 12 were significantly higher in all tapinarof groups compared with vehicle groups (all P<0.001): −1.8 (0.9) 1% BID, −1.7 (1.0) 1% QD, −1.7 (1.1) 0.5% BID, and −1.3 (0.8) 0.5% QD versus −0.5 (0.8) vehicle BID and −0.4 (0.7) vehicle QD.

lesion response of a representative subject randomized to tapinarof 1% QD at baseline, Week 8, and Week 12 is shown in FIG. 13.

Figure 14:
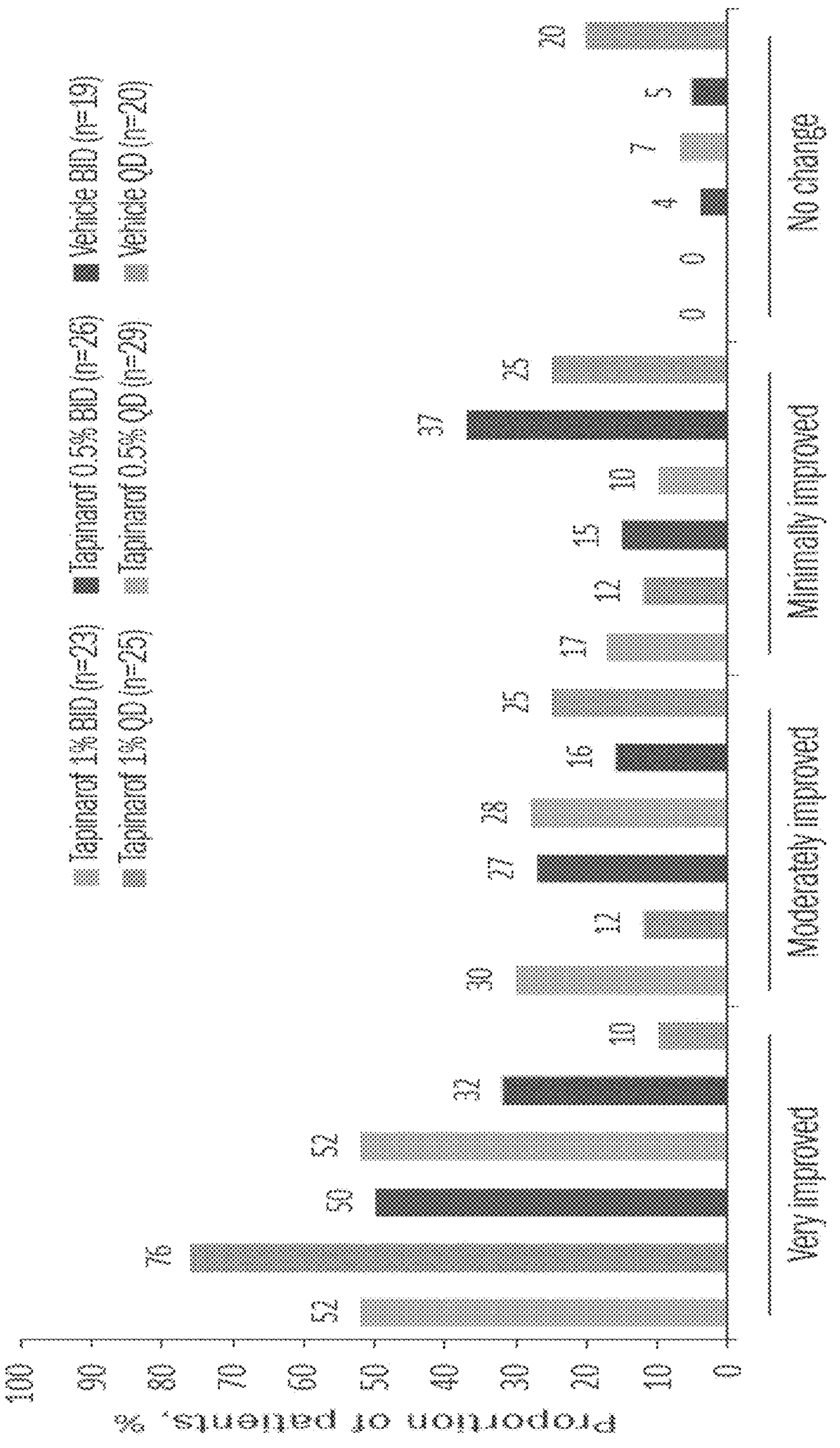
FIG. 14 depicts subject impression of change in severity of psoriasis symptoms at Week 12. n is number of subjects with available results at Week 12. BID, twice daily; QD, once daily.
Figure 15:
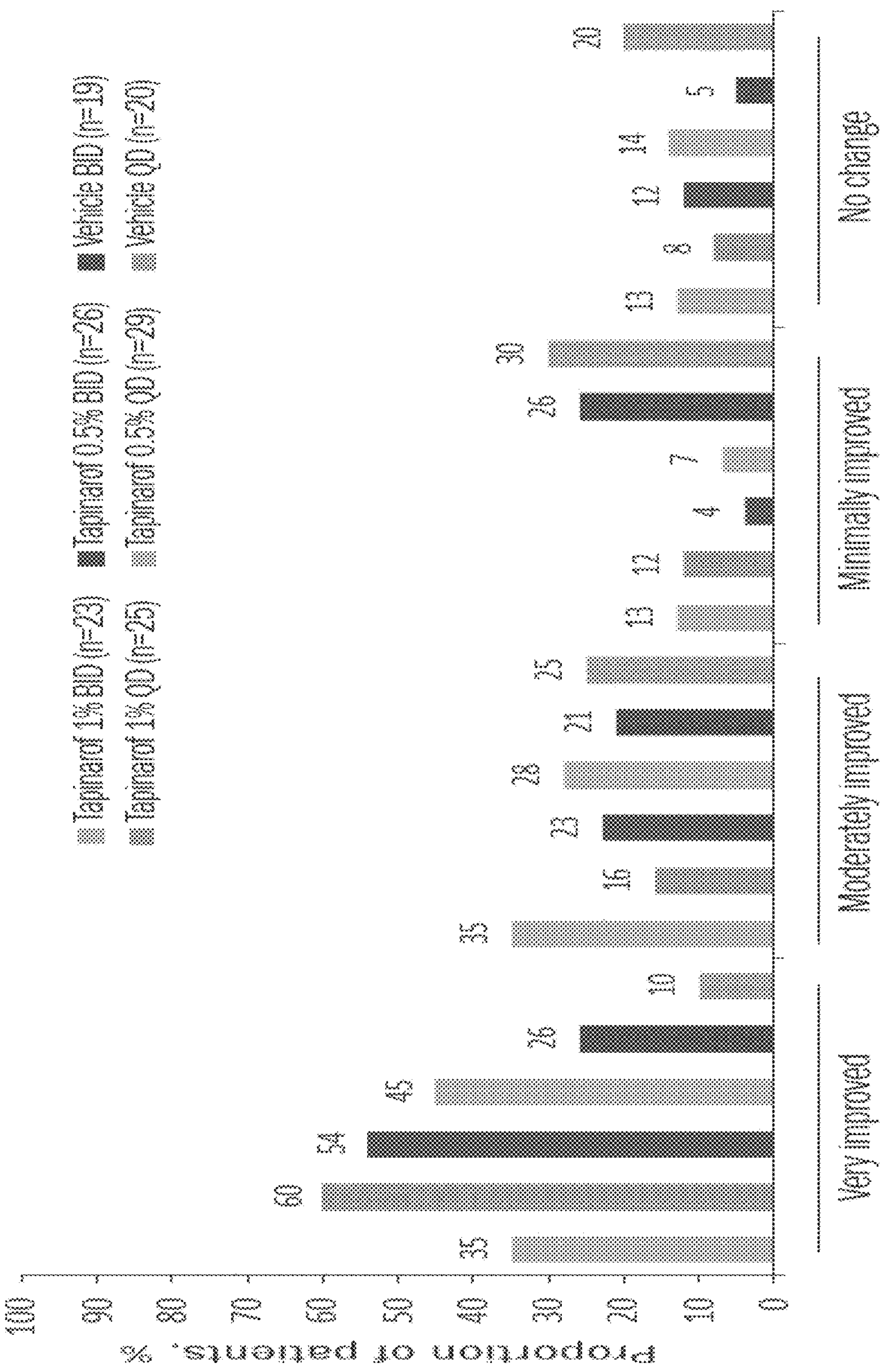
FIG. 15 depicts subject impression of change in severity of pruritus symptoms at Week 12. n is number of subjects with available results at Week 12. BID, twice daily; QD, once daily.

Patient-reported outcomes: At baseline, 95% of subjects rated their psoriasis symptoms as moderate, severe, or very severe across all treatment groups (3-13% rated as them as very severe, 28-44% rated them as severe, and 43-61% rated them as moderate). At Week 12, significantly more subjects in the tapinarof groups rated the overall severity of their psoriasis symptoms as 'very/moderately improved' compared with the vehicle groups: 83% (P=0.019; 1% BID), 88% (P<0.001; 1% QD), 77% (P=0.045; 0.5% BID), and 79% (P=0.002; 0.5% QD) versus 47% (vehicle BID) and 35% (vehicle QD) (FIG. 14). Similarly, more subjects treated with tapinarof cream rated their pruritus symptoms at Week 12 as 'very/moderately improved' compared with the vehicle groups: 70% (P=0.167; 1% BID), 76% (P=0.006; 1% QD), 77% (P=0.045; 0.5% BID), and 72% (P=0.01; 0.5% QD) versus 47% (vehicle BID) and 35% (vehicle QD) (FIG. 15).

Figure 16:
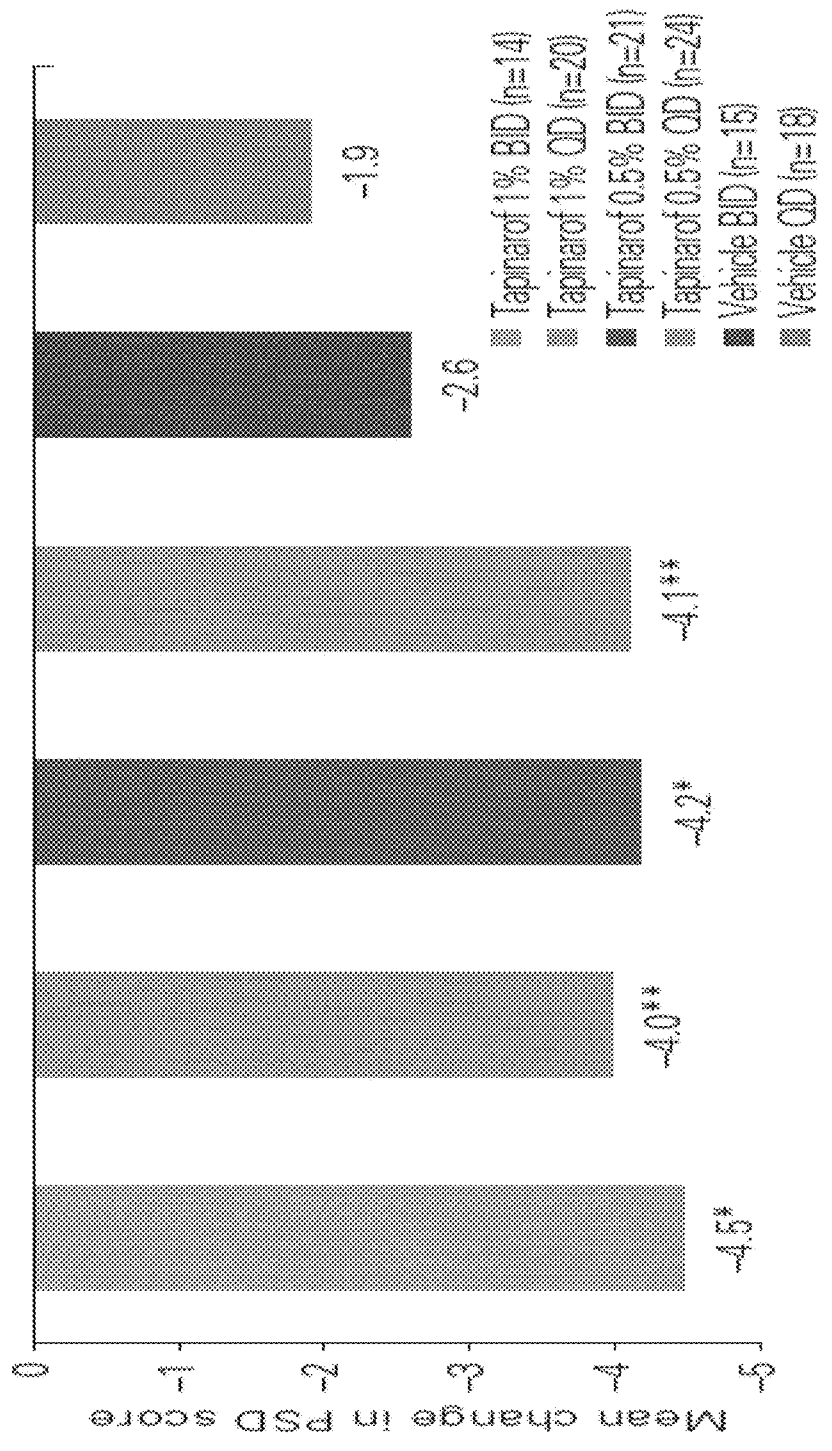
FIG. 16 depicts the mean change from baseline in 9 items of the psoriasis symptom diary at Week 12. Difference versus vehicle is statistically significant at *P<0.05, P<0.01, *P<0.001. n designates the number of subjects with results available at Week 12. BID, twice daily; PSD, Psoriasis Symptom Diary; QD, once daily.

Overall, there was a greater reduction from baseline in mean weekly PSD scores in the tapinarof groups compared with the vehicle groups (FIG. 16). PSD items 2, 11, 12, 13, 14, 17, 18, 19, and 20 (related to itching, scaling, flaking, dryness, and appearance) showed high mean severity scores (≥5 overall) at baseline. By Week 12, scores from these items had significantly reduced in tapinarof groups compared with vehicle indicating clinically meaningful symptom improvement.

Figure 17:
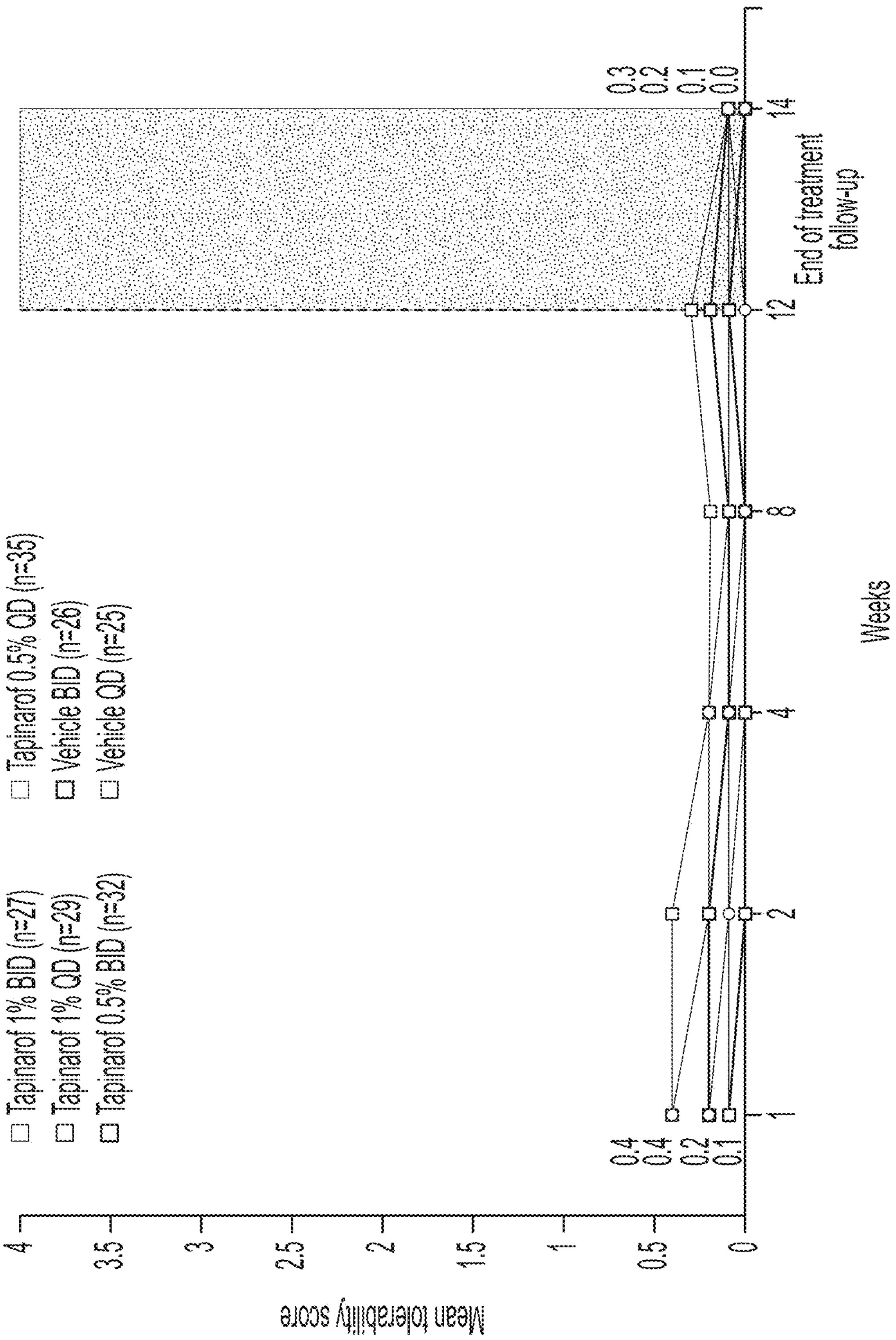
FIG. 17 depicts investigator-assessed tolerability scores over time. Investigator-assessed irritation scores (0-4) assess the presence and overall degree of irritation at the application sites. A score of 3 or 4 was reported to be an adverse event; study treatment was discontinued if a score of 4 was noted. n designates the number of subjects with available results at Week 12 and is the denominator in calculating the percentage at Week 12. BID, twice daily; QD, once daily.
Figure 18:
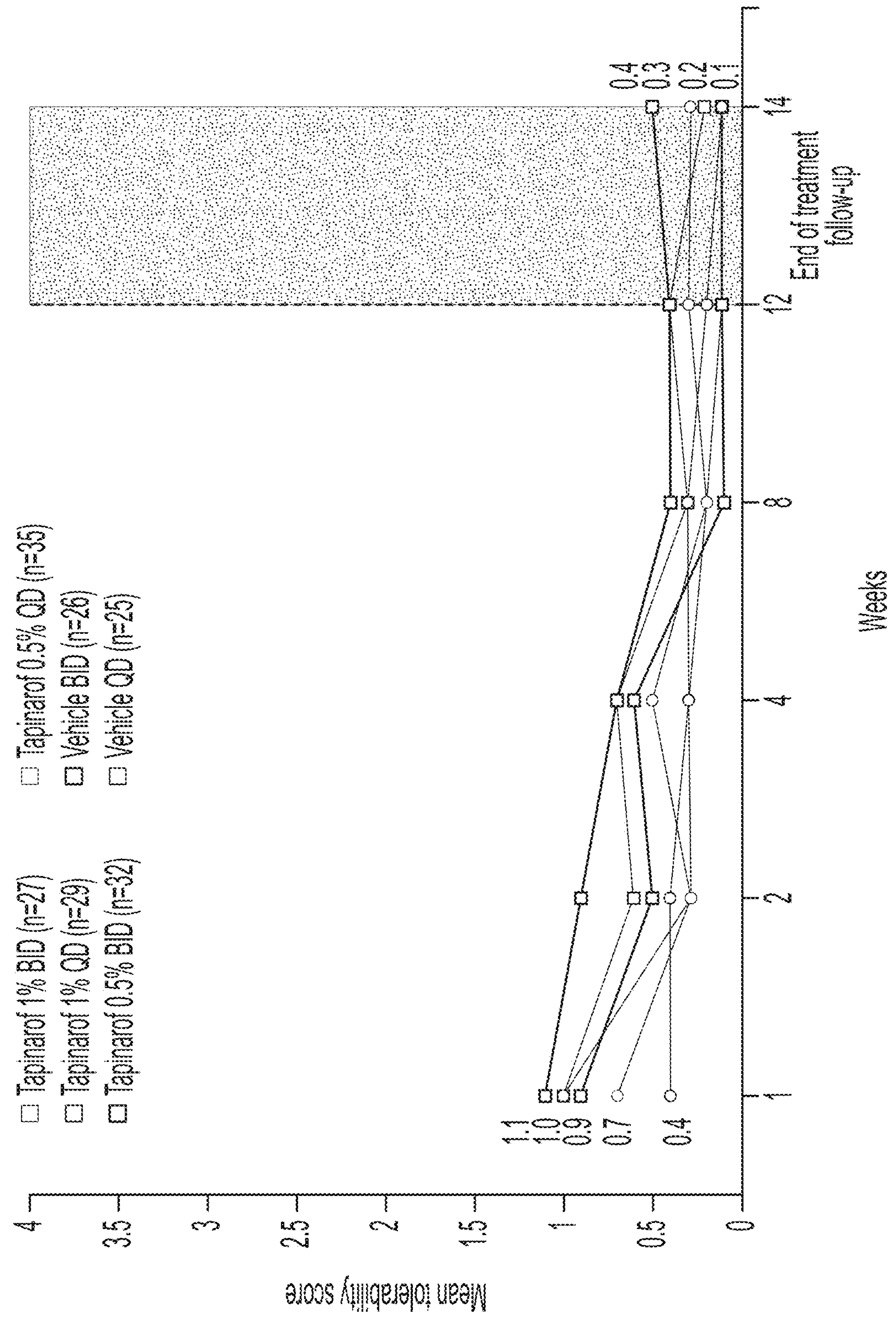
FIG. 18 depicts subject-reported tolerability scores over time. Subject-reported tolerability scores (0-4) assess the presence and degree of burning/stinging and itching at the application sites within approximately 2 hours following application of the study treatment. The score will ideally represent an 'average' across all application sites. n designates the number of subjects with results available at Week 12 and is the denominator in calculating the percentage at Week 12. BID, twice daily; QD, once daily.

Safety, tolerability, and treatment discontinuation: AEs were mostly mild to moderate in severity. The majority of subjects had little to no investigator-assessed treatment-site irritation or self-reported application-site burning/stinging and itching throughout the study period with no apparent differences between tapinarof and vehicle groups. Investigator-reported tolerability scores were predominantly 0 ('no irritation') at Week 1 and were maintained through Week 12 (FIG. 17). Subject-reported tolerability scores were predominantly 0 or 1 ('none' or 'slight' application-site burning/stinging and itching) at Week 1 and improved in all groups over the treatment period through Week 12 (FIG. 18).

Discussion

These results support the previously reported primary analysis showing that tapinarof cream was efficacious and well-tolerated in adults with psoriasis. Tapinarof cream was significantly more efficacious than vehicle in improving PGA response rates at Week 12, which were maintained for 4 weeks during the treatment-free follow-up (Week 16).

Treatment with tapinarof cream resulted in improvements in PASI50 and PASI75 from Week 2, which were statistically significant at Week 8 through Week 16. PASI90 response analyses followed a similar trend of early, durable, and statistically significant efficacy of tapinarof. The sustained durability of response observed in the phase 2b study is intriguing and may provide additional benefit to patients, which will be further explored in phase 3 studies.

The 1% tapinarof cream groups showed higher response rates than 0.5% groups, although response rates were similar in the tapinarof QD and BID groups, suggesting that optimal responses can be achieved with the convenience and improved tolerability of QD dosing.

Total target lesion grading scores improved from Week 2 onwards with tapinarof cream compared with vehicle, and differences were maintained during the treatment-free follow-up (Week 16). By Week 12, a significantly higher proportion of subjects treated with tapinarof 1% QD reported very or moderately improved psoriasis symptoms and psoriasis-related pruritus compared with vehicle QD. These improvements in patient reported outcomes indicate that tapinarof may have a beneficial effect on life quality, psychological well-being, and treatment satisfaction.

The improvements obtained as early as Week 2 in the tapinarof cream 1% QD group, together with the maintenance of effect observed 4 weeks after the cessation of treatment, are promising and warrant further investigation, as early and significant clinical improvement, QD dosing, and maintenance of effect are important factors in ensuring patient adherence and overall treatment success.

Overall, tapinarof cream was well-tolerated, with most AEs reported as mild or moderate.

These results suggest that tapinarof cream is an important advance in topical therapy, having beneficial effects on a range of objective and PROs in psoriasis. The combination of tolerability, efficacy, and durability of response observed suggests that tapinarof has the potential to provide a novel and clinically effective therapeutic option that could help address known limitations of current topical medicines available to this patient population. A phase 3 study of tapinarof cream 1% QD in psoriasis is ongoing (NCT03956355).

Example 4—Tapinarof Cream for the Treatment of Plaque Psoriasis: Efficacy and Safety by Baseline Disease Characteristics and Skin Type in a Phase 2b Randomized Study Tapinarof is a therapeutic aryl hydrocarbon receptor modulating agent (TAMA) in development for the treatment of psoriasis and atopic dermatitis. In a previously reported phase 2b efficacy and safety study (NCT02564042), Physician Global Assessment (PGA) responses (0 or 1 and ≥2-grade improvement from baseline) at Week 12 were significantly higher in all tapinarof cream groups vs vehicle. Tapinarof cream demonstrated durable PGA responses through 4 weeks after the end of study treatment.

A post-hoc analysis of PGA response stratified by baseline % body surface area (BSA) affected, psoriasis duration, and Fitzpatrick skin type was conducted to evaluate the efficacy and safety of tapinarof cream vs vehicle across subgroups.

Overall, mean baseline disease characteristics were comparable across groups. Most subjects (80%) had a baseline PGA score of 3 (moderate). Mean baseline Psoriasis Area and Severity Index score was 8.8.

Stratified by baseline BSA, PGA response at Week 12 in subjects treated with tapinarof 1% twice daily (BID), 1% once daily (QD), 0.5% BID, and 0.5% QD vs vehicle BID and vehicle QD was: 67%, 60%, 33%, and 35% vs 13% and 6%, respectively (1 to <10% BSA affected; n=102); and 64%, 40%, 75%, and 38% vs 0% and 0%, respectively (≥10% BSA affected; n=39).

Stratified by psoriasis duration, PGA response at Week 12 in subjects treated with tapinarof 1% BID, 1% QD, 0.5% BID, and 0.5% QD vs vehicle BID and vehicle QD was: 50%, 80%, 50%, and 29% vs 0% and 0%, respectively (6 months to <5 years; n=27); 67%, 50%, 20%, and 50% vs 25% and 0% (5 years to <10 years; n=32); and 73%, 50%, 53%, and 33% vs 8% and 8% (≥10 years; n=82).

Stratified by Fitzpatrick skin type, PGA response at Week 12 in subjects treated with tapinarof 1% BID, 1% QD, 0.5% BID, and 0.5% QD vs vehicle BID and vehicle QD was: 60%, 67%, 50%, and 25% vs 0% and 10%, respectively (Fitzpatrick skin type I/II; n=41); 54%, 47%, 60%, and 44% vs 18% and 0% (Fitzpatrick skin type III/IV; n=73); and 100%, 75%, 25%, and 25% vs 0% and 0% (Fitzpatrick skin type V/VI; n=27).

Incidence and type of adverse events were generally comparable across groups and consistent with those observed in the overall population.

Tapinarof cream was efficacious and well tolerated across subgroups regardless of baseline % BSA affected, psoriasis duration, or Fitzpatrick skin type. A phase 3 study of tapinarof cream 1% QD in psoriasis is ongoing (NCT03956355).

Figure 19:
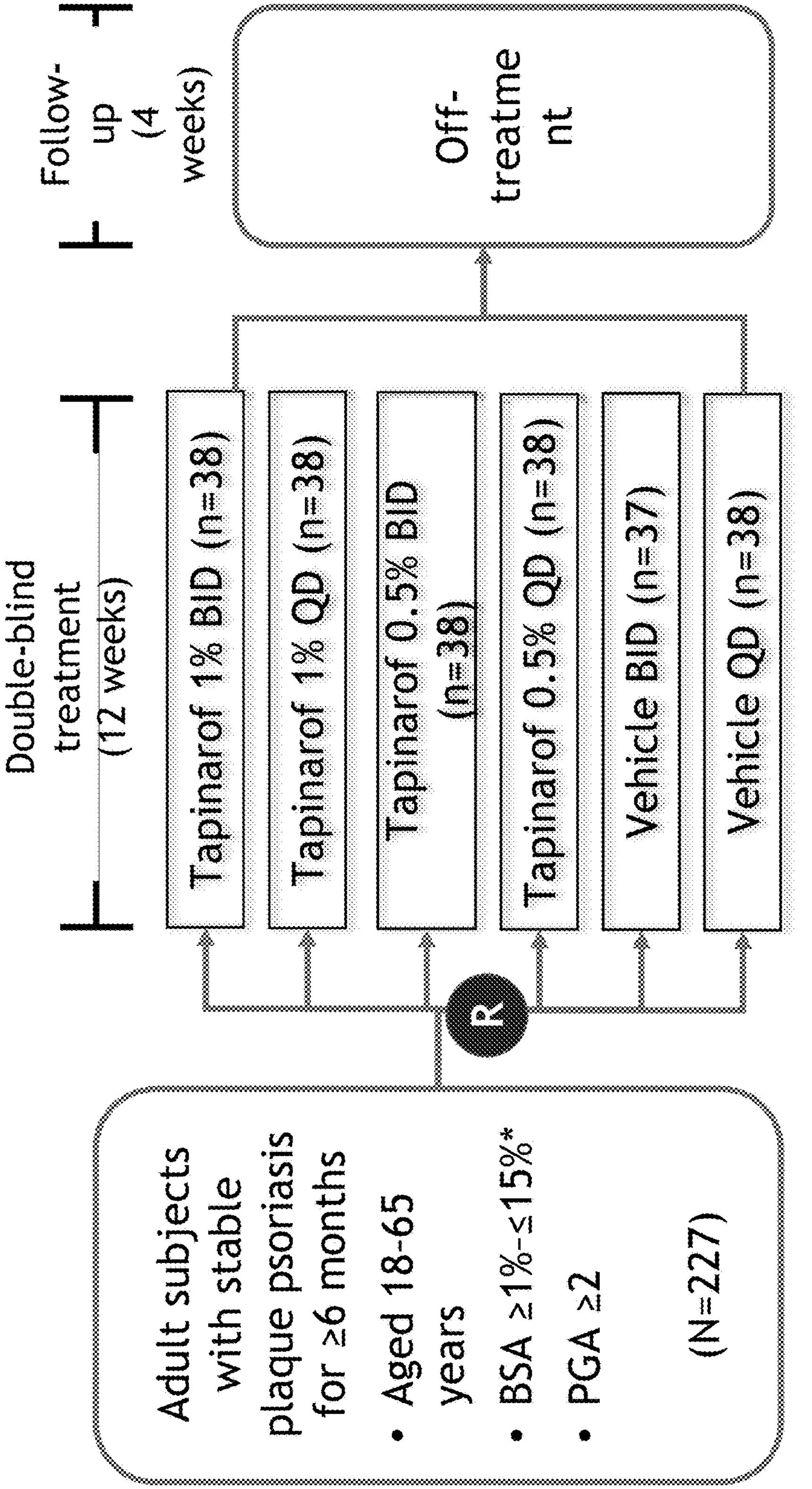
FIG. 19 shows the study design.

Study Design: In this multicenter (United States, Canada, and Japan), phase 2b, double-blind, vehicle-controlled randomized study, adult subjects with psoriasis were randomized 1:1:1:1:1:1 to receive tapinarof cream 0.5% or 1% once (QD) or twice daily (BID) or vehicle QD or BID for 12 weeks and followed up for 4 more weeks (FIG. 19)

Study Outcomes and Statistical Analysis: The primary endpoint was Physician Global Assessment (PGA) response rates at Week 12, defined as the proportion of subjects with a PGA score of clear or almost clear (0 or 1) and ≥2-grade improvement in PGA score from baseline to Week 12. Additional post-hoc efficacy analyses reported here include PGA response rates at Week 12, stratified by the following baseline disease characteristics and skin type: Baseline % BSA affected: 1 to ≤10% and ≥10%, Baseline duration of psoriasis: 6 months to <5 years, 5 years to <10 years, and ≥10 years, Fitzpatrick skin type: Fitzpatrick skin type I and II, Fitzpatrick skin type III and IV, and Fitzpatrick skin type V and VI. Incidence, frequency, and nature of adverse events (AEs) and serious AEs were collected from the start of study treatment until the end of study visit at Week 16.

Results

Subject Characteristics: A total of 227 subjects (of the 290 subjects originally screened) were randomized (intent-to-treat population) and of those randomized, 175 subjects (77%) completed the study, including the Week 16 follow-up visit. Mean demographic and baseline characteristics were comparable across treatment groups (Table 13). Overall, 15% of subjects had a baseline PGA category of 2 (mild), 80% had a PGA category of 3 (moderate), and 5% had a PGA category of 4 (severe). Baseline mean Psoriasis Area and Severity Index score was 8.8 (standard deviation [SD] 4.5).

TABLE 13

Baseline Subject Demographics and Characteristics

| | Tapinarof 1% cream | | Tapinarof 0.5% cream | | Vehicle | |
|---|---|---|---|---|---|---|
| | BID (n = 38) | QD (n = 38) | BID (n = 38) | QD (n = 38) | BID (n = 37) | QD (n = 38) |
| Age, mean (SD), years | 45.9 (11.9) | 48.5 (10.6) | 49.6 (10.9) | 48.7 (9.7) | 46.7 (12.6) | 46.4 (10.2) |
| Male sex, n (%) | 26 (68) | 26 (68) | 24 (63) | 25 (66) | 23 (62) | 29 (76) |
| Weight, mean (SD), kg | 85.6 (22.5) | 86.7 (22.6) | 88.6 (27.4) | 89.3 (23.1) | 87.8 (28.3) | 91.6 (21.6) |
| PGA score, mean (SD*) | 2.9 (0.4) | 2.7 (0.5) | 3.0 (0.5) | 2.9 (0.4) | 3.0 (0.3) | 2.8 (0.4) |
| PASI score, mean (SD)* | 10.6 (5.0) | 8.5 (3.6) | 8.2 (4.5) | 7.9 (4.8) | 9.0 (4.3) | 8.7 (4.4) |
| BSA affected, mean (SD), %* | 8.2 (4.5) | 6.5 (3.3) | 7.2 (4.5) | 6.1 (4.3) | 6.6 (3.6) | 7.0 (4.6) |
| Pruritus score, mean (SD)*† | 5.6 (2.6) | 4.4 (2.9) | 6.2 (2.2) | 4.5 (2.6) | 5.5 (2.8) | 4.9 (2.4) |
| Fitzpatrick skin type I, n (%) | 2 (6) | 3 (9) | 1 (3) | 2 (6) | 1 (3) | 1 (3) |
| Fitzpatrick skin type II, n (%) | 8 (24) | 7 (20) | 10 (31) | 6 (19) | 5 (17) | 13 (39) |
| Fitzpatrick skin type III, n (%) | 17 (50) | 14 (40) | 6 (19) | 13 (41) | 11 (37) | 11 (33) |
| Fitzpatrick skin type IV, n (%) | 2 (6) | 7 (20) | 7 (22) | 7 (22) | 7 (23) | 5 (15) |
| Fitzpatrick skin type V, n (%) | 5 (15) | 3 (9) | 5 (16) | 4 (13) | 5 (17) | 3 (9) |
| Fitzpatrick skin type VI, n (%) | 0 | 1 (3) | 3 (9) | 0 | 1 (3) | 0 |

Baseline disease characteristics provided for the mITT population (n = 196), which included subjects in the ITT population minus the subjects from one site due to protocol violation. Demographics (age, sex, and weight) provided for the safety population (n = 227).
*Mean scores based on a scale of 0 'absent' to 10 'worst imaginable'; data provided for subjects with available results (n = 32, 35, 30, 32, 29, and 32, respectively).
BID, twice daily; BSA, body surface area; ITT, intent-to-treat; mITT, modified intent-to-treat; PASI, Psoriasis Area and Severity Index; PGA, Physician Global Assessment; QD, once daily; SD, standard deviation.

PGA Response Rates: Primary endpoint: PGA response rates (defined as PGA score 0 or 1 and ≥2-grade improvement) at Week 12 were significantly higher (at 0.05 significance level) in the tapinarof cream groups than the vehicle groups (65% [1% BID], 56% [1% QD], 46% [0.5% BID], 36% [0.5% QD] vs 11% [vehicle BID] and 5% [vehicle QD]) and were maintained for 4 weeks after the end-of-study treatment in all active treatment groups except for the 0.5% BID group.

Figure 20:
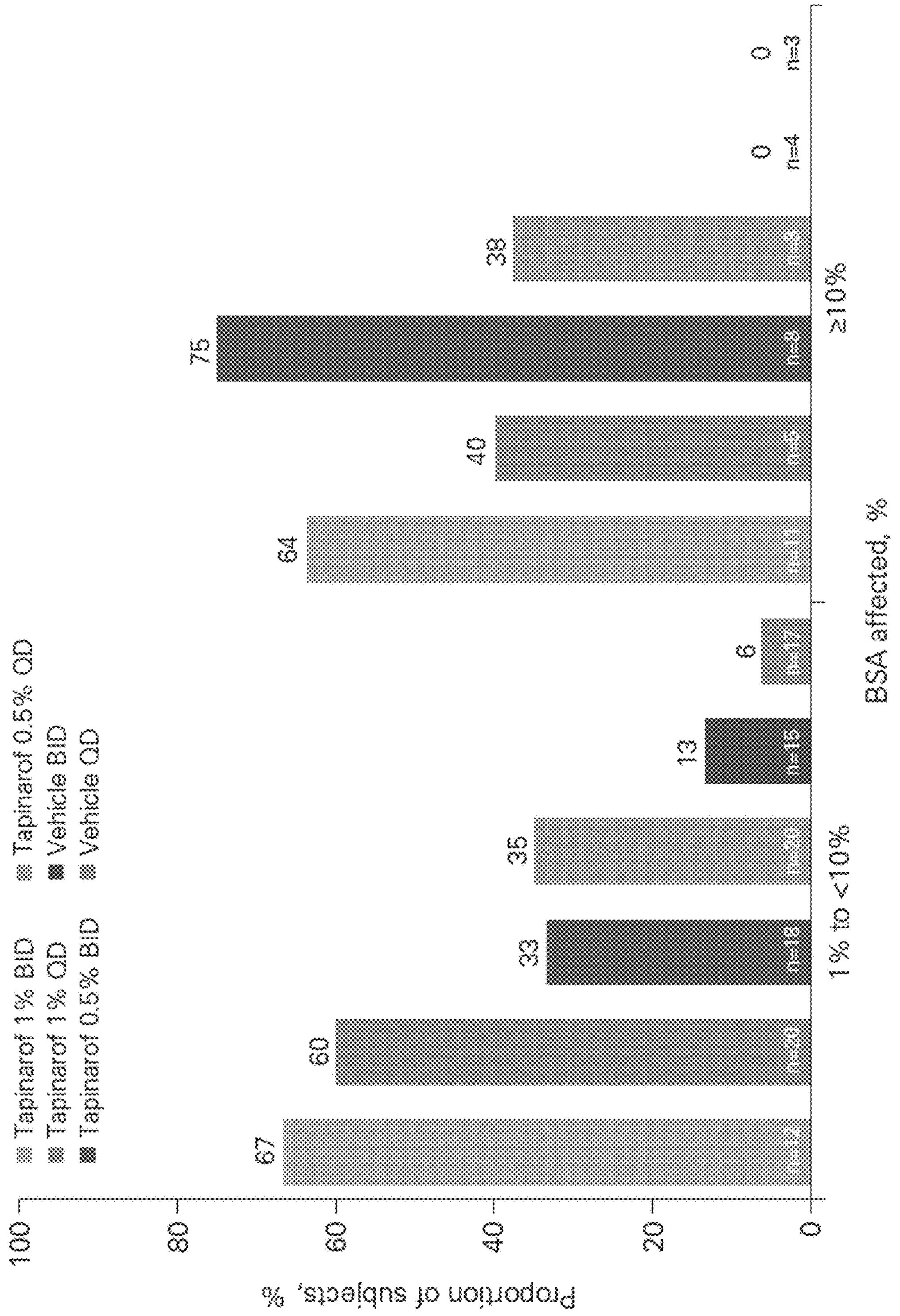
FIG. 20 depicts the proportion of Subjects who achieved PGA response at Week 12 by % BSA Affected at Baseline.

PGA Response Rates by Baseline % BSA Affected: PGA response rates at Week 12 were higher in tapinarof cream groups than vehicle groups, regardless of baseline % BSA affected (FIG. 20), 1 to <10% BSA affected (n=102): 67% (1% BID), 60% (1% QD), 33% (0.5% BID), and 35% (0.5% QD) vs 13% (vehicle BID) and 6% (vehicle QD), ≥10% BSA affected (n=39): 64% (1% BID), 40% (1% QD), 75% (0.5% BID), and 38% (0.5% QD) vs 0% (vehicle BID) and 0% (vehicle QD).

Figure 21:
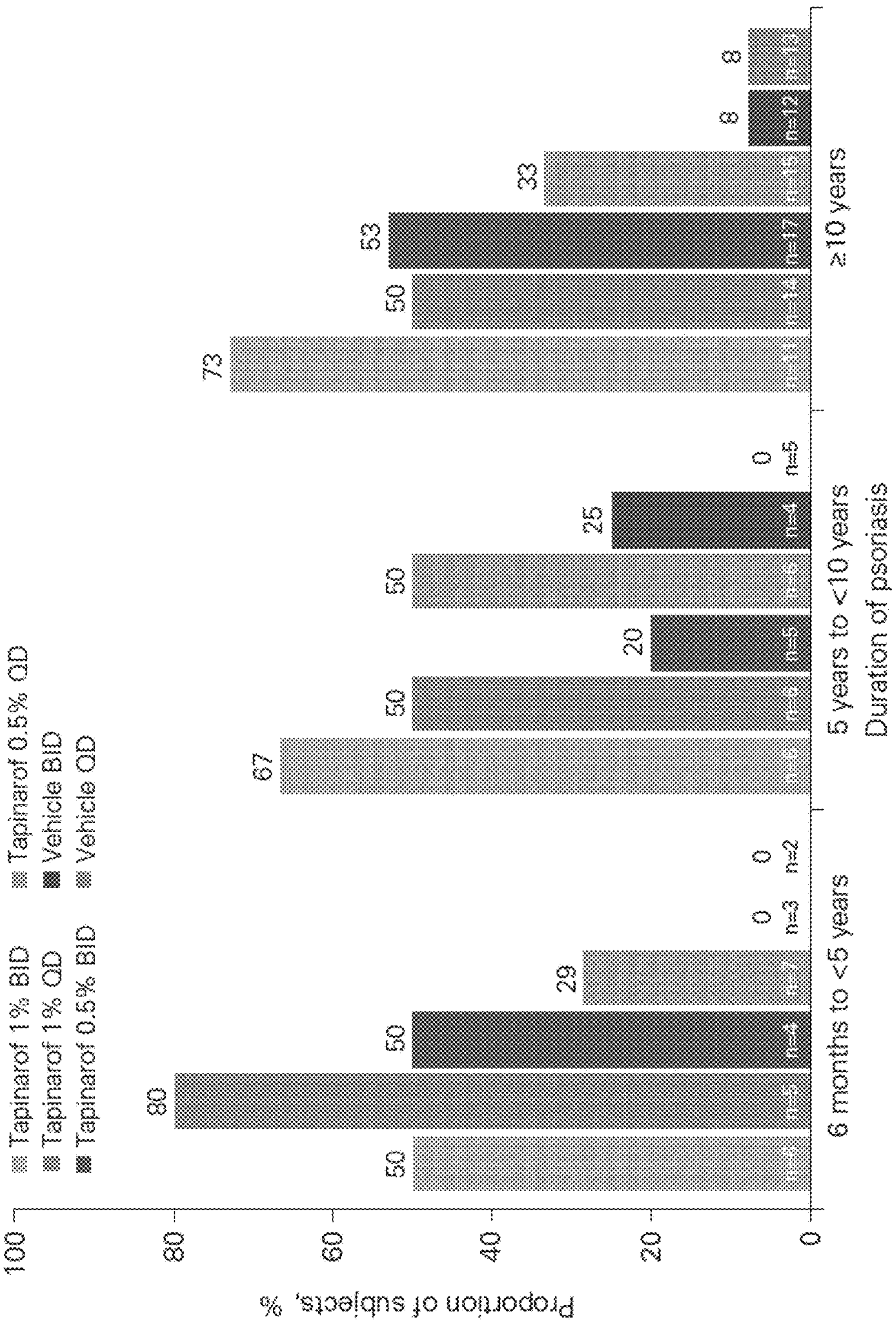
FIG. 21 depicts the proportion of Subjects who achieved PGA response at Week 12 by Duration of Psoriasis at Baseline.

PGA Response Rates by Baseline Duration of Psoriasis: PGA response rates at Week 12 were higher in tapinarof cream groups than in vehicle groups, regardless of baseline duration of psoriasis, except for the 0.5% BID treatment group in the 5 years to <10 years subgroup (FIG. 21), 6 months to <5 years (n=27): 50% (1% BID), 80% (1% QD), 50% (0.5% BID), and 29% (0.5% QD) vs 0% (vehicle BID) and 0% (vehicle QD); 5 years to <10 years (n=32): 67% (1% BID), 50% (1% QD), 20% (0.5% BID), and 50% (0.5% QD) vs 25% (vehicle BID) and 0% (vehicle QD); ≥10 years (n=82): 73% (1% BID), 50% (1% QD), 53% (0.5% BID), and 33% (0.5% QD) vs 8% (vehicle BID) and 8% (vehicle QD).

Figure 22:
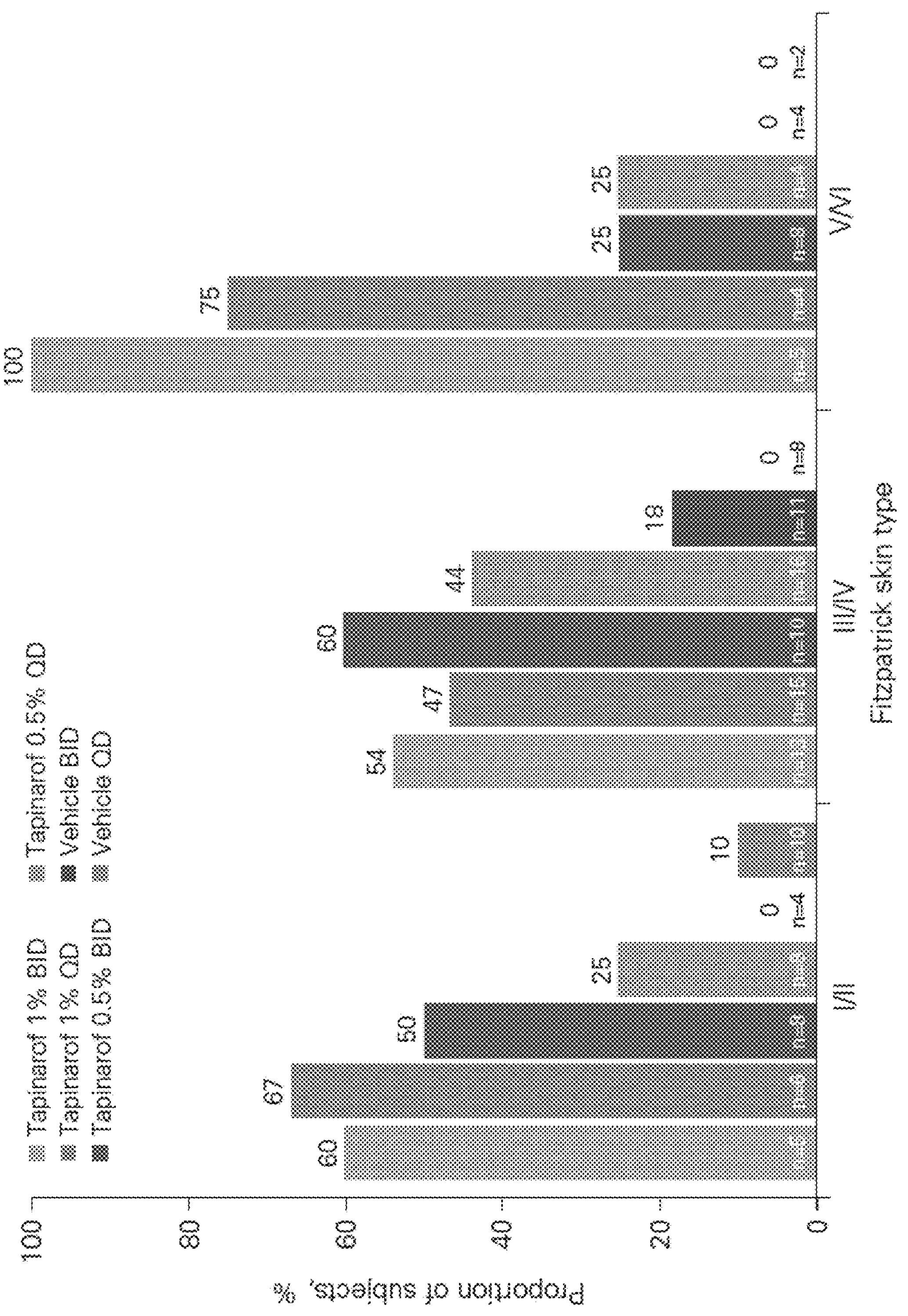
FIG. 22 depicts the proportion of Subjects who achieved PGA response at Week 12 by Fitzpatrick Skin Type.

Safety: Treatment-emergent AEs (TEAEs) were mostly mild to moderate in severity. The most common treatment-related TEAEs were folliculitis (10% tapinarof vs 1% vehicle), contact dermatitis (3%; all tapinarof), and headache (1%; all tapinarof). Incidence and type of AEs were generally comparable across subgroups and consistent with those observed in the overall population Conclusions Overall, tapinarof cream was efficacious and well tolerated regardless of baseline % BSA affected, psoriasis duration, and Fitzpatrick skin type (FIG. 22). Higher PGA response rates at Week 12 were observed in the 1% QD tapinarof cream group vs vehicle across all subgroups. These findings support the previously reported efficacy and safety outcomes of the overall population. A phase 3 study of tapinarof cream 1% QD in psoriasis is ongoing.

What is claimed:

1. A method for treating mild to severe atopic dermatitis in a subject that is 2 years of age or older comprising topically administering to the subject a topical composition containing about 1.0% tapinarof to affected areas of the subject once a day, wherein after topically administering the topical composition an Investigator Global Assessment (IGA) score of the subject is improved by 2 grades and achieves an itch/pruritus numeric rating scale (NRS) score improvement of greater than or equal to 4 from baseline within 4 weeks and wherein topically administering the topical composition results in systemic exposure of tapinarof that is below the limit of detection.

2. The method of claim 1, wherein the topical composition is an oil-in-water emulsion.

3. The method of claim 2, wherein the oil phase of the oil-in-water emulsion is comprised of medium chain triglycerides, propylene glycol, non-ionic emulsifying wax, diethylene glycol monoethyl ether, polyoxyl stearyl ether-2, polysorbate 80, polyoxyl stearyl ether-20, benzoic acid, and butylated hydroxytoluene.

4. The method of claim 2, wherein the water phase of the oil-in-water emulsion is comprised of sodium citrate, edetate disodium, citric acid monohydrate, and water.

5. The method of claim 1, wherein the subject is between the age of 2 and 18.

6. The method of claim 1, wherein the topically administering includes application to the affected area of the skin selected from the group consisting of body, arms, legs, back, chest, buttocks, neck, scalp, fingernails, toenails, and combinations thereof.

7. The method of claim 1, wherein the subject has been diagnosed with mild to severe atopic dermatitis having a percent body surface area (BSA) affected of about 3% to about 20%.

8. The method of claim 1, wherein the subject has been diagnosed with mild to severe atopic dermatitis having an Investigator Global Assessment (IGA) score of greater than or equal to 3.

9. The method of claim 1, further comprising, after topically administering the topical composition, an improvement of one or more symptom of mild to severe atopic dermatitis as measured according to an assessment selected from the group consisting of Investigator Global Assessment (IGA) score, daily Itch/Pruritus numeric rating scale, Eczema Area and Severity Index (EASI), total severity score, percent body surface area (BSA) affected, sleep quality, dry/rough skin, red/discolored skin, flaky skin, visual analogue scale (VAS) for sleep, visual analogue scale (VAS) for itch, and patient reported outcomes.

10. The method of claim 9, wherein the Eczema Area and Severity Index (EASI) is improved by greater than or equal to 50% or is improved by greater than or equal to 75%.

11. The method of claim 9, wherein the percent body surface area (BSA) affected is decreased to less than 20%.

12. The method of claim 9, wherein the sleep quality is improved as measured by the visual analogue scale (VAS) for sleep.

13. The method of claim 9, wherein the patient reported outcomes demonstrated that subject's impressions of symptom severity was improved, wherein the symptoms are selected from the group consisting of itchy skin, red/discolored skin, bleeding, weeping or oozing skin, cracked skin, scaly skin, flaky skin, dry or rough skin, painful skin, burning skin, and disturbed sleep.

14. The method of claim 9, wherein the one or more symptom is improved after about 2 weeks, about 4 weeks, or about 8 weeks of administering the topical composition.

15. The method of claim 9, wherein the improvement of one or more symptom continues for about 4 weeks after administration of the topical composition has ceased.

16. The method of claim 1, wherein the IGA score is improved after about 2 weeks, about 4 weeks, or about 8 weeks of administering the topical composition.

17. The method of claim 1, wherein the improvement in IGA score continues for about 4 weeks after administration of the topical composition has ceased.

18. The method of claim 1, further comprising after topically administering the topical composition an improvement of one or more symptom of mild to severe atopic dermatitis as measured according to an assessment selected from the group consisting of daily Itch/Pruritus numeric rating scale (NRS), total severity score (TSS), dry/rough skin, red/discolored skin, flaky skin, visual analogue scale (VAS) for sleep, visual analogue scale (VAS) for itch, patient reported outcomes, and combinations thereof.

19. The method of claim 1, further comprising after topically administering the topical composition an improvement of one or more subject-reported outcomes selected from the group consisting of Subject Impression of Severity and Change questionnaire, expanded Patient-Oriented Eczema Measure (POEM), Daily Sign and Symptom Severity Diary, and combinations thereof.

20. The method of claim 1, wherein administration of the topical composition exhibits no accumulation of tapinarof in plasma of the subject with repeat administration.

* * * * *